United States Patent
Smith et al.

(10) Patent No.: US 9,138,217 B2
(45) Date of Patent: Sep. 22, 2015

(54) SURGICAL ACCESS SYSTEM AND RELATED METHODS

(75) Inventors: William D. Smith, Las Vegas, NV (US); Troy B. Woolley, Erie, CO (US); Brian Snider, San Diego, CA (US); Michael Serra, San Diego, CA (US); Michael Mindoro, Richmond, CA (US)

(73) Assignee: Nu Vasive, Inc., San Diego, CA (US)

(*) Notice: Subject to any disclaimer, the term of this patent is extended or adjusted under 35 U.S.C. 154(b) by 453 days.

(21) Appl. No.: 13/509,064

(22) PCT Filed: Nov. 12, 2010

(86) PCT No.: PCT/US2010/002960
§ 371 (c)(1),
(2), (4) Date: Jul. 30, 2012

(87) PCT Pub. No.: WO2011/059498
PCT Pub. Date: May 19, 2011

(65) Prior Publication Data
US 2012/0283521 A1    Nov. 8, 2012

Related U.S. Application Data

(60) Provisional application No. 61/260,303, filed on Nov. 11, 2009, provisional application No. 61/263,356, filed on Nov. 21, 2009.

(51) Int. Cl.
| | | |
|---|---|---|
| A61B 1/32 | (2006.01) | |
| A61B 17/02 | (2006.01) | |
| A61B 17/17 | (2006.01) | |
| A61B 17/00 | (2006.01) | |
| A61B 19/00 | (2006.01) | |

(52) U.S. Cl.
CPC ......... *A61B 17/0206* (2013.01); *A61B 17/1757* (2013.01); *A61B 2017/00199* (2013.01); *A61B 2017/0262* (2013.01); *A61B 2019/467* (2013.01)

(58) Field of Classification Search
CPC ........... A61B 17/0206; A61B 17/1757; A61B 2019/467; A61B 2017/00199; A61B 2017/0262
USPC .................. 600/201, 205, 208, 210, 213–219
See application file for complete search history.

(56) References Cited

U.S. PATENT DOCUMENTS

| | | |
|---|---|---|
| 1,238,863 A | 9/1917 | Willour |
| 1,486,723 A | 3/1924 | Bernson |
| 1,896,715 A | 2/1933 | Martinetti |
| 5,299,563 A * | 4/1994 | Seton .......................... 600/215 |
| 5,480,442 A | 1/1996 | Bertagnoli |
| 5,571,192 A | 11/1996 | Schönhöffer |
| 5,575,790 A | 11/1996 | Chen et al. |
| 5,693,100 A | 12/1997 | Pisharodi |
| 5,702,453 A | 12/1997 | Rabbe et al. |
| 5,702,455 A | 12/1997 | Saggar |

(Continued)

OTHER PUBLICATIONS

International Search Report and Written Opinion of the International Searching Authority in International Application No. PCT/US2010/002960 dated Jan. 12, 2011, 7 pages.

*Primary Examiner* — Christopher Beccia
*Assistant Examiner* — Diana S Jones
(74) *Attorney, Agent, or Firm* — Jonathan Spangler; Rory Schermerhorn

(57) ABSTRACT

A minimally invasive surgical procedure, and related systems, for creating a minimally invasive operating corridor from a generally lateral approach, for example for performing corpectomies in the lumbar and thoracic regions of the spine.

10 Claims, 87 Drawing Sheets

(56) References Cited

U.S. PATENT DOCUMENTS

| | | |
|---|---|---|
| 5,723,013 A | 3/1998 | Jeanson et al. |
| 5,776,197 A | 7/1998 | Rabbe et al. |
| 5,776,198 A | 7/1998 | Rabbe et al. |
| 5,989,290 A | 11/1999 | Biedermann et al. |
| 6,015,436 A | 1/2000 | Schönhöffer |
| 6,176,881 B1 | 1/2001 | Schär et al. |
| 6,190,413 B1 | 2/2001 | Sutcliffe |
| 6,193,756 B1 | 2/2001 | Studer et al. |
| 6,200,348 B1 | 3/2001 | Biedermann et al. |
| 6,214,050 B1 | 4/2001 | Huene |
| 6,258,125 B1 | 7/2001 | Paul et al. |
| 6,296,665 B1 | 10/2001 | Strnad et al. |
| 6,344,057 B1 | 2/2002 | Rabbe et al. |
| 6,352,556 B1 | 3/2002 | Kretschmer et al. |
| 6,524,341 B2 | 2/2003 | Läng et al. |
| 6,730,088 B2 | 5/2004 | Yeh |
| 6,866,682 B1 | 3/2005 | An et al. |
| 6,896,517 B1 | 5/2005 | Björn et al. |
| 6,902,579 B2 | 6/2005 | Harms et al. |
| 7,022,138 B2 | 4/2006 | Mashburn |
| 7,056,343 B2 | 6/2006 | Schafer et al. |
| 7,207,949 B2 | 4/2007 | Miles et al. |
| 7,470,236 B1 | 12/2008 | Kelleher et al. |
| 7,522,953 B2 | 4/2009 | Kaula et al. |
| D594,986 S | 6/2009 | Miles et al. |
| D599,019 S | 8/2009 | Pimenta et al. |
| 7,582,058 B1 | 9/2009 | Miles |
| 7,641,693 B2 | 1/2010 | Gutlin et al. |
| 7,691,057 B2 | 4/2010 | Miles |
| D621,509 S | 8/2010 | Lovell |
| 7,819,801 B2 | 10/2010 | Miles |
| 7,905,840 B2 | 3/2011 | Pimenta |
| 7,918,891 B1 | 4/2011 | Curran et al. |
| 7,920,922 B2 | 4/2011 | Gharib |
| 7,962,191 B2 | 6/2011 | Marino |
| 8,137,284 B2 | 3/2012 | Miles |
| 8,255,045 B2 | 8/2012 | Gharib |
| 8,287,597 B1 | 10/2012 | Pimenta |
| 8,313,430 B1 | 11/2012 | Pimenta |
| 8,328,851 B2 | 12/2012 | Curran |
| 8,343,163 B1 | 1/2013 | Arambula |
| 8,790,406 B1 | 7/2014 | Smith |
| 8,876,904 B2 | 11/2014 | Pimenta |
| 2002/0082695 A1 | 6/2002 | Neumann |
| 2004/0186569 A1 | 9/2004 | Berry |
| 2005/0107878 A1 | 5/2005 | Conchy |
| 2005/0228232 A1 | 10/2005 | Gillinov et al. |
| 2006/0100710 A1 | 5/2006 | Gutlin et al. |
| 2006/0241770 A1 | 10/2006 | Rhoda et al. |
| 2007/0028710 A1 | 2/2007 | Kraus et al. |
| 2007/0100212 A1 | 5/2007 | Pimenta et al. |
| 2007/0208227 A1* | 9/2007 | Smith et al. .................... 600/219 |
| 2008/0097164 A1 | 4/2008 | Miles et al. |
| 2008/0114467 A1 | 5/2008 | Capote et al. |
| 2012/0283521 A1 | 11/2012 | Smith |

* cited by examiner

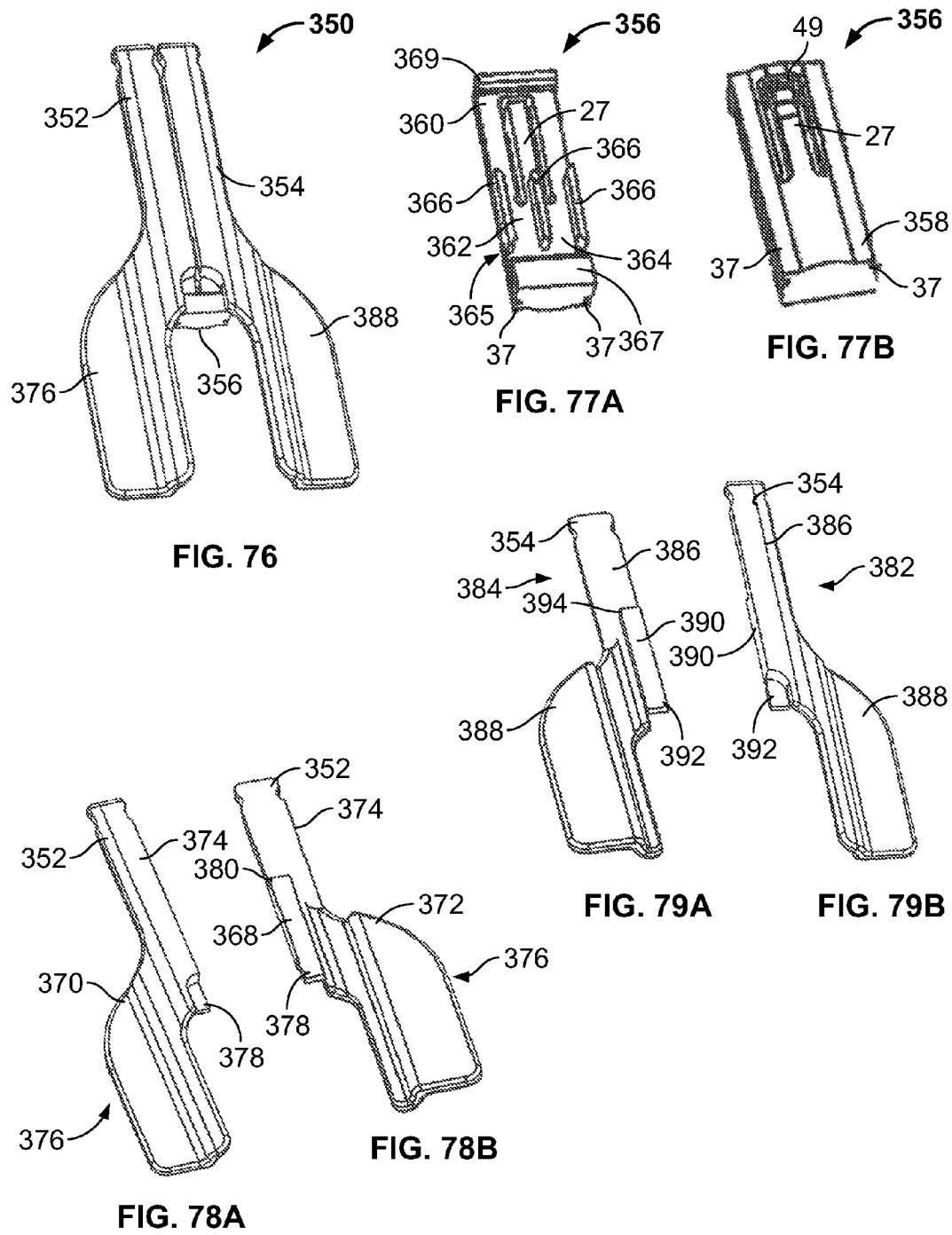

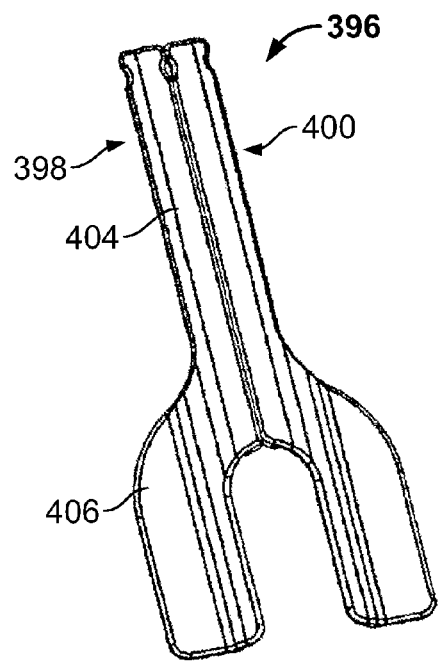
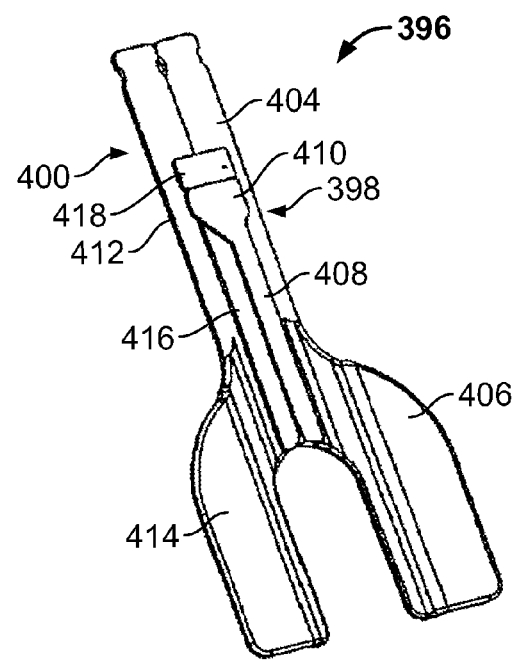
FIG. 81
FIG. 82
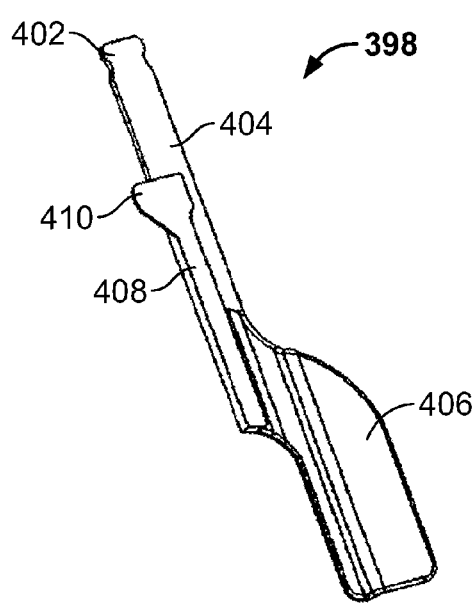
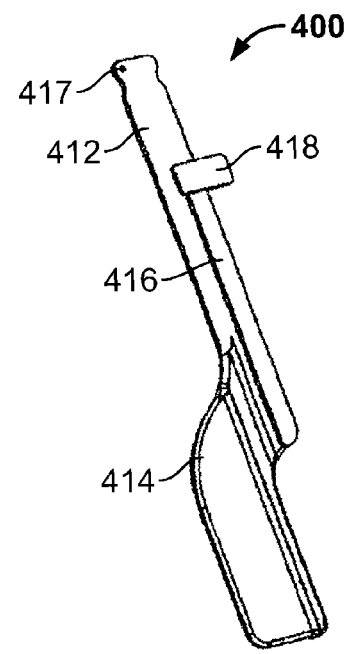
FIG. 83
FIG. 84

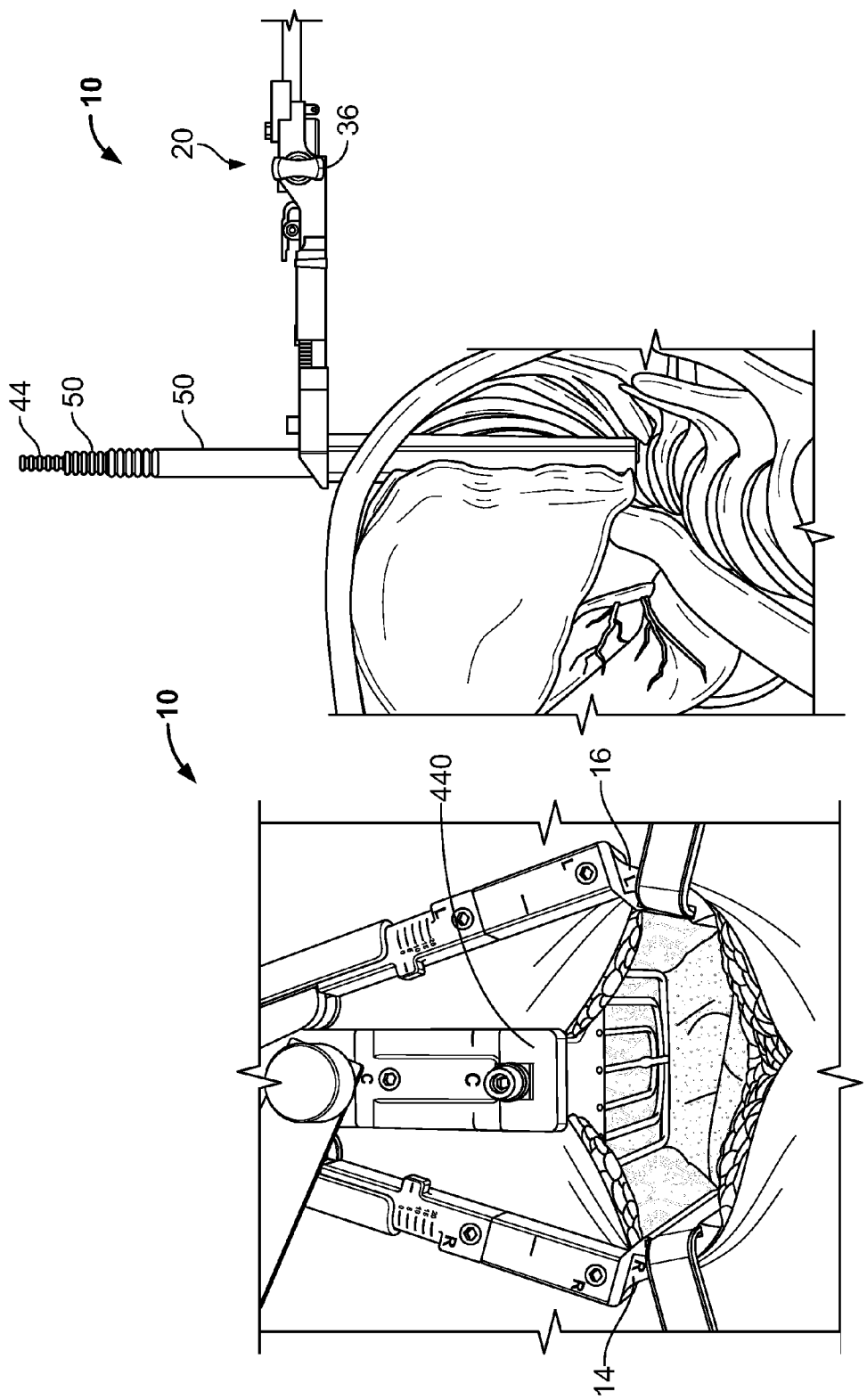

SURGICAL ACCESS SYSTEM AND RELATED METHODS

CROSS REFERENCE TO RELATED APPLICATIONS

This international patent application claims the benefit of priority from U.S. Provisional Patent Application Ser. No. 61/260,303, entitled "Surgical Access System and Related Methods," filed on Nov. 11, 2009, and U.S. Provisional Patent Application Ser. No. 61/263,356, entitled "Surgical Access System and Related Methods," filed on Nov. 21, 2009, the entire contents of which are each hereby expressly incorporated by reference into this disclosure as if set forth in its entirety herein.

FIELD

This application describes systems and methods and methods for performing surgical procedures and, more particularly, for accessing a surgical target site in order to perform surgical procedures.

BACKGROUND

A noteworthy trend in the medical community is the move away from performing surgery via traditional "open" techniques in favor of minimally invasive or minimal access techniques. Open surgical techniques are generally undesirable in that they typically require large incisions and high amounts of tissue displacement to gain access to the surgical target site, which produces concomitantly high amounts of pain, lengthened hospitalization (increasing health care costs), and high morbidity in the patient population. Less-invasive surgical techniques (including so-called "minimal access" and "minimally invasive" techniques) are gaining favor due to the fact that they involve accessing the surgical target site via incisions of substantially smaller size with greatly reduced tissue displacement requirements. This, in turn, reduces the pain, morbidity and cost associated with such procedures. While minimally invasive techniques have been developed and well utilized for many spinal procedures, corpectomies (removal of at least part of one or more vertebral bodies) often performed to treat tumors and fractures of the spine, particularly thoracic corpectomies, are still highly invasive procedures. The thoracotomy incision, commonly referred to as a "shark bite", generally utilized for accessing the thoracic spine is extremely painful and can lead to complications and a very difficult recovery period. Additionally, the anatomy of the thoracic region and the delicate structures found in the region often necessitate that an additional surgeon, such as a vascular surgeon, assist the spinal surgeon in performing the corpectomy, adding both time and cost to the surgical procedure.

The present invention is directed towards addressing these challenges.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIGS. 76-79 are perspective views of a sequential retractor extender, according to one example embodiment;

FIGS. 81-84 are perspective views of a sequential retractor extender, according to another example embodiment;

FIGS. 95-108 are figures illustrating steps to perform a lateral transpleural approach to the thoracic spine, according to one example;

DETAILED DESCRIPTION

Figure 1:
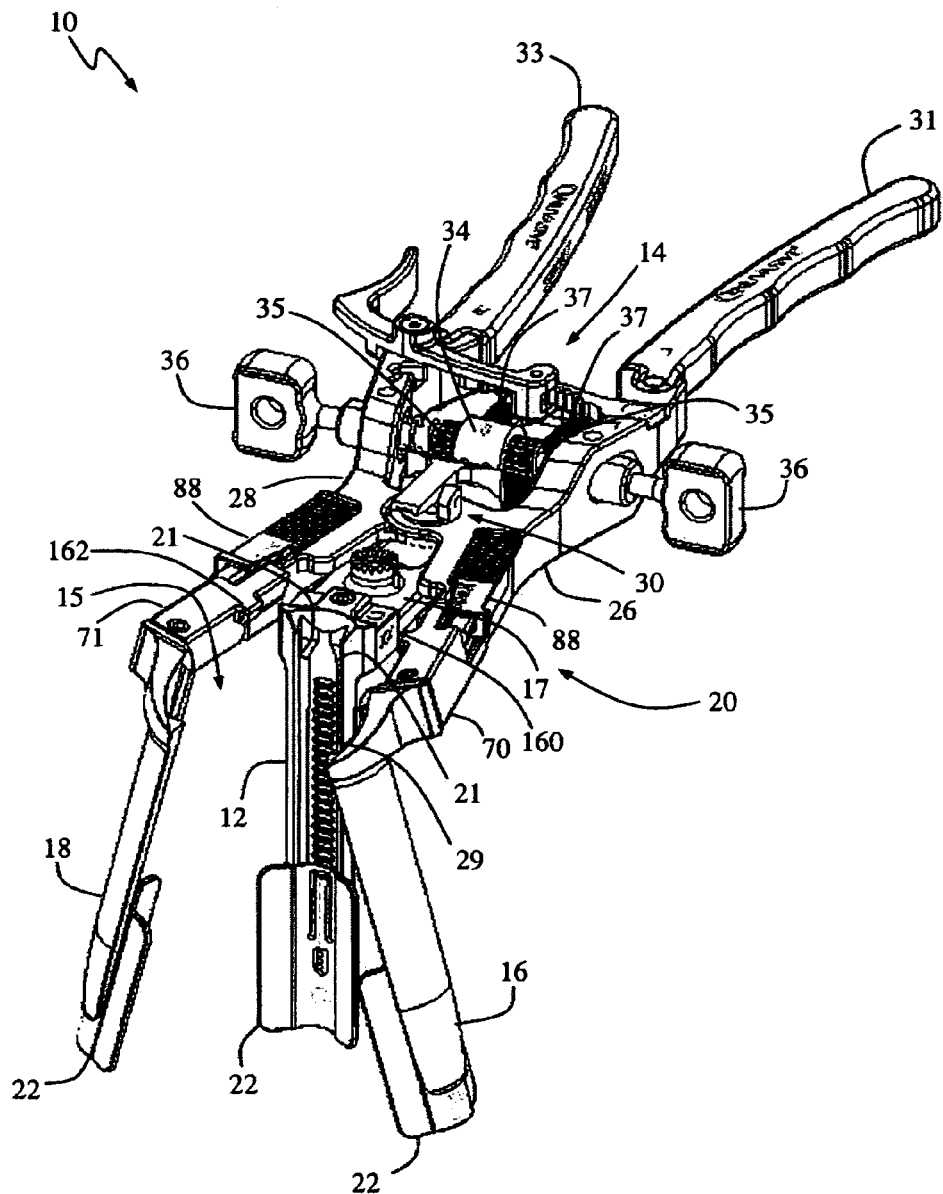
FIG. 1 is a perspective view of a tissue retraction assembly forming part of a surgical access system according to the present invention, shown in a fully retracted or "open" position.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. It is furthermore to be readily understood that, although discussed below primarily within the context of spinal surgery, the surgical access system of the present invention may be employed in any number of anatomical settings to provide access to any number of different surgical target sites throughout the body. It is also expressly noted that, although shown and described herein largely within the context of lateral surgery in the lumbar spine, the access system of the present invention may be employed in any number of other spine surgery access approaches, including but not limited to posterior, postero-lateral, anterior, and antero-lateral access, and may be employed in the lumbar, thoracic and/or cervical spine, all without departing from the present invention. The surgical access system disclosed herein boasts a variety of inventive features and components that warrant patent protection, both individually and in combination.

The present invention involves accessing a surgical target site in a fashion less invasive than traditional "open" surgeries and doing so in a manner that provides access in spite of the neural structures required to be passed through (or near) in order to establish an operative corridor to the surgical target site. Generally speaking, the surgical access system of the present invention accomplishes this by providing a tissue distraction assembly and a tissue retraction assembly, both of which may be equipped with one or more electrodes for use in detecting the existence of (and optionally the distance and/or direction to) neural structures.

These electrodes are preferably provided for use with a nerve surveillance system such as, by way of example, the type shown and described in. Generally speaking, this nerve surveillance system is capable of detecting the existence of (and optionally the distance and/or direction to) neural structures during the distraction and retraction of tissue by detecting the presence of nerves by applying a stimulation signal to such instruments and monitoring the evoked EMG signals from the myotomes associated with the nerves being passed by the distraction and retraction systems of the present invention. In so doing, the system as a whole (including the surgical access system of the present invention) may be used to form an operative corridor through (or near) any of a variety of tissues having such neural structures, particularly those which, if contacted or impinged, may otherwise result in neural impairment for the patient. In this fashion, the access system of the present invention may be used to traverse tissue that would ordinarily be deemed unsafe or undesirable, thereby broadening the number of manners in which a given surgical target site may be accessed.

The tissue distraction assembly of the present invention (comprising a K-wire, an initial dilator, and a plurality of sequentially dilating cannulae) is employed to distract the tissues extending between the skin of the patient and a given surgical target site (preferably along the posterior region of the target intervertebral disc). Once distracted, the resulting void or distracted region within the patient is of sufficient size to accommodate a tissue retraction assembly of the present invention. More specifically, the tissue retraction assembly (comprising a plurality of retractor blades extending from a handle assembly) may be advanced relative to the secondary distraction assembly such that the retractor blades, in a first, closed position, are advanced over the exterior of the secondary distraction assembly. At that point, the handle assembly may be operated to move the retractor blades into a second, open or "retracted" position to create an operative corridor to the surgical target site.

According to one aspect of the invention, following (or before) this retraction, a posterior shim element (which is preferably slidably engaged with the posterior retractor blade) may be advanced such that a distal shim extension in positioned within the posterior region of the disc space. If done before retraction, this helps ensure that the posterior retractor blade will not move posteriorly during the retraction process, even though the other retractor blades (e.g. cephalad-most and caudal-most) are able to move and thereby create an operative corridor. Fixing the posterior retractor blade in this fashion serves several important functions. First, the distal end of the shim element serves to distract the adjacent vertebral bodies, thereby restoring disc height. It also rigidly couples the posterior retractor blade in fixed relation relative to the vertebral bodies. The posterior shim element also helps ensure that surgical instruments employed within the operative corridor are incapable of being advanced outside the operative corridor, preventing inadvertent contact with the exiting nerve roots during the surgery. Once in the appropriate retracted state, the cephalad-most and caudal-most retractor blades may be locked in position and, thereafter, retractor extenders advanced therealong to prevent the ingress or egress of instruments or biological structures (e.g. nerves, vasculature, organs, etc. . . . ) into or out of the operative corridor. Optionally, the cephalad-most and/or caudal-most retractor blades may be pivoted in an outward direction to further expand the operative corridor. Once the operative corridor is established, any of a variety of surgical instruments, devices, or implants may be passed through and/or manipulated within the operative corridor depending upon the given surgical procedure.

Figure 2:
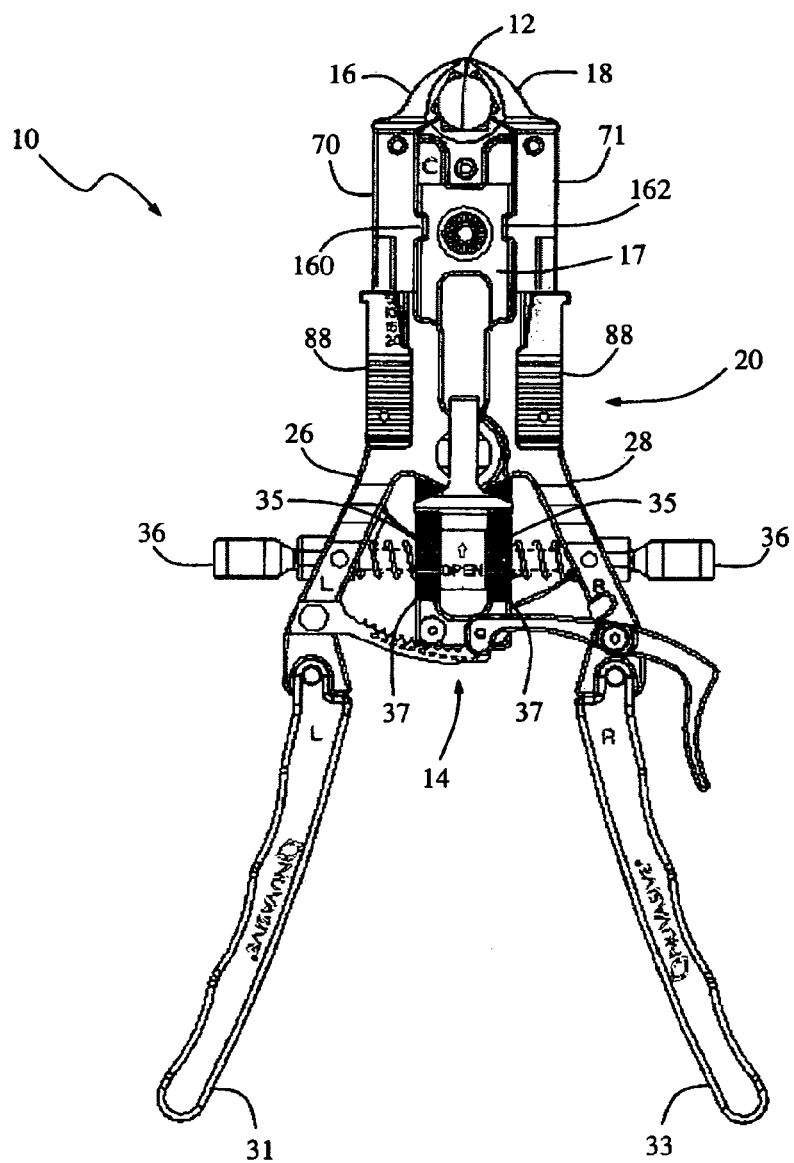
FIGS. 2-3 are top and perspective views, respectively, of the tissue retraction assembly of FIG. 1 shown in a closed position according to the present invention.
Figure 3:
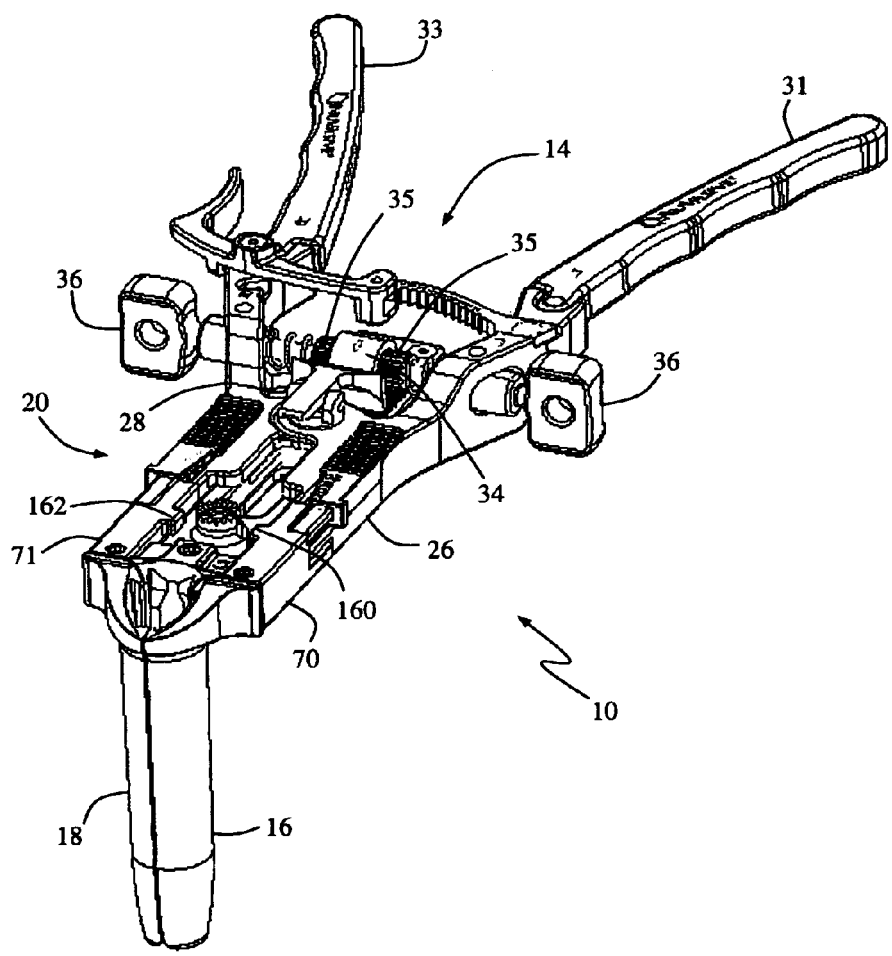
Figure 4:
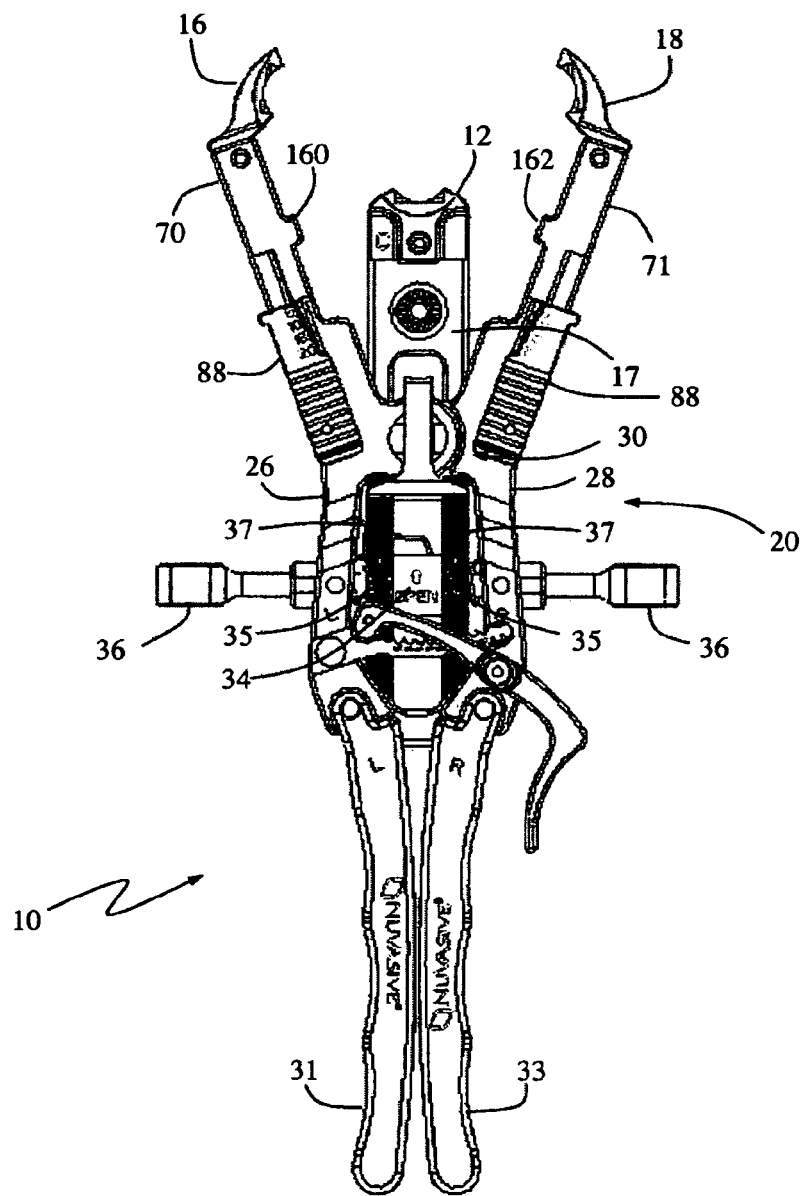
FIGS. 4-5 are top and perspective views, respectively, of the tissue retraction assembly of FIG. 1 in an open position.
Figure 5:
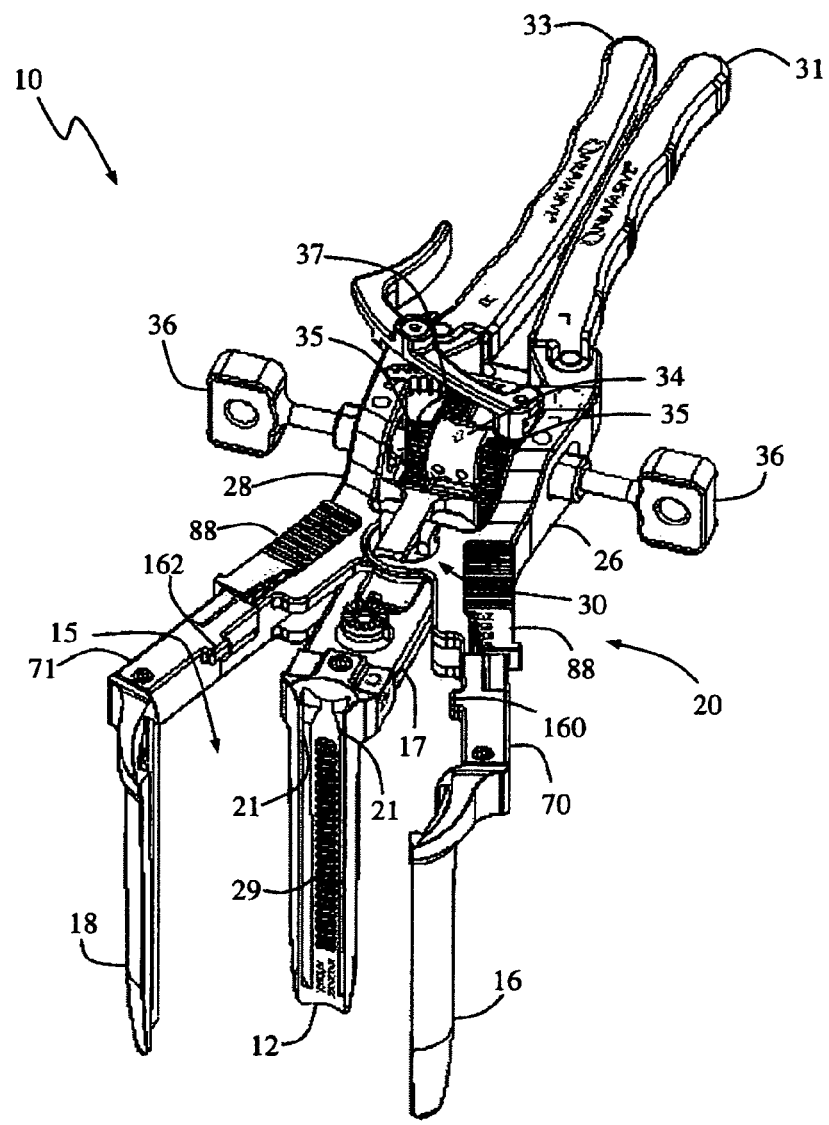

FIGS. 1-5 illustrate a tissue retraction assembly 10 forming part of a surgical access system according to the present invention, including a plurality of retractor blades extending from a handle assembly 20. By way of example only, the handle assembly 20 is provided with a first retractor blade 12, a second retractor blade 16, and a third retractor blade 18. FIG. 1 illustrates the retractor assembly 10 in a fully retracted or "open" configuration, with the retractor blades 12, 16, 18 positioned a distance from one another so as to form an operative corridor 15 therebetween which extends to a surgical target site (e.g. an annulus of an intervertebral disc). In an important aspect of the present invention, the blades 16, 18 are capable of being pivoted or rotated relative to the handle 20, as best appreciated with combined reference to FIGS. 1 and 4-5. FIGS. 2-3 show the retractor assembly 10 in an initial "closed" configuration, with the retractor blades 12, 16, 18 in a generally abutting relation to one another. Although shown and described below with regard to the three-bladed configuration, it is to be readily appreciated that the number of retractor blades may be increased or decreased without departing from the scope of the present invention. Moreover, although described and shown herein with reference to a generally lateral approach to a spinal surgical target site (with the first blade 12 being the "posterior" blade, the second blade 16 being the "cephalad-most" blade, and the third blade 18 being the "caudal-most" blade), it will be appreciated that the retractor assembly 10 of the present invention may find use in any number of different surgical approaches, including generally posterior, generally postero-lateral, generally anterior and generally antero-lateral.

The retractor blades 12, 16, 18 may be composed of any material suitable for introduction into the human body, including but not limited to aluminum, titanium, and/or clear polycarbonate, that would ensure rigidity during tissue distraction. The retractor blades 12, 16, 18 may be optionally coated with a carbon fiber reinforced coating to increase strength and durability. The blades 12, 16, 18 may be optionally constructed from partially or wholly radiolucent materials (e.g. aluminum, PEEK, carbon-fiber, and titanium) to improve the visibility of the surgeon during imaging (e.g. radiographic, MRI, CT, fluoroscope, etc. . . . ). The retractor blades 12, 14, 18 may also be composed of a material that would destruct when autoclaved (such as polymer containing a portion of glass particles), which may be advantageous in preventing the unauthorized re-use of the blades 12, 16, 18 (which would be provided to the user in a sterile state). The retractor blades 12, 16, 18 may be provided in any number of suitable lengths, depending upon the anatomical environment and surgical approach, such as (by way of example only) the range from 20 mm to 150 mm. Based on this range of sizes, the tissue retraction assembly 10 of the present invention is extremely versatile and may be employed in any of a variety of desired surgical approaches, including but not limited to lateral, posterior, postero-lateral, anterior, and antero-lateral, by simply selecting the desired size retractor blades 12, 16, 18 and attaching them to the handle assembly 20 as will be described herein.

Figure 6:
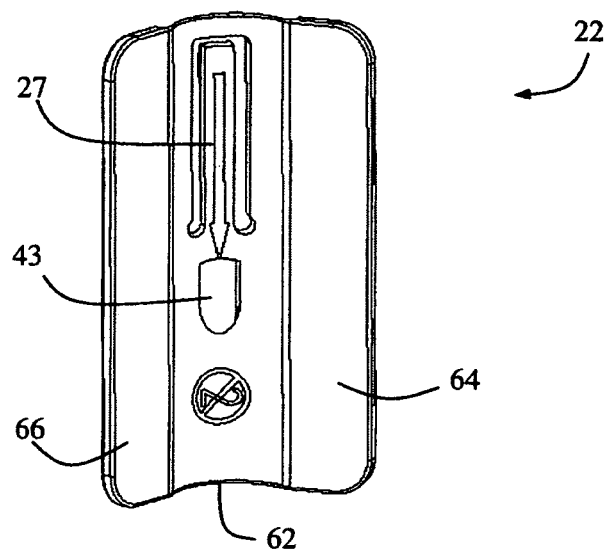
FIGS. 6-7 are perspective views illustrating the front and back of a wide retractor extender for use with any one of the retractor blades according to the retractor of the present invention.
Figure 7:
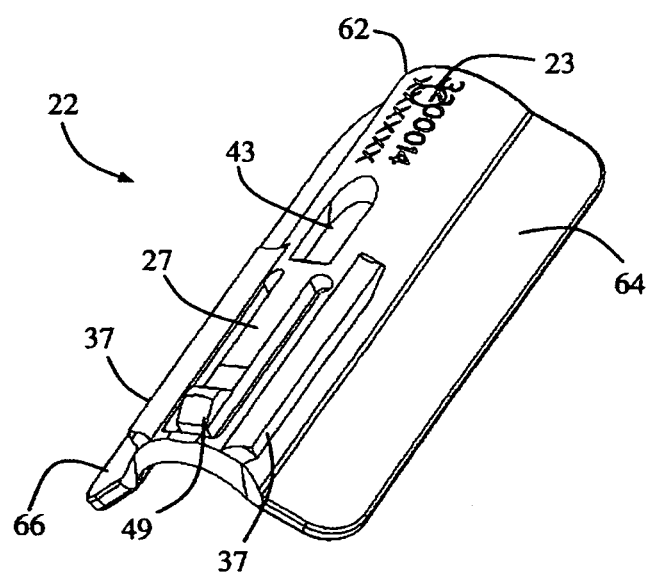
Figure 8:
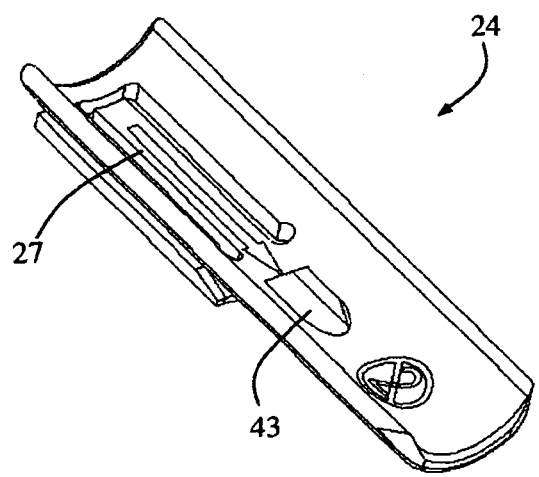
FIGS. 8-9 are perspective views illustrating the front and back of a narrow retractor extender for use with one of the retractor blades according to the retractor of the present invention.
Figure 9:
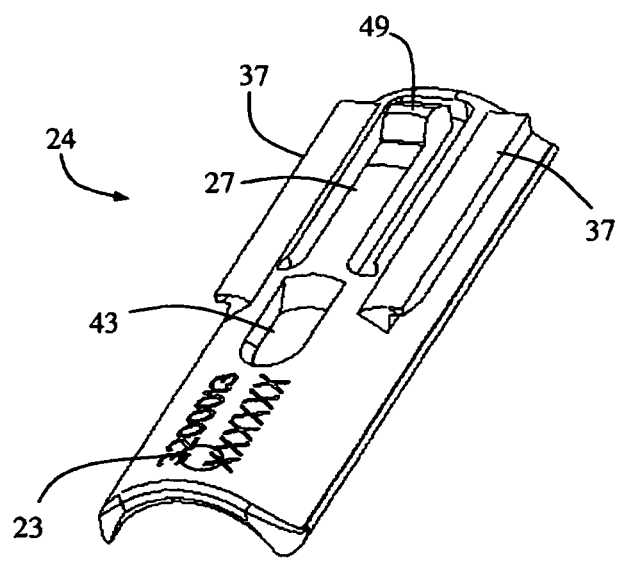
Figure 10:
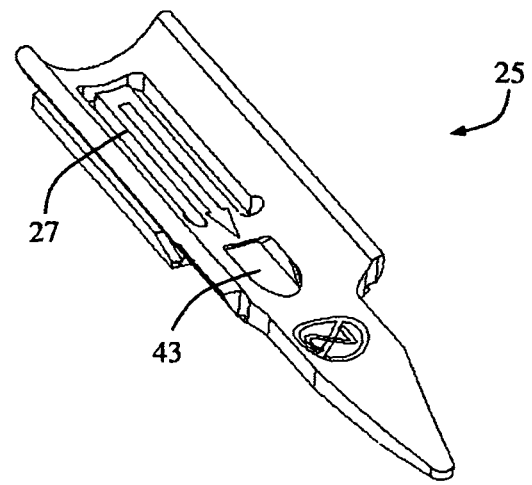
FIGS. 10-11 are perspective views illustrating the front and back of a shim element for use with a posterior retractor blade of the retractor according to the retractor of the present invention.
Figure 11:
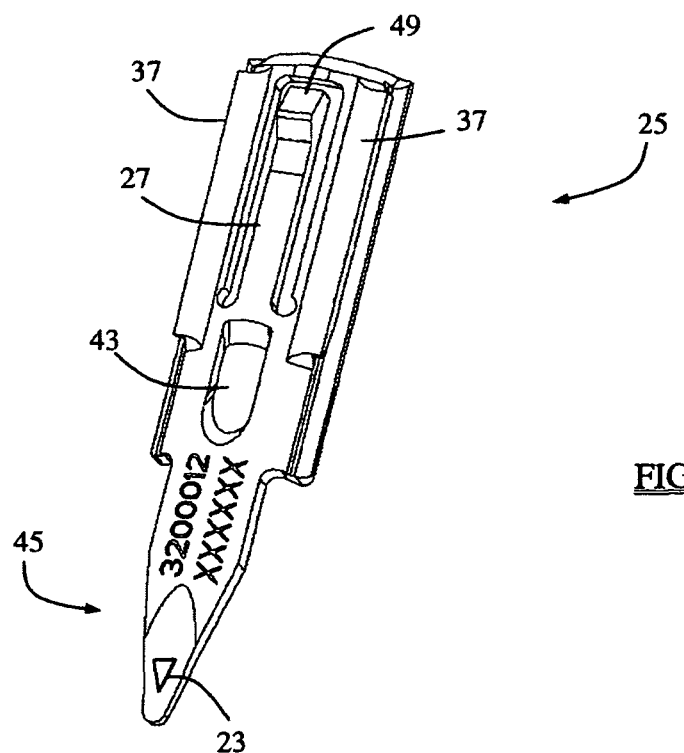
Figure 12:
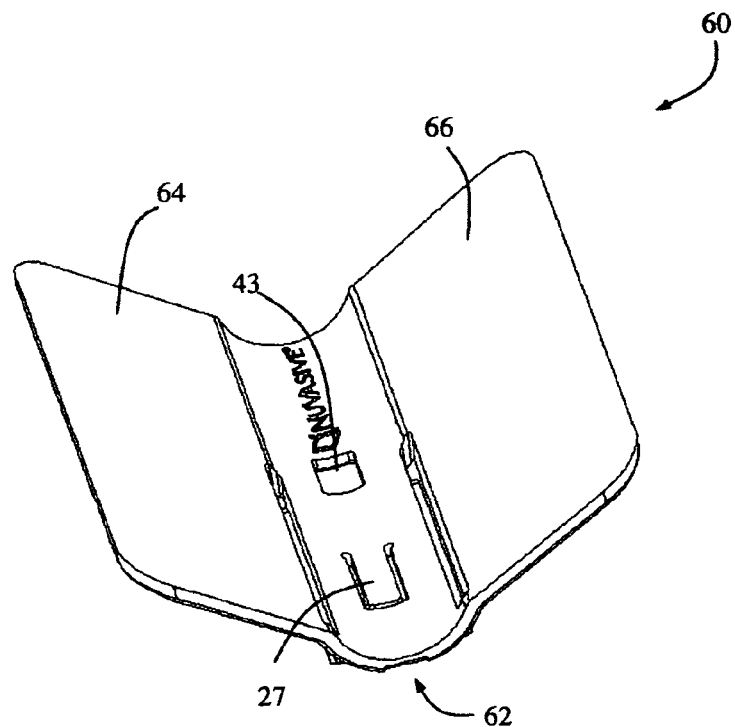
FIGS. 12-13 are perspective views of the front and back, respectively, of a shim element according to one embodiment of the present invention.
Figure 13:
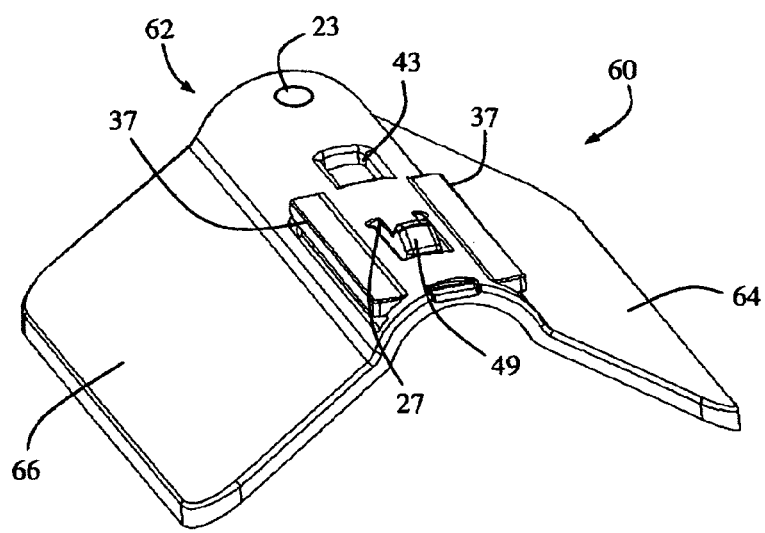
Figure 14:
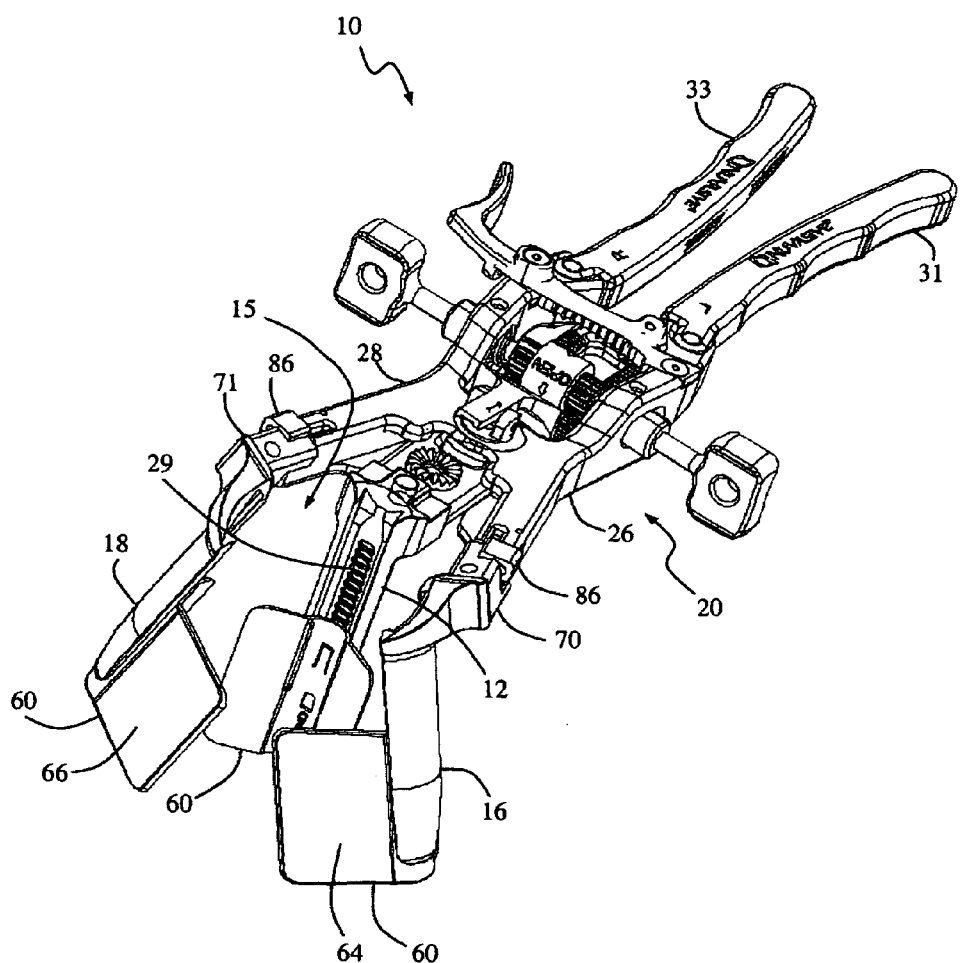
FIGS. 14-15 are perspective and top views, respectively, of a tissue retraction assembly of according to one embodiment of the present invention, shown in an open position with a shim and/or retractor extender installed on each retractor blade.
Figure 15:
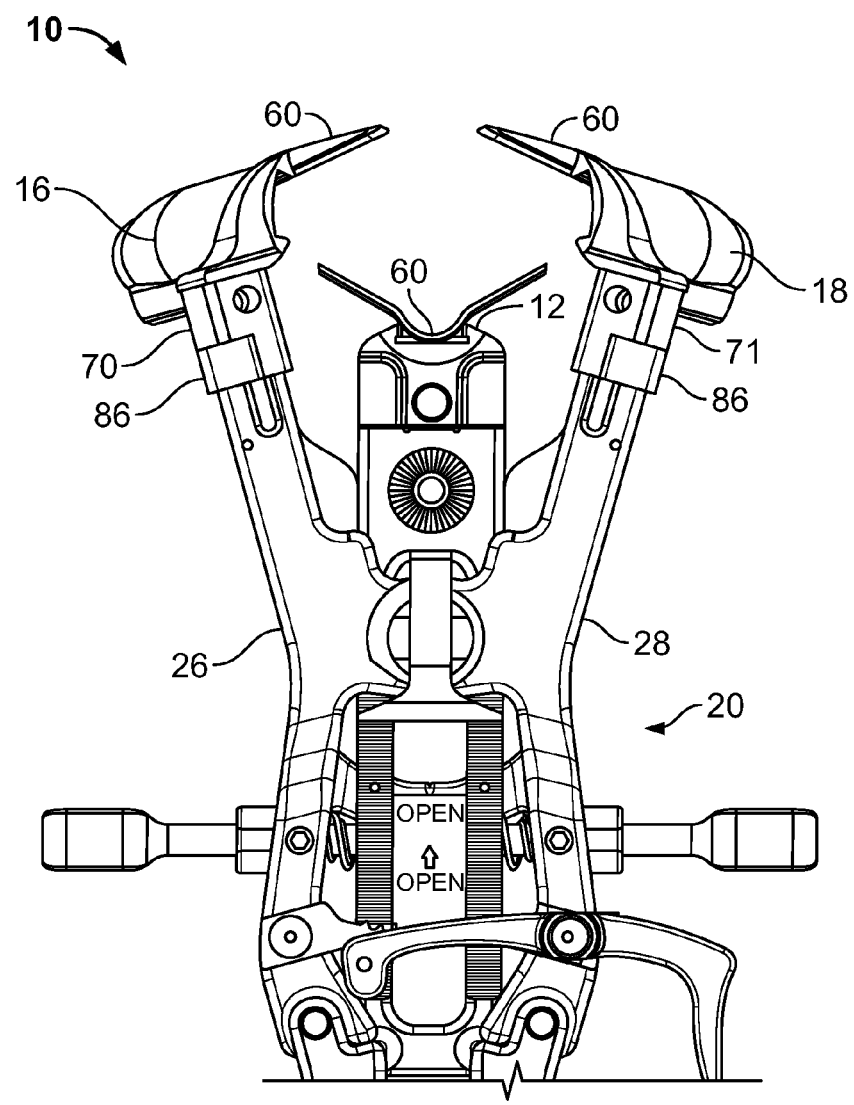

The retractor blades 12, 16, 18 may be equipped with various additional features or components. By way of example only, one or more of the retractor blades 12, 16, 18 may be equipped with a retractor extender, such as a wide retractor extender 22 as shown in FIGS. 6-7, a narrow retractor extender 24 as shown in FIGS. 8-9 and/or an extra wide retractor extender 60 as shown in FIGS. 12-13. The retractor extenders 22, 24, 60 extend from the retractor blades 12, 16, 18 (as shown in FIGS. 14-15, by way of example, with reference to retractor extender 60) to form a protective barrier to prevent the ingress or egress of instruments or biological structures (e.g. nerves, vasculature, organs, etc. . . . ) into or out of the operative corridor 15. Depending upon the anatomical setting and surgical approach, one or more of the retractor blades 12, 16, 18 may be equipped with a shim element 25 as shown in FIGS. 10-11. Shim element 25 has a distal tapered region 45 which may be advanced into tissue (e.g. bone, soft tissue, etc. . . . ) for the purpose of anchoring the blades 12, 16, 18 and/or advanced into the disc space to distract the adjacent vertebral bodies (thereby restoring disc height). In similar fashion to the retractor extenders 22, 24, 60, the shim element 25 also forms a protective barrier to prevent the ingress or egress of instruments or biological structures (e.g. nerves, vasculature, etc. . . . ) into or out of the operative corridor 15.

Retractor extenders 22, 24, 60 and/or shim element 25 may be made out any material suitable for use in the human body, including but not limited to biologically compatible plastic and/or metal, preferably partially or wholly radiolucent in nature material (such as aluminum, PEEK, carbon-fibers and titanium). Construction from plastic or thin metal provides the additional benefit of allowing the shim 25 and/or retractor extenders 22, 24, 60 to be collapsed into a compressed or low profile configuration at the skin level as the element is inserted, and then expanded once it is below skin level and within the operative corridor 15. Retractor extenders 22, 24, 60 may have symmetric narrow configurations (FIGS. 8-9) and/or broad configurations (FIGS. 6-7 and 12-13) and/or an asymmetric configuration of narrow and broad elements (FIGS. 14-15). For example, any or all of the retractor extenders 22, 24, 60 may be provided with a lateral section 64 of the type shown in FIGS. 6-7, a narrow configuration (without lateral sections 64, 66) of the type shown in FIGS. 8-9, and/or a lateral section 66 of the type shown in FIGS. 12-13, all without departing from the scope of the present invention. The retractor extenders 22, 24, 60 and/or the shim element 25 may be composed of a material that would destruct when autoclaved (such as polymer containing a portion of glass particles), which may be advantageous in preventing the unauthorized re-use of the retractor extenders 22, 24, 60 and/or the shim element 25 (which would be provided to the user in a sterile state). Slits may also be provided on the shim 25 to improve flexibility. The retractor extenders 22, 24, 60 and/or the shim element 25 may have a parabolic concave curvature in addition to the configuration shown by way of example only in FIGS. 12-13.

Each of the retractor extenders 22, 24, 60 and/or the shim element 25 may be equipped with a mechanism to selectively and releasably engage with the respective retractor blades 12, 16, 18. By way of example only, this may be accomplished by configuring the retractor extenders 22, 24, 60 and/or the shim element 25 with a tab element 27 capable of engaging with corresponding ratchet-like grooves (shown at 29 in FIG. 1) along the inner-facing surfaces of the retractor blades 12, 16, 18. Each of the retractor extenders 22, 24, 60 and/or the shim element 25 is provided with a pair of engagement elements 37 having, by way of example only, a generally dove-tailed cross-sectional shape. The engagement elements 37 are dimensioned to engage with receiving portions 21 on the respective retractor blades 12, 16, 18. In a preferred embodiment, each of the retractor extenders 22, 24, 60 and/or the shim element 25 may be provided with an elongate slot 43 for engagement with an insertion tool 140 of the type shown in FIGS. 34-37 (as will be described in greater detail below). Each tab member 27 is also equipped with an enlarged tooth element 49 which engages within corresponding grooves 29 provided along the inner surface of the retractor blades 12, 16, 18. On the wide and extra wide retractor extenders 22, 60, respectively, each includes a center portion 62 flanked by a pair of lateral sections 64, 66, which effectively increase the width of the retractor blades 12, 16, 18.

According to the present invention, any or all of the retractor blades 12, 16, 18, the retractor extenders 22, 24, 60, and/or the shim element 25 may be provided with one or more electrodes 23 (preferably at or near their distal regions) equipped for use with a nerve surveillance system, such as, by way of example, the type shown and described in Int'l Patent App. Ser. No. PCT/US02/30617 filed on Sep. 25, 2002, and Int'l Patent App. Ser. No. PCT/US2008/004427, filed Apr. 3, 2008 ("Neurophysiology Monitoring Patents") the entire contents of which are each expressly incorporated by reference herein. Such a nerve surveillance system is capable of detecting the existence of (and optionally the distance and/or direction to) neural structures during the retraction of tissue by detecting the presence of nerves by applying a stimulation signal to electrodes 23 and monitoring the evoked EMG signals from the myotomes associated with the nerves in the vicinity of the retraction system 10 of the present invention. In so doing, the system as a whole (including the surgical retraction system 10 of the present invention) may be used to form an operative corridor through (or near) any of a variety of tissues having such neural structures, particularly those which, if contacted or impinged, may otherwise result in neural impairment for the patient. In this fashion, the access system of the present invention may be used to traverse tissue that would ordinarily be deemed unsafe or undesirable, thereby broadening the number of manners in which a given surgical target site may be accessed.

With reference to FIGS. 1-5, the handle assembly 20 may be coupled to any number of mechanisms for rigidly registering the handle assembly 20 in fixed relation to the operative site, such as through the use of an articulating arm mounted to the operating table (not shown). The handle assembly 20 includes first and second arm members 26, 28 hingedly coupled via coupling mechanism shown generally at 30. The second retractor blade 16 is rigidly coupled (generally perpendicularly) to the end of the first arm member 26. The third retractor blade 18 is rigidly coupled (generally perpendicularly) to the end of the second arm member 28. The first retractor blade 12 is rigidly coupled (generally perpendicularly to) a translating member 17, which is coupled to the handle assembly 20 via a linkage assembly shown generally at 14. The linkage assembly 14 includes a roller member 34 having a pair of manual knob members 36 which, when rotated via manual actuation by a user, causes teeth 35 on the roller member 34 to engage within ratchet-like grooves 37 in the translating member 17. Thus, manual operation of the knobs 36 causes the translating member 17 to move relative to the first and second arm members 26, 28.

Through the use of handle extenders 31, 33, the arms 26, 28 may be simultaneously opened such that the second and third retractor blades 16, 18 move away from one another. In this fashion, the dimension and/or shape of the operative corridor 15 may be tailored depending upon the degree to which the translating member 17 is manipulated relative to the arms 26, 28. That is, the operative corridor 15 may be tailored to provide any number of suitable cross-sectional shapes, including but not limited to a generally circular cross-section, a generally ellipsoidal cross-section, and/or an oval cross-section. Optional light emitting devices (not shown) may be coupled to one or more of the retractor blades 12, 16, 18 to direct light down the operative corridor 15.

Figure 16:
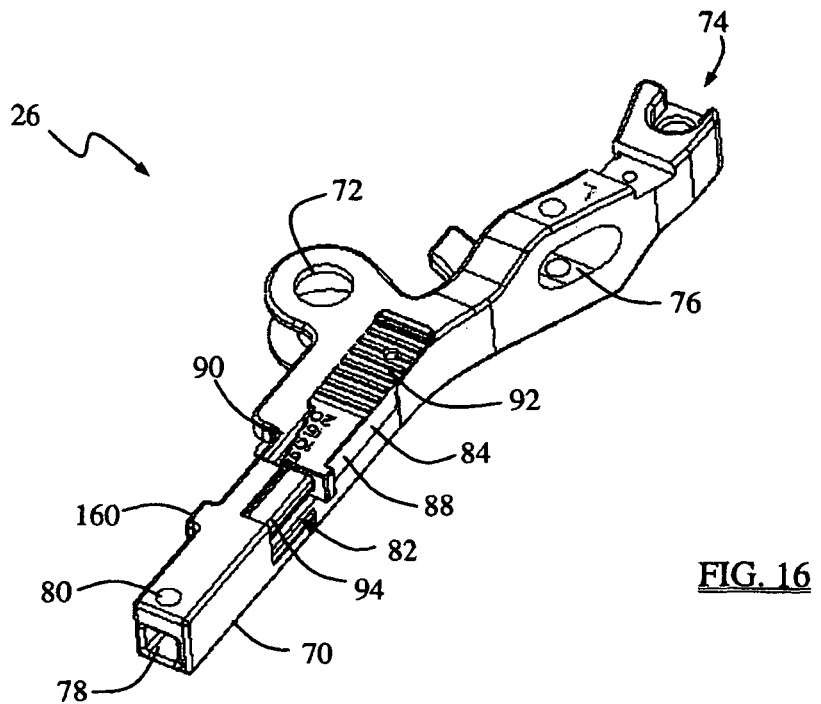
FIGS. 16-17 are perspective views of an arm member comprising part of the tissue retraction assembly of FIG. 1.
Figure 17:
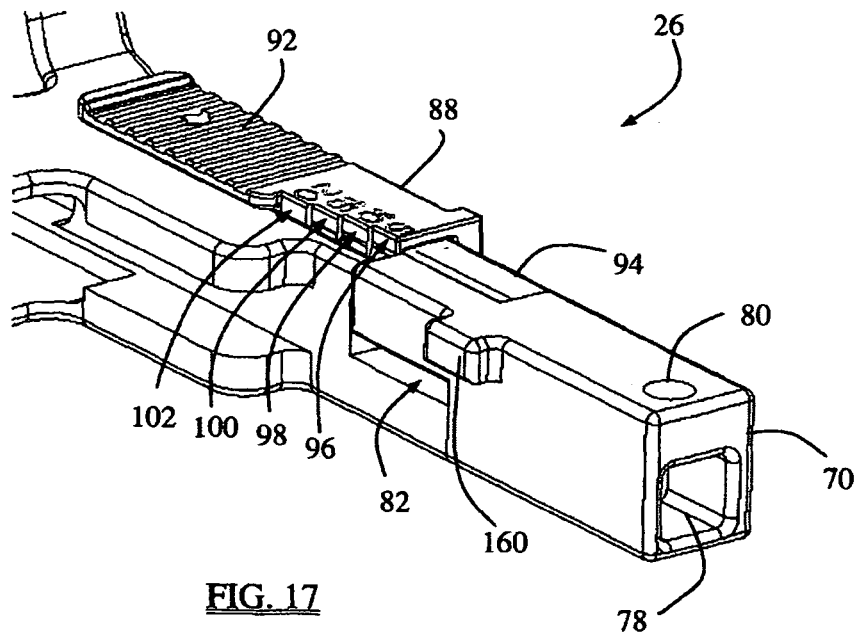
Figure 18:
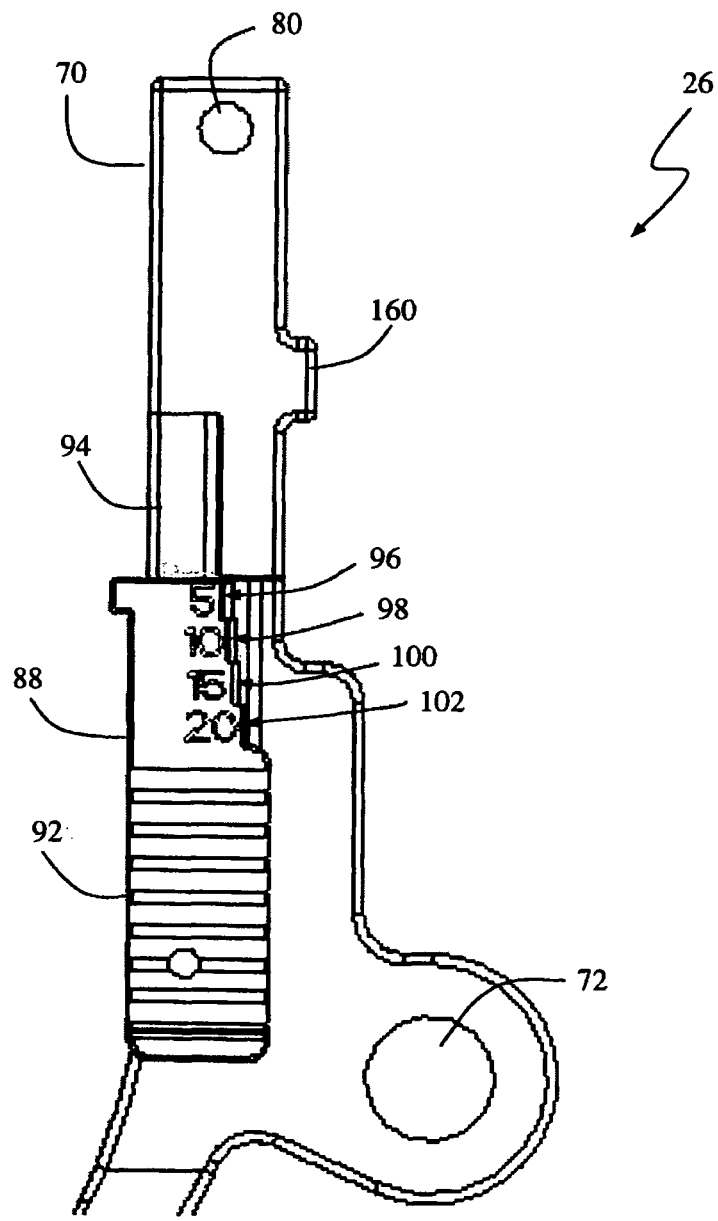
FIG. 18 is a top view of the arm member of FIG. 16.

FIGS. 16-18 illustrate the first arm member 26 in greater detail. First arm member 26 includes a distal pivot member 70, a coupling aperture 72, a proximal region 74 at which handle extender 31 may be attached, an aperture 76 through which knob 36 passes, and a slidable locking mechanism 84 (which may include a single-step lock 86 shown by way of example in FIGS. 14-15 and/or a variable-stop lock 88 as shown in FIGS. 16-18 and described by way of example below). The distal pivot member 70 includes a blade aperture 78, an aperture 80, and a cutout region 82. The blade aperture 78 is dimensioned to interact with the proximal region of the retractor blade 16 in a male-female relationship, such that the male end of blade 16 fits into the female blade aperture 78. To rigidly secure blade 16 to retractor arm 26, a pin or screw (not shown) may be inserted into aperture 80.

The variable-stop lock 88 allows the user to control the degree of expansion of the operative corridor 15. Variable-stop lock 88 includes a variable-stop region 90 and a user engagement region 92, and is dimensioned to slidably engage locking bar 94. The variable-stop region 90 may include any number of sequential step-wise cutout regions corresponding to the angulation desired for the retractor blades 16, 18. By way of example only, the variable-stop locking mechanism includes four sequential step-wise cutout regions 96, 98, 100, 102. Each sequential step-wise cutout region 96, 98, 100, 102 may correspond to a distinct degree of angulation of the retractor blades 16, 18 (relative to the "closed" position shown in FIGS. 2-3). By way of example only, sequential step-wise cutout regions 96, 98, 100, 102 may correspond to 5°, 10°, 15° and 20° of angulation, respectively. Each sequential step-wise cutout region 96, 98, 100, 102 is dimensioned to interact with the distal pivot member 70 once the desired degree of angulation is determined. The user engagement region 92 may include a series of ridges 104 or any other suitable friction-causing element to allow a user to manually operate the variable-stop lock 88 (to adjust and/or lock it).

Figure 19:
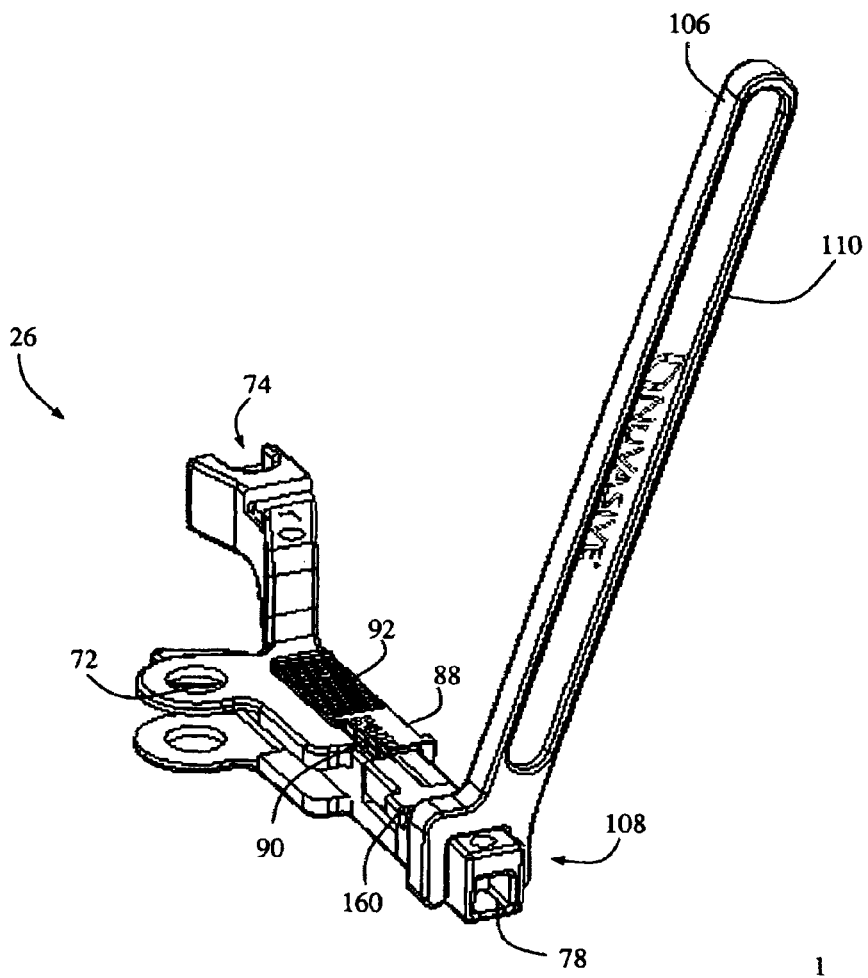
FIGS. 19-20 are perspective and top views, respectively, of the arm member of FIG. 16 in which a pivot wrench is coupled with a distal pivot region of the arm member.
Figure 20:
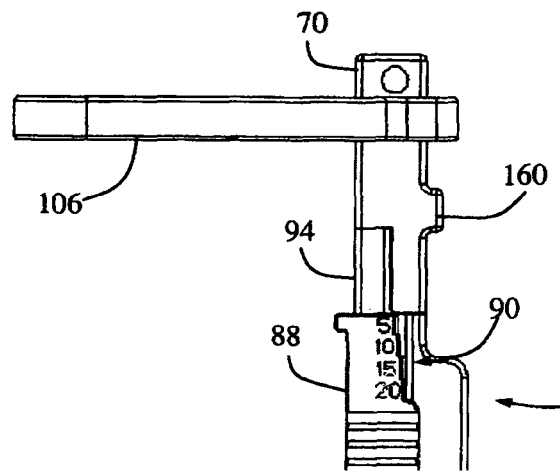
Figure 21:
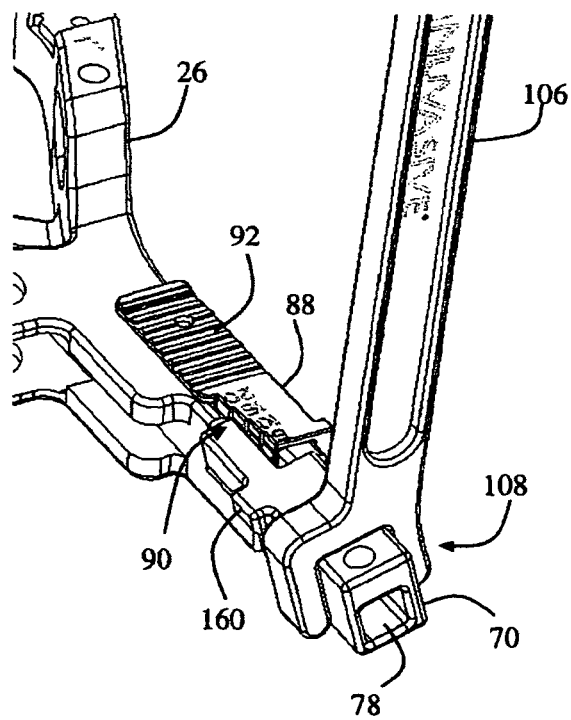
FIG. 21 is a perspective view of the arm member of FIG. 19 after the distal pivot region as been pivoted and the locking mechanism has been engaged.
Figure 22:
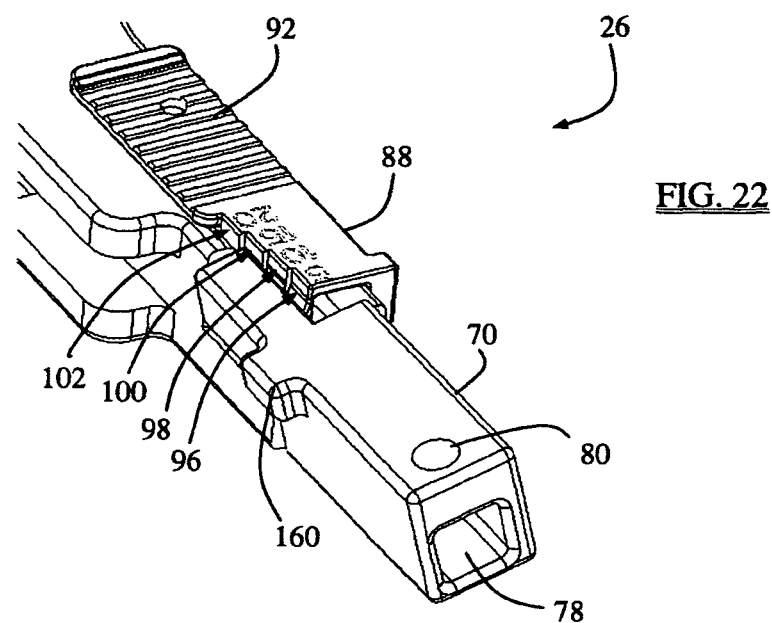
FIGS. 22-23 are perspective and top views, respectively, of the arm member of FIG. 21 in which the pivot wrench has been removed.
Figure 23:
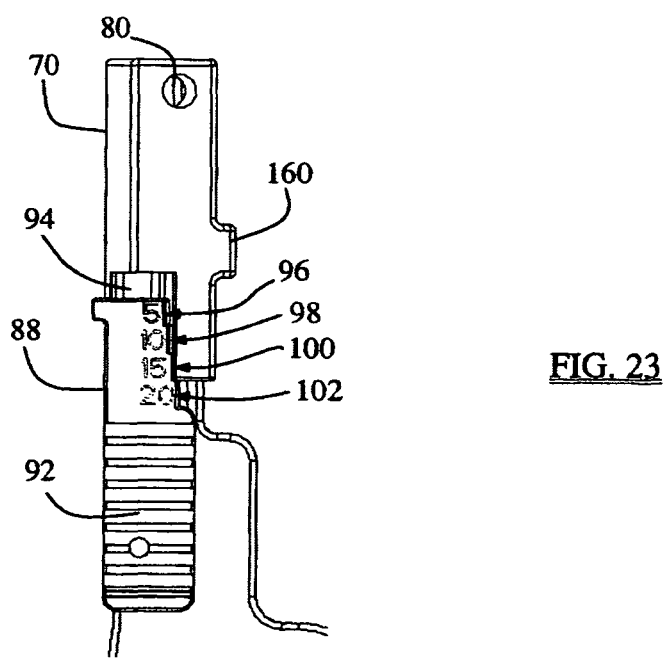
Figure 25:
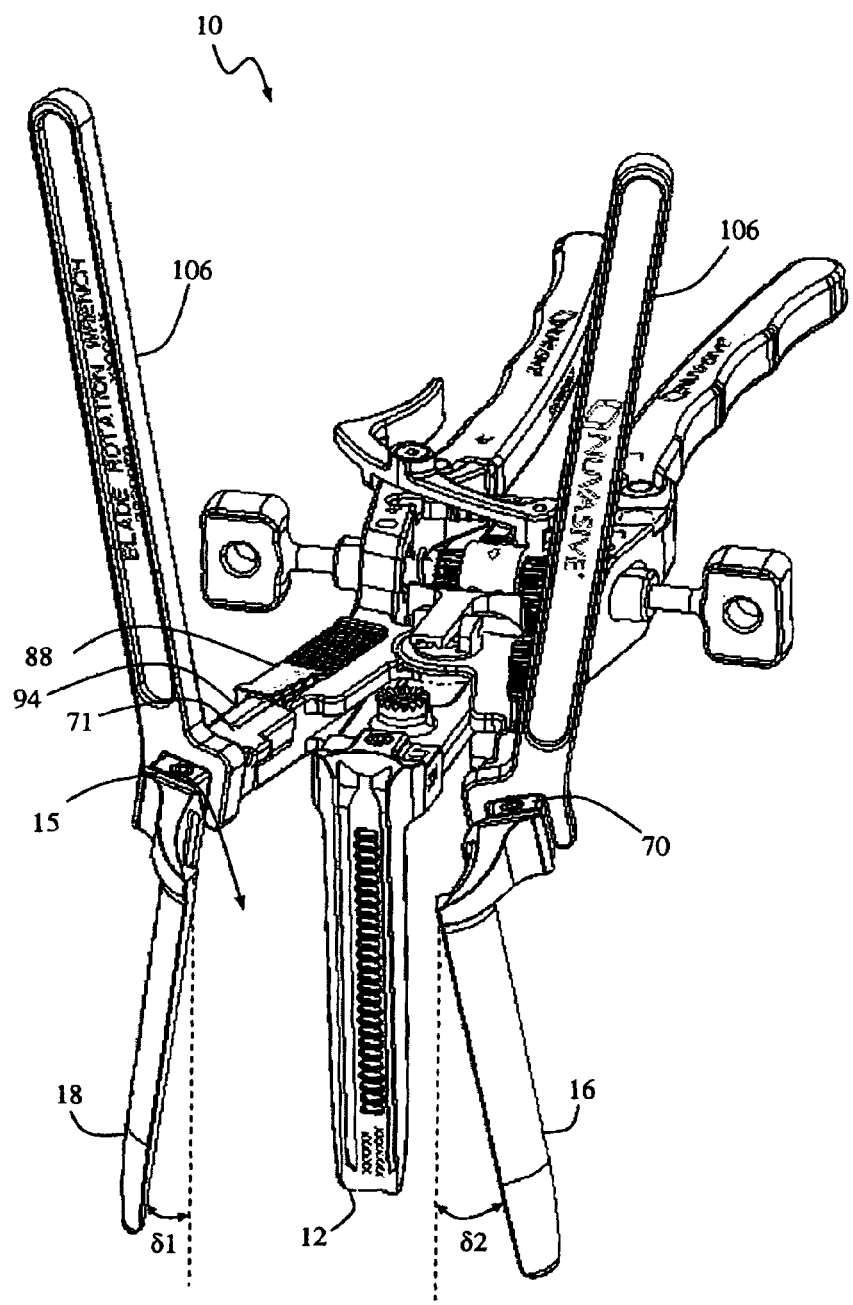
FIG. 25 is a perspective view of the tissue retraction assembly of FIG. 24 after pivoting of the blades.
Figure 26:
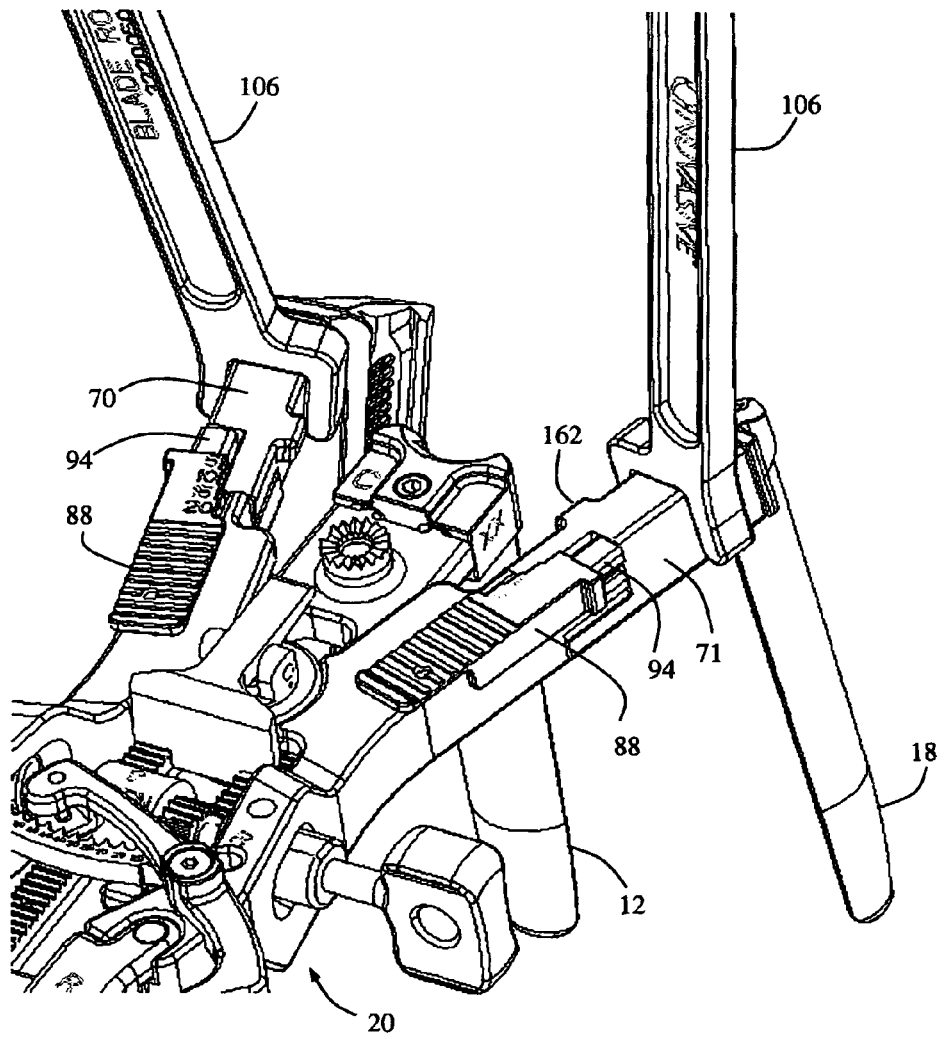
FIG. 26 is a perspective view of the tissue retraction assembly of FIG. 25, in which the locking mechanisms have been activated.
Figure 27:
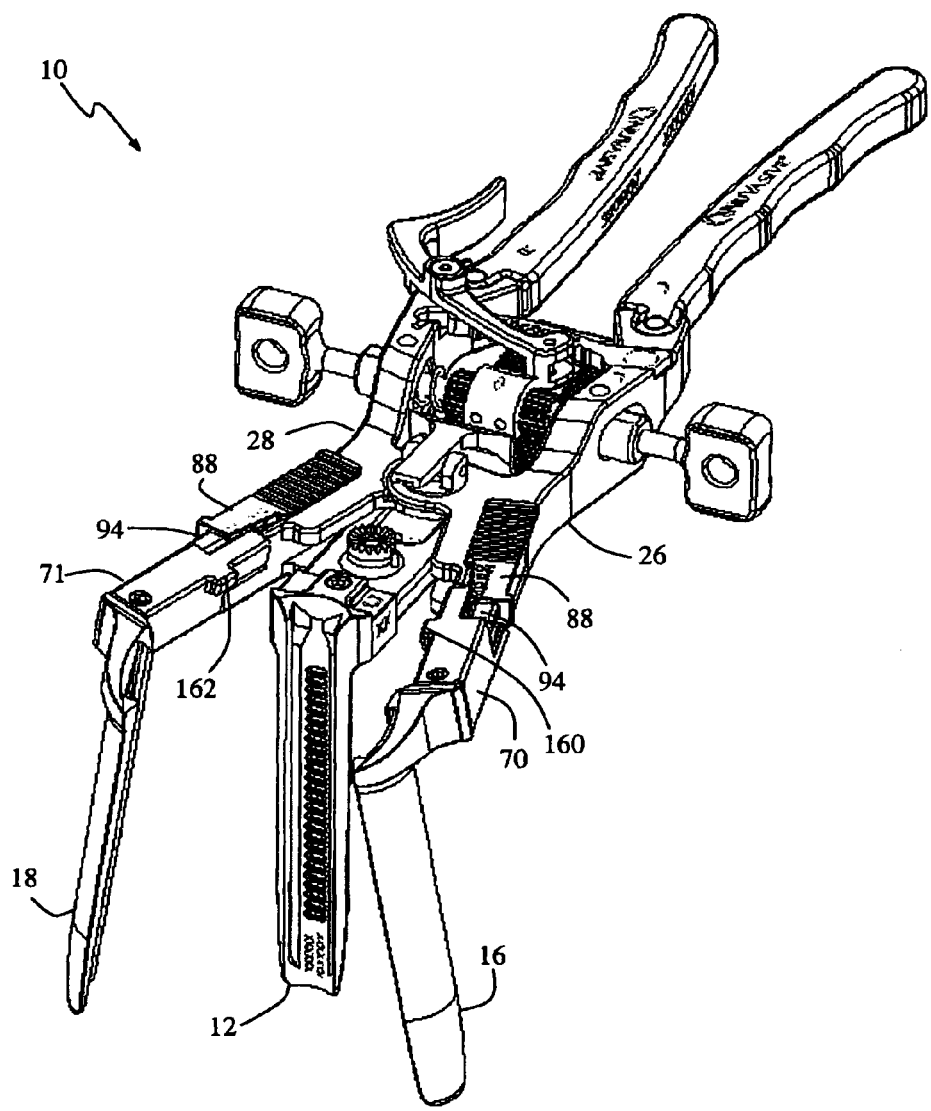
FIGS. 27-28 are perspective and top views, respectively, of the tissue retraction assembly of FIG. 25, in which the cephalad-most and caudal-most blades have been pivoted and the locking mechanisms have been engaged.
Figure 28:
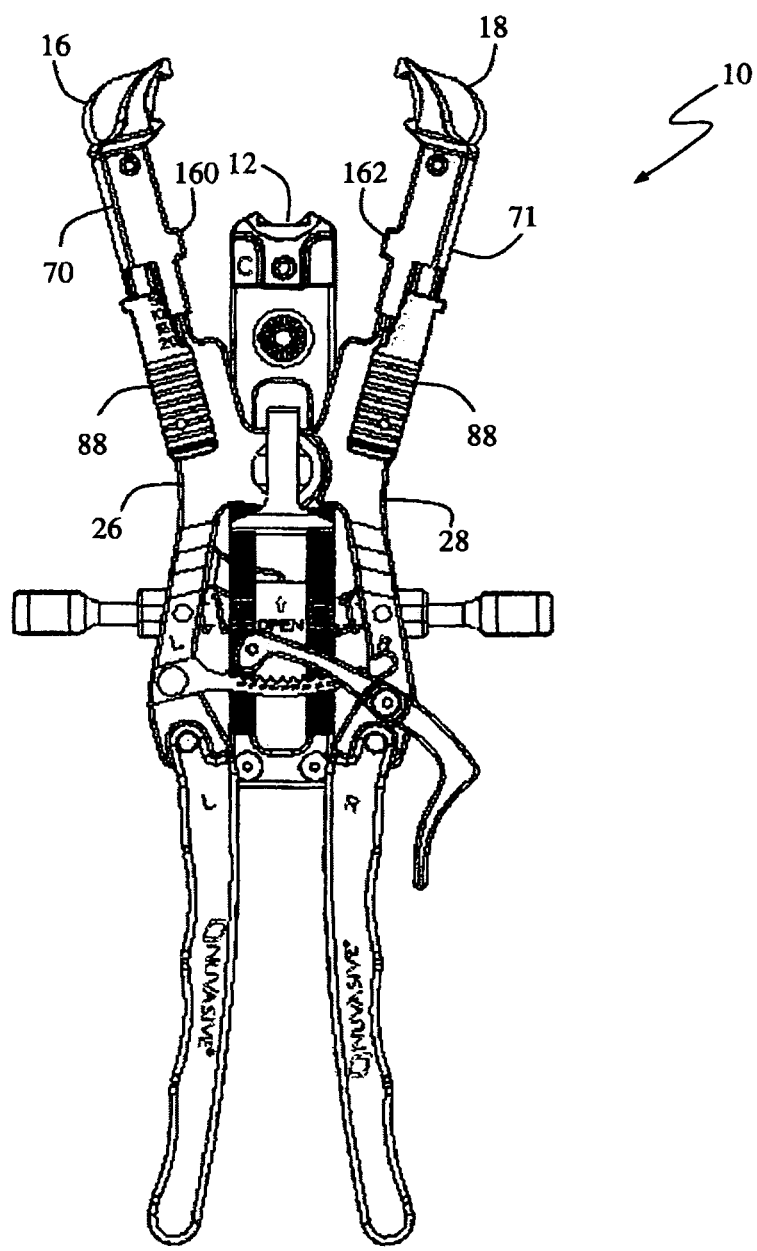
Figure 29:
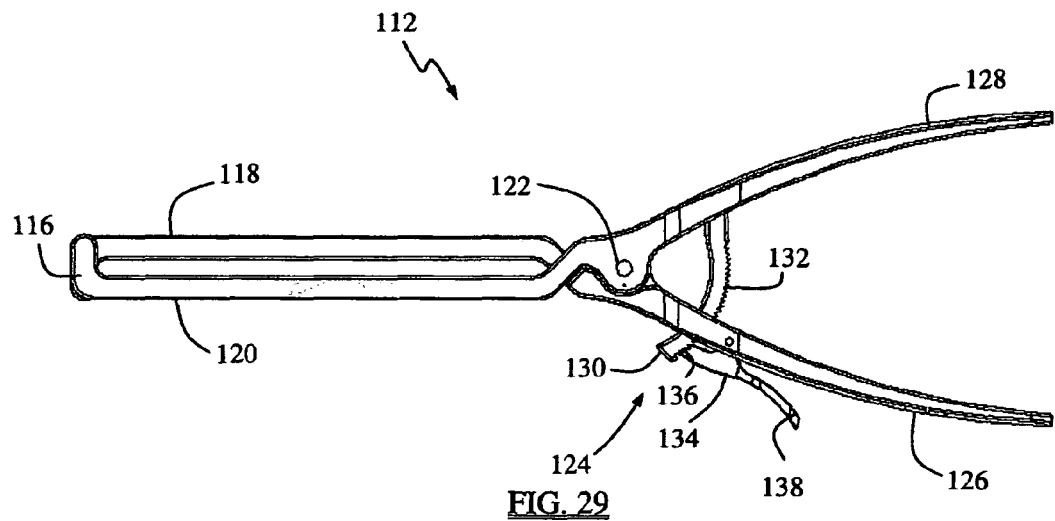
FIGS. 29-30 are side views of a retractor blade expander tool according to one embodiment of the present invention, shown in initial closed and secondary open positions, respectively.
Figure 30:
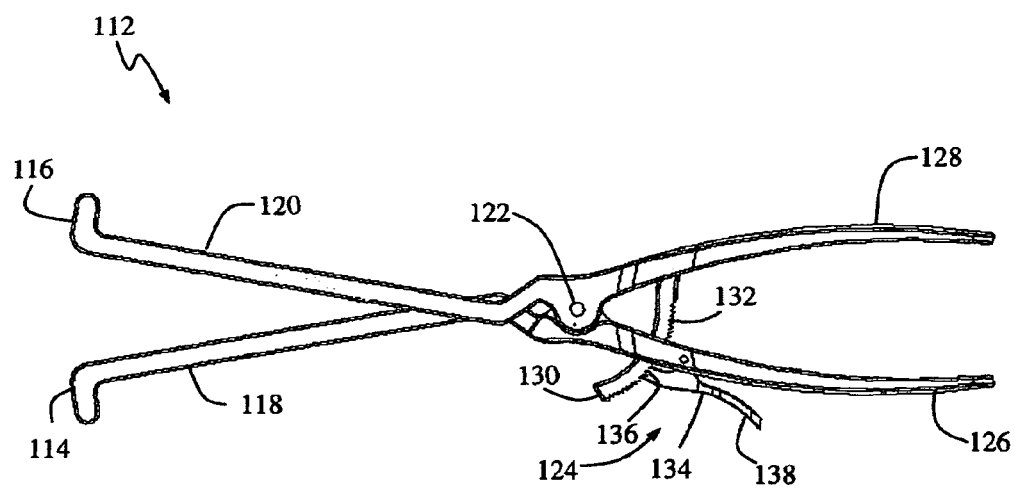

Initially, the retractor assembly 10 of the present invention is introduced to the surgical target site with the retractor blades 12, 16, 18 in a first, closed position (shown generally in FIGS. 2-3). In this configuration, the retractor blades 16, 18 are oriented in a generally perpendicular configuration. In some instances it may be desirable to pivot either the second retractor blade 16 or the third retractor blade 18 (or both) outward in order to increase the volume of the operative corridor 15 (by increasing the distal dimension of the operative corridor). To accomplish this (with respect to blade 16), a pivot wrench 106 is engaged to the distal pivot member 70 of arm 26, as shown in FIGS. 19-21. The pivot wrench 106 includes a gripping portion 108 and a handle 110. The gripping portion 108 is dimensioned to snugly interact with the distal pivot member 70 of arm 26. When the handle 110 is moved in a medial direction (relative to the retractor 10), the blade 16 will pivot in a lateral (outward) direction (FIGS. 21 and 25). Distal pivot member 70 of retractor arm 26 is configured in such a way that it prevents the blade 16 from pivoting in a medial direction. In this manner, the blade 16 may be pivoted to a desired angulation (any angle between 0 and 45 degrees from center, denoted by $\delta 1$ & $\delta 2$ in FIG. 25). While maintaining this desired angulation, the user may engage the user engagement region 92 and exert a force to slide the variable-stop lock 88 in a distal direction along locking bar 94 (FIGS. 22 and 26) until the sequential step-wise cutout region 96, 98, 100, 102 corresponding to the particular angulation engages the distal pivot member 70 of the first arm member 26. By way of example only, if a 5° angulation is desired, cutout region 96 will interact with the distal pivot member 70, preventing further pivoting of the retractor blade 16. On the other hand, if a 15° angulation is desired, the variable-stop lock 88 should be moved along locking bar 94 until cutout region 100 interacts with the distal pivot member 70 (shown by way of example in FIGS. 22-23). After engaging the variable-stop lock 88, the pivot wrench 106 may be removed because the retractor blades 16, 18 are locked into a desired degree of angulation (FIGS. 27-28).

Although described with reference to first arm member 26, it will be appreciated that the detailed features and operation of the present invention as embodied within first arm member 26 are generally applicable (though in a mirror-image orientation) to the second arm member 28. Furthermore, the blade 18 may be pivoted independently of blade 16 such that different angles for each blade 16, 18 are achieved. Thus, it may be desirable to use blades of differing lengths and still maintain a symmetrical operating corridor wherein the distal ends of blades 16, 18 are oriented along the same general plane. Before removing the tissue retraction system 10 from the operative corridor, the variable-stop, lock 88 should be disengaged by sliding it in a proximal direction along locking bar 94, allowing retractor blades 16, 18 to return to an initial alignment to facilitate removal.

As an alternative to the pivot wrench 106, a blade expander 112, such as shown by way of example only in FIGS. 29-33, may be provided to facilitate the manual pivoting of the retractor blades 16, 18. The blade expander 112 may include first and second blade engagement members 114, 116 located on first and second elongated extenders 118, 120, respectively, a pivot joint 122, a locking element 124 and pair of handle extensions 126, 128. By way of example only, the locking element 124 may include a generally curved member 130 including a series of engagement features 132 located along one edge. By way of example only, the engagement features 132 may consist of a series of "teeth" having a generally triangular cross-section. The locking element 124 may further include a release member 134 including a series of engagement features 136 that interact with engagement features 132 to effectively lock the blade expander 112 in a second variable configuration. The release member 134 further includes a manual depressor 138 that, when depressed, causes engagement features 136 to disengage from engagement features 132, allowing blade expander 112 to return from a second configuration to a first configuration.

Figure 31:
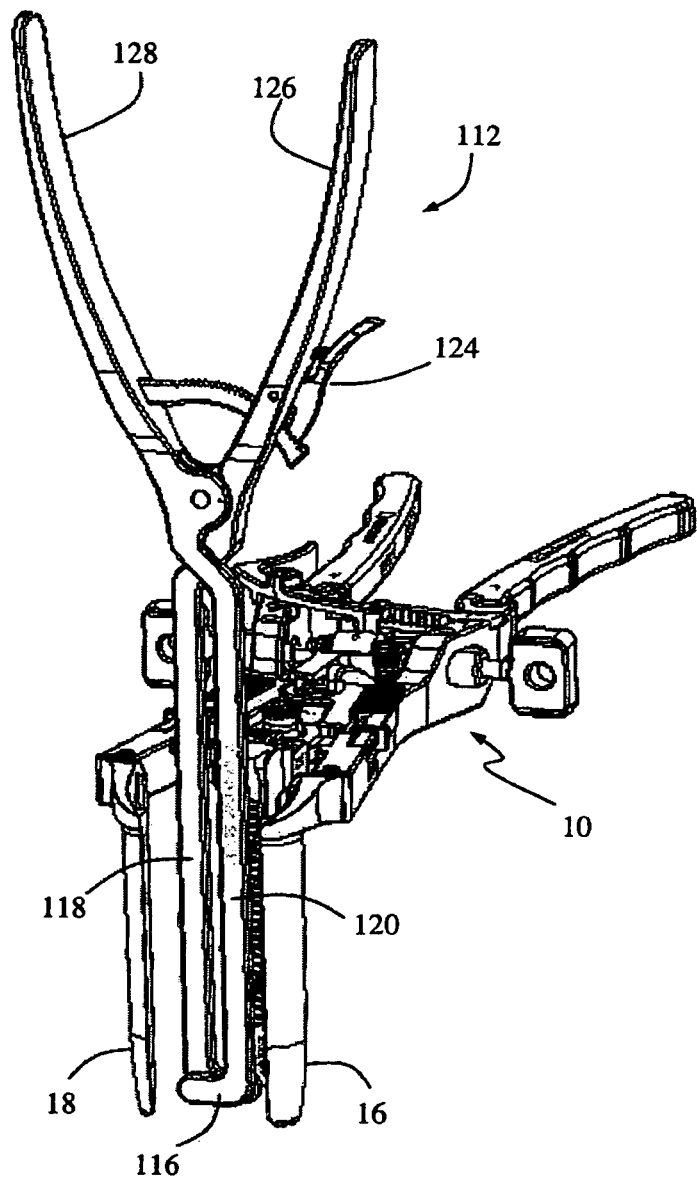
FIG. 31 is a perspective view of a retractor blade expander tool of FIG. 29 inserted into an operative corridor formed by the tissue retraction assembly of FIG. 1 with the blades in a retracted position.
Figure 32:
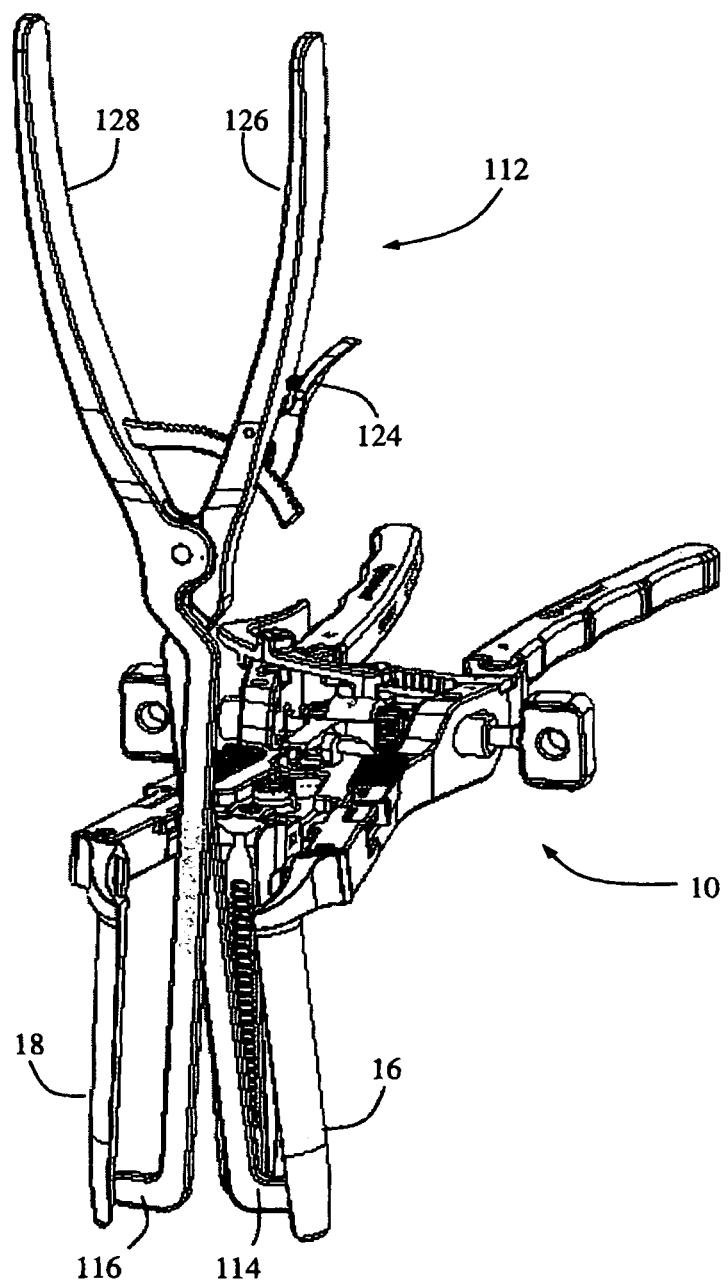
FIGS. 32-33 are perspective views of the retractor blade expander tool of FIG. 31 in an open position causing the cephalad-most and caudal-most retractor blades of the tissue retraction assembly of FIG. 31 to pivot in an outward direction.
Figure 33:
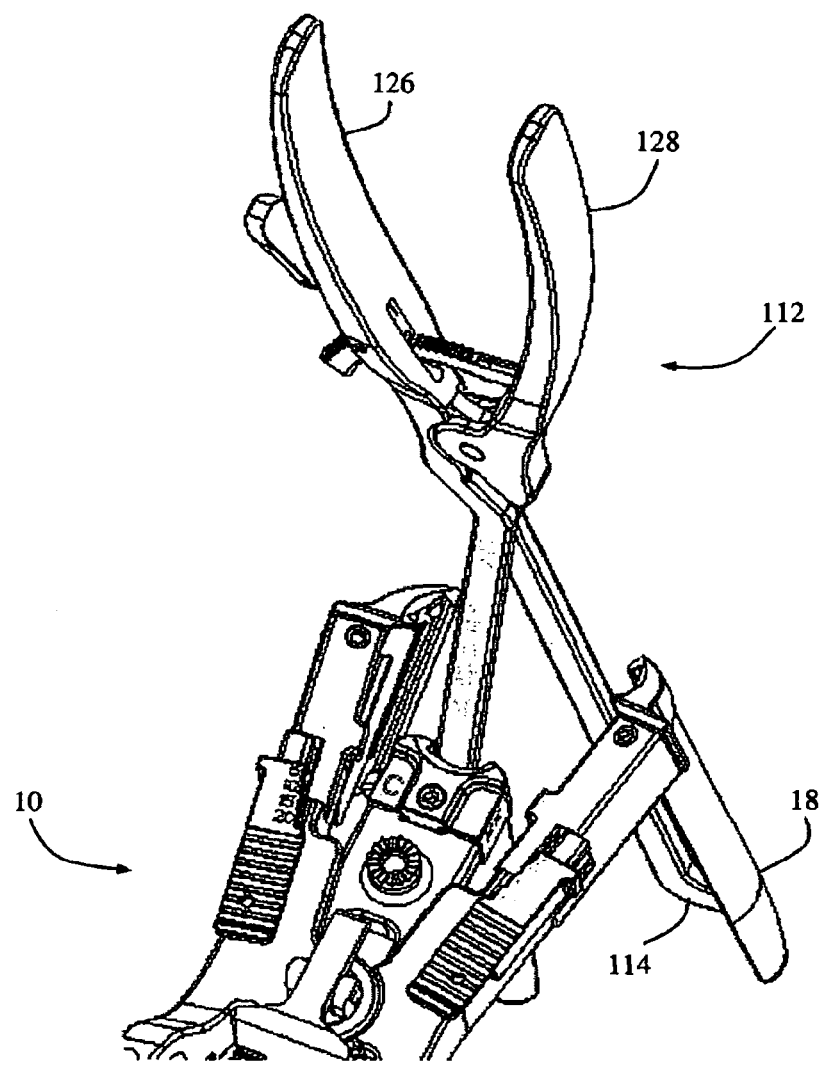
Figure 34:
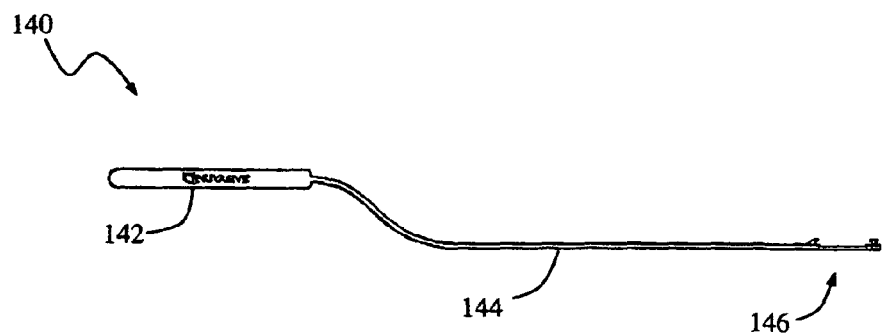
FIGS. 34-35 are side and perspective views, respectively, of a shim inserter according to a preferred embodiment of the present invention.
Figure 35:
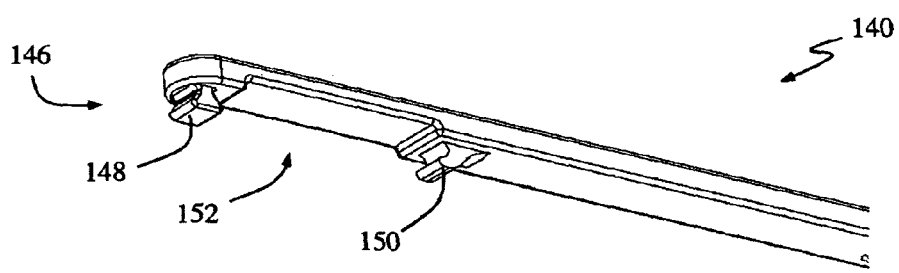

With the retractor blades 16, 18 in an initial alignment (i.e. generally perpendicular to the handle 20) and the first and second arm members 26, 28 in an "open" position, the blade expander 112 may be inserted into the operative corridor in a first "closed" position, as shown by way of example in FIG. 31. The blade engagement members 114, 116 may be positioned to interact with the retractor blades 16, 18, respectively. The user may then operate the blade expander 112 by squeezing handle extensions 126, 128, thereby causing first and second elongated extenders 118, 120 to spread apart into a second "open" position shown generally in FIG. 30. Blade engagement members 114, 116 are thus forced against the retractor blades 16, 18, causing distal pivot members 70, 71 to pivot in an outward direction (shown by way of example in FIGS. 32-33). Once the desired degree of angulation (secondary alignment) of the retractor blades 16, 18 is achieved, the user should cease squeezing the handle extensions 126, 128. Due to the interaction between engagement features 132, 136 of the locking element 124, the blade expander 112 is effectively locked in this second position. When desired, the blade expander 112 may be returned to a first closed position by engaging manual depressor 138 on release member 134, allowing blade expander 112 to be removed from the operative corridor 15.

Figure 36:
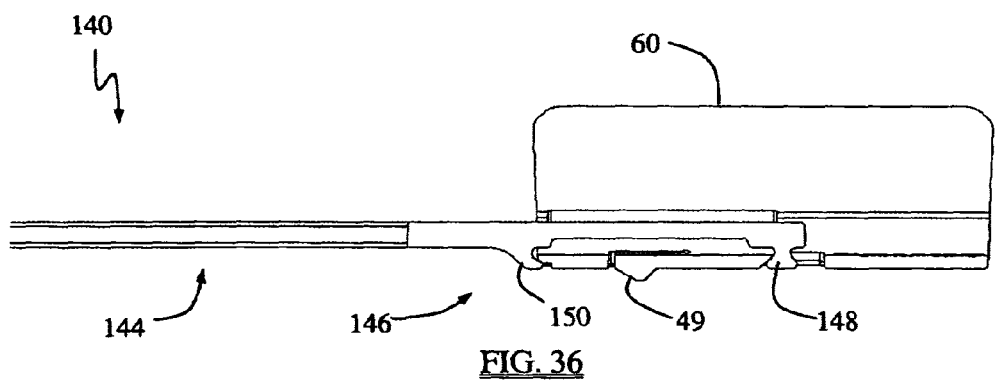
FIGS. 36-37 are side and perspective views, respectively, of the shim inserter of FIG. 34 coupled to a shim.
Figure 37:
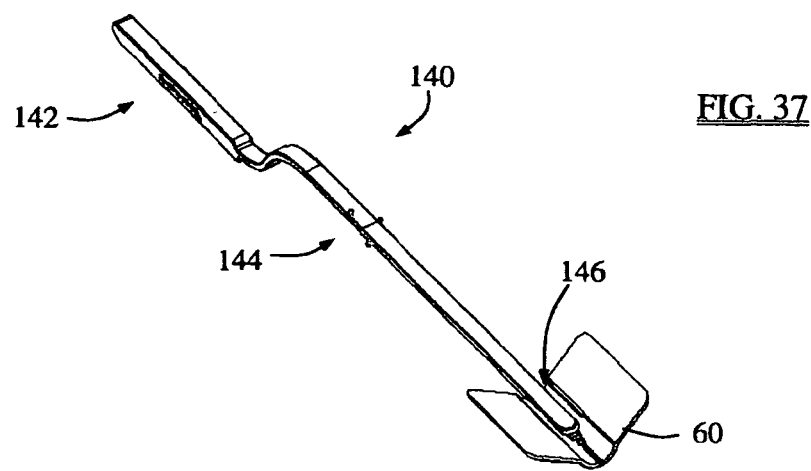

FIGS. 34-38 illustrate an inserter 140 for inserting retractor extenders 22, 24, 60 and/or shim element 25 according to a preferred embodiment of the present invention. By way of example only, inserter 140 is shown and described herein in conjunction with retractor extender 60, although it is to be readily appreciated that the inserter 140 may be employed in a similar manner with retractor extenders 22, 24 and shim element 25 according to the present invention. Inserter 140 includes a handle 142, and elongated region 144, and a distal end 146. The handle 142 may be any configuration suitable to allow purchase with the human hand, including but not limited to a grip (composed of any suitable material including but not limited to rubber, plastic, or metal) or a T-handle. The elongated region 144 may be straight or included any number of curved regions, and may be of any length necessary to mate the retractor extender 60 with the retractor blade 16/18. The distal end 146 may include a distal stub 148, a grip protrusion 150, and a recessed region 152. The distal stub 148 is configured to interact with elongated slot 43 of retractor extender 60 such that the retractor extender 60 is rigid relative to the inserter 140. Grip protrusion 150 is dimensioned to engage snugly over the edge of retractor extender 60 such that the retractor extender 60 is locked into place on the inserter 140 (FIG. 36).

Figure 38:
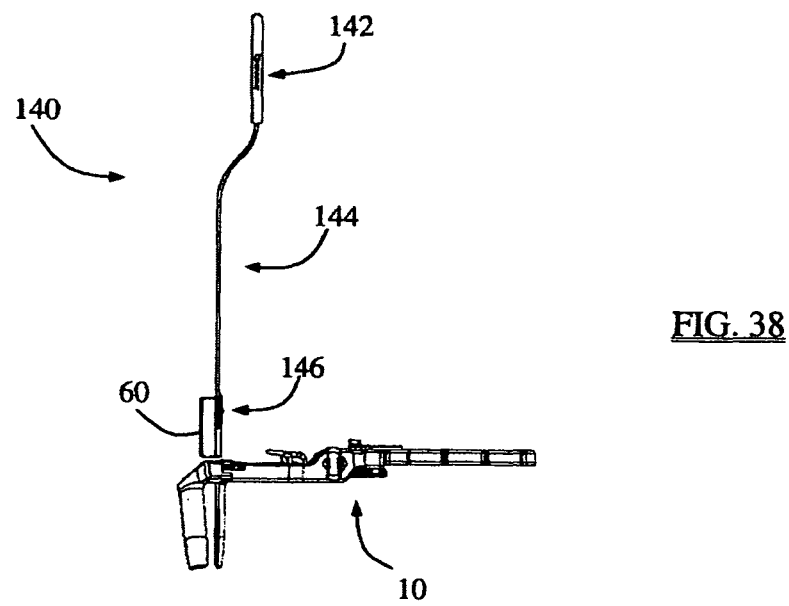
FIGS. 38-39 are side and top views, respectively, of the shim inserter of FIG. 36 prior to insertion of the shim.
Figure 39:
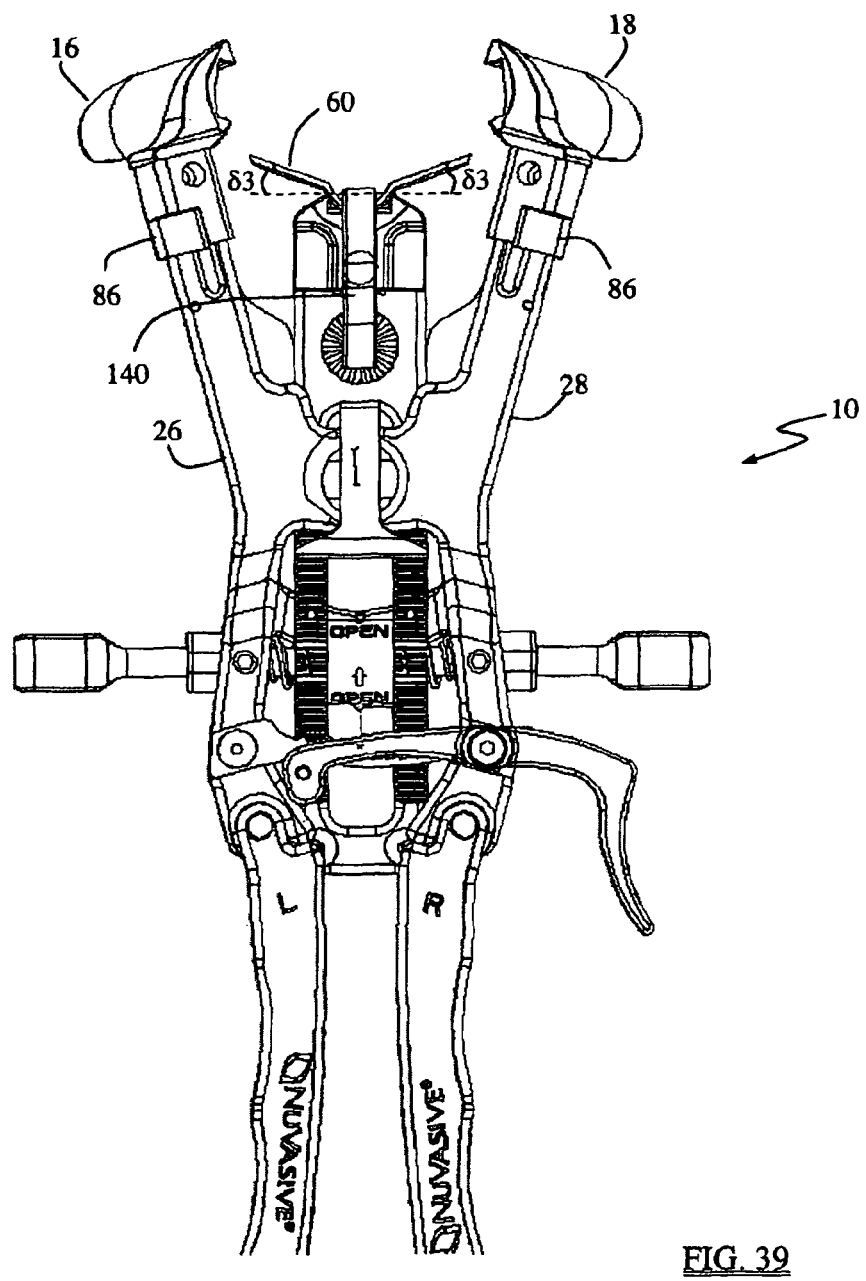
Figure 40:
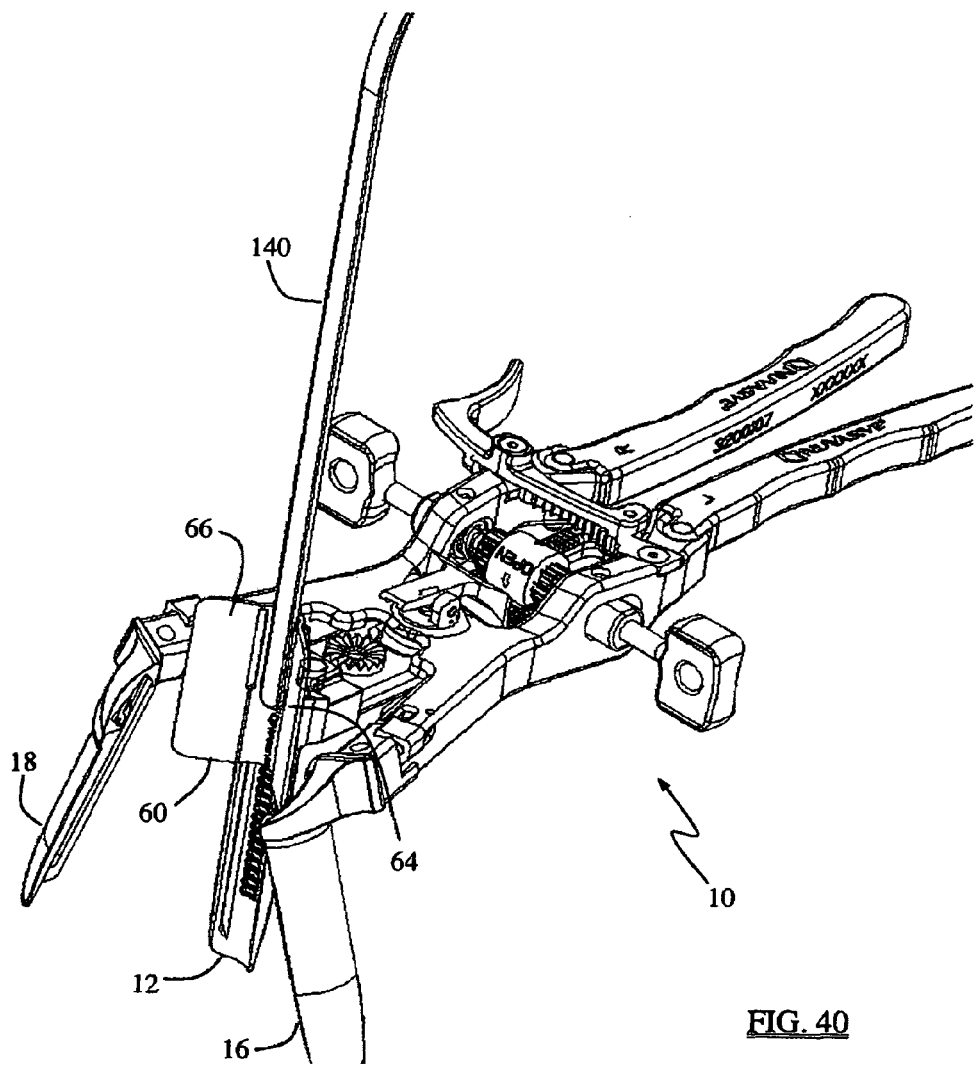
FIGS. 40-41 are perspective and top views, respectively, of a shim inserter according to the present invention coupled to a shim in the initial phase of insertion, where the shim is entering the operative corridor at the skin level.
Figure 41:
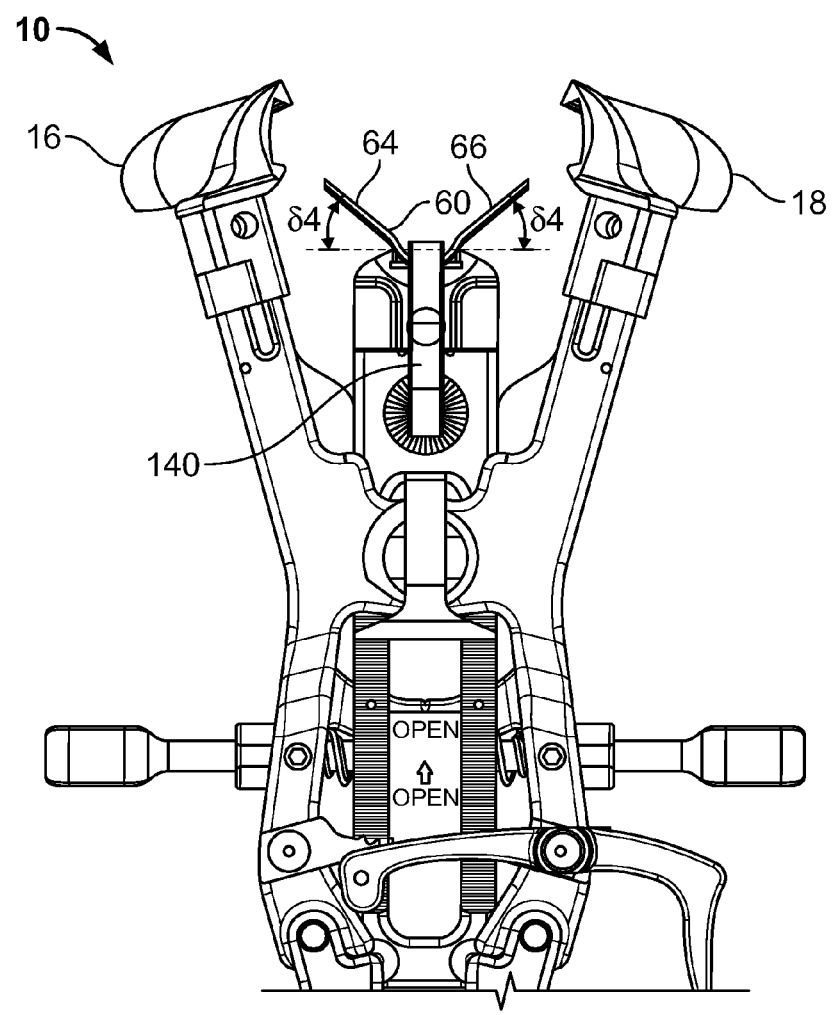
Figure 42:
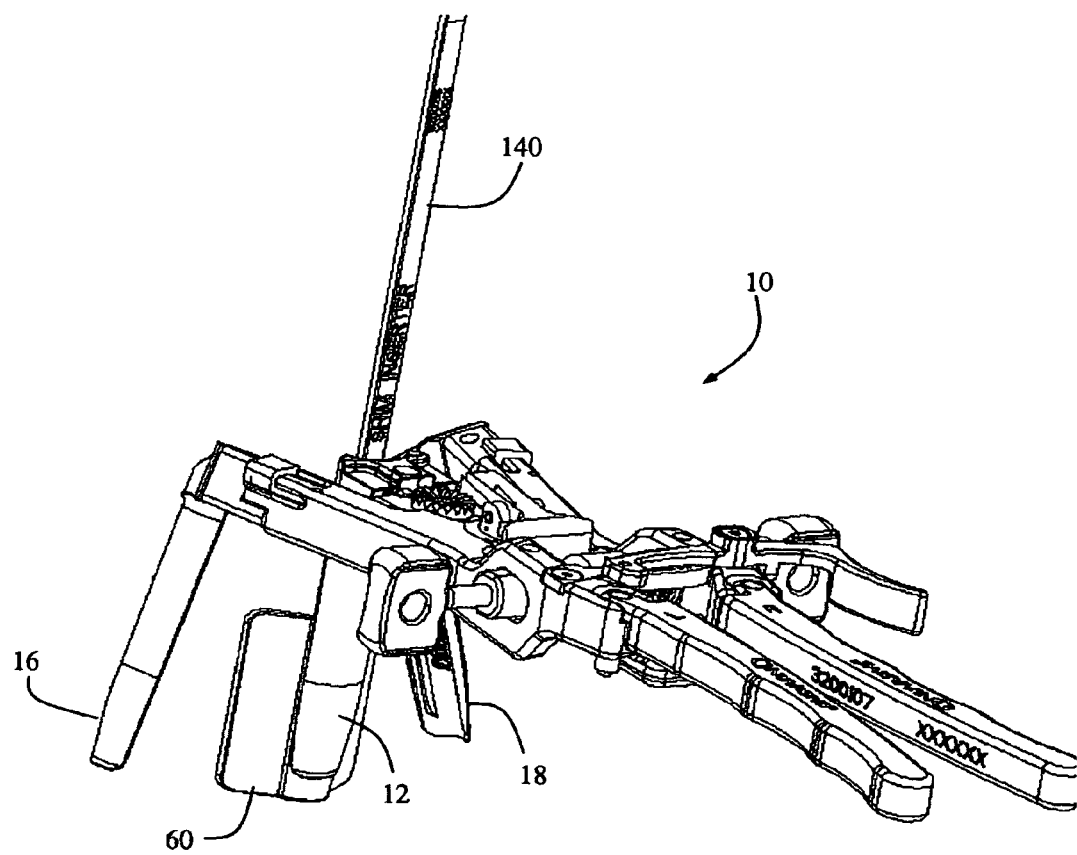
FIGS. 42-43 are perspective and top views, respectively, of the shim inserter & shim of FIG. 52, where the shim has been inserted beyond the skin level and fully into the operative corridor.
Figure 43:
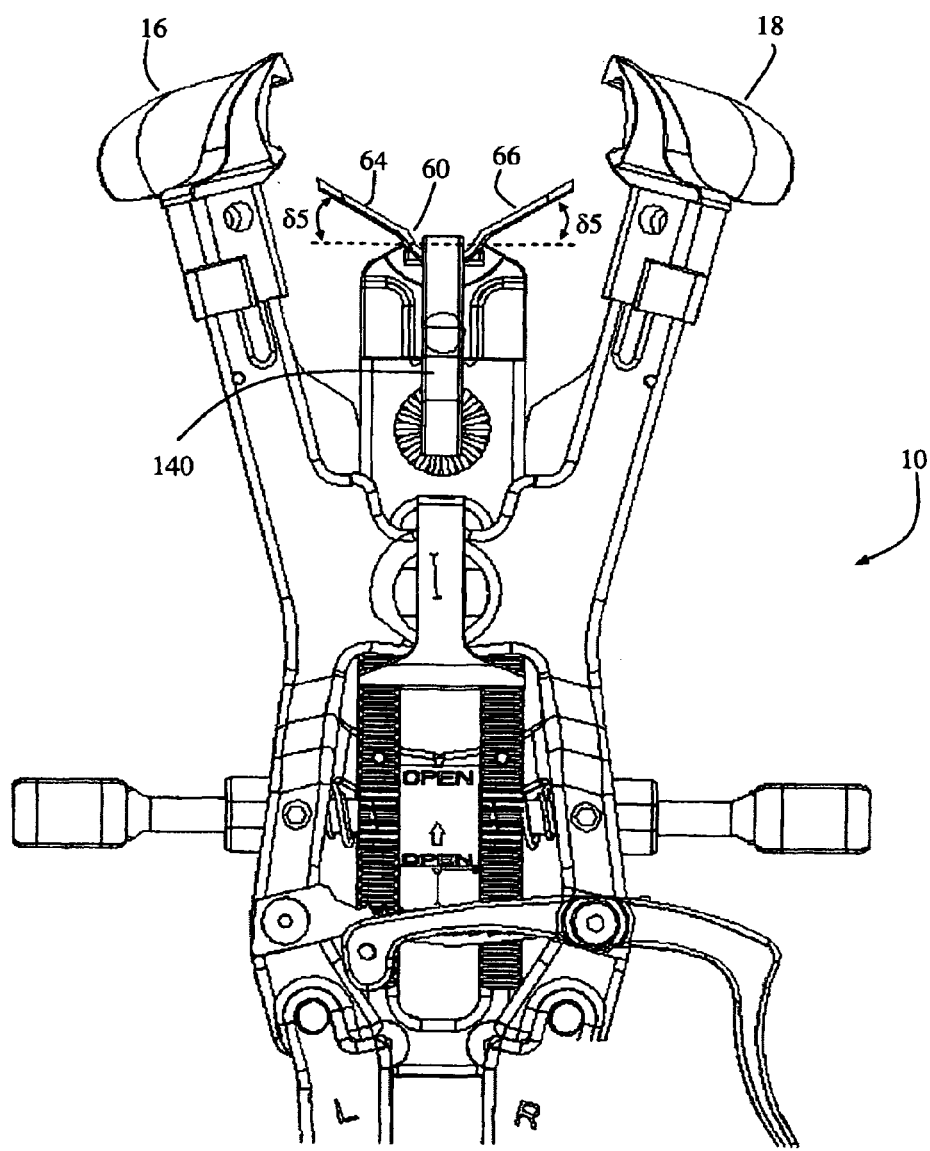
Figure 44:
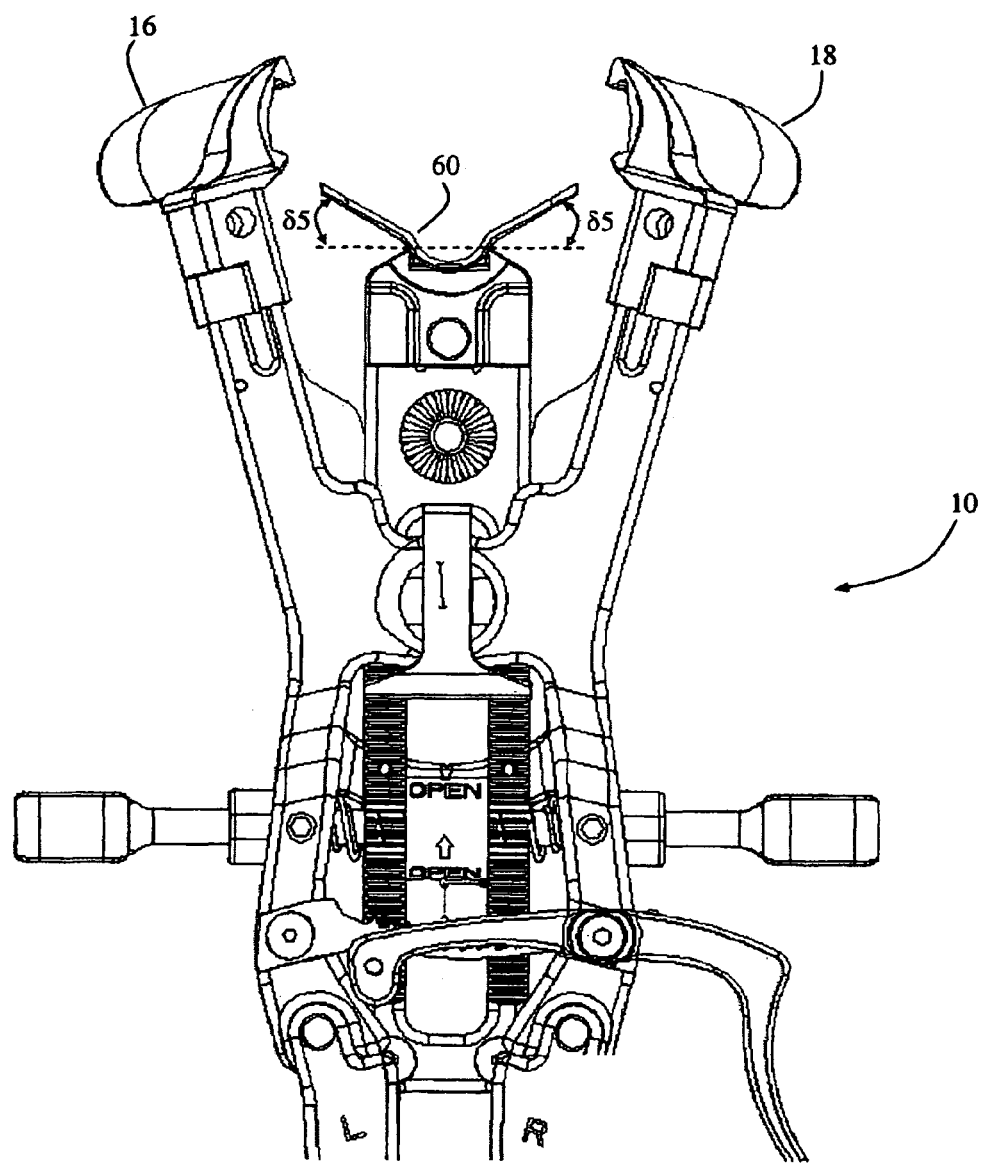
FIGS. 44-45 are top and perspective views, respectively, of a fully inserted shim, wherein the shim inserter has been removed.
Figure 45:
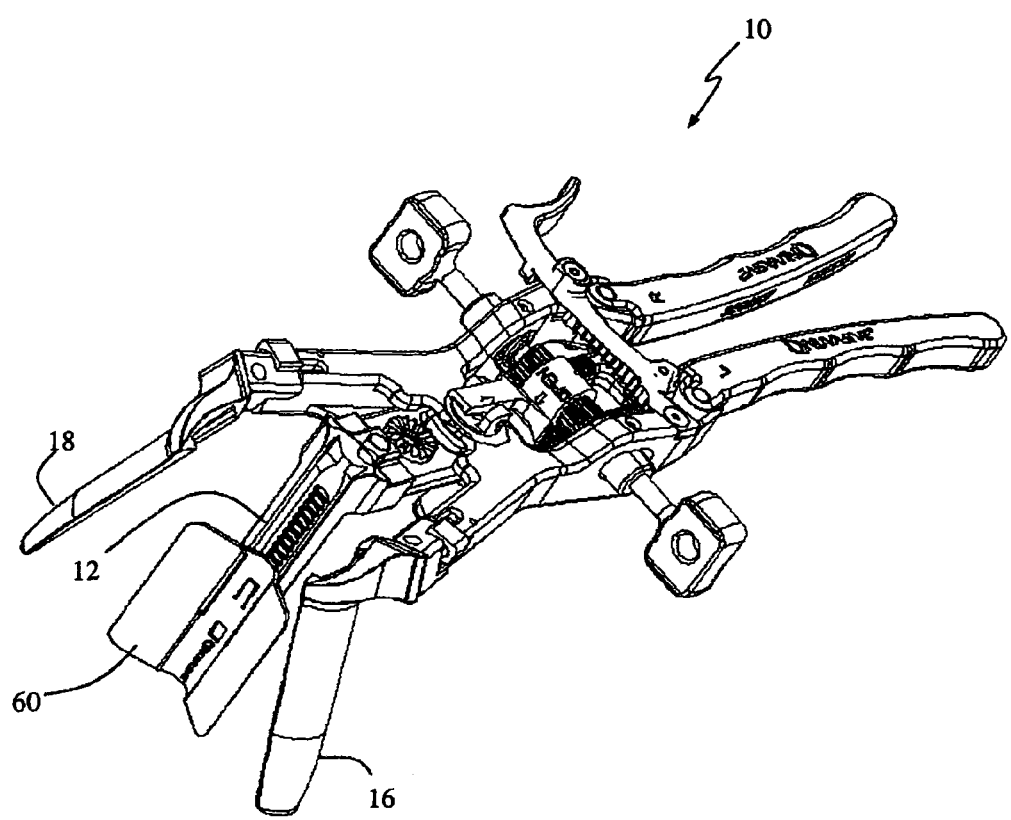

In use, once the retractor extender 60 is attached to the inserter 140 (FIG. 37), the retractor extender 60/inserter 140 combination is positioned over the desired retractor blade (shown as the posterior blade 12 in FIG. 38). As the retractor extender 60 is inserted through the operative opening at the level of the skin (FIGS. 40-41), the retractor extender 60 may compress together such that the panels 64, 66 are oriented at a greater angle (denoted by δ4 in FIG. 41) than at default position (denoted by δ3 in FIG. 39). As the retractor extender 60 is inserted beyond the level of the skin and into the operative corridor 15 (FIGS. 42-43), the panels 64, 66 may expand to a lesser angle (denoted by δ5 in FIG. 43), which may or may not be the same angle as in default position. Once the retractor extender 60 has been inserted onto the retractor blade 12, the inserter 140 may be removed (FIGS. 44-45).

Figure 46:
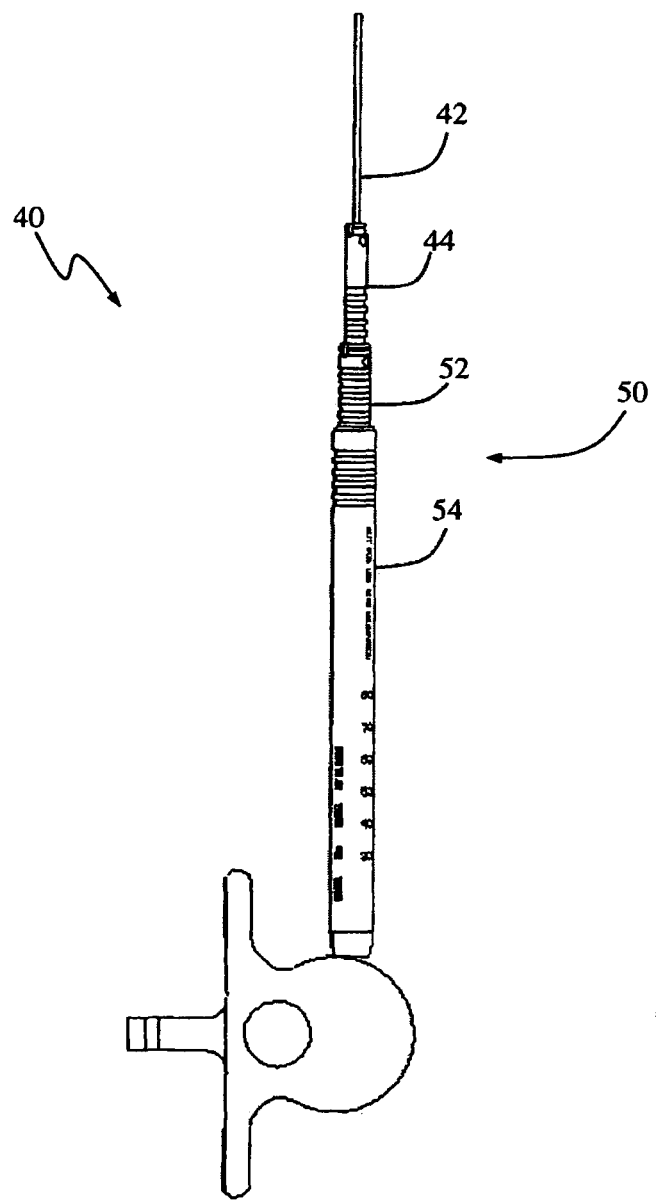
FIG. 46 is a side view illustrating the use of a tissue distraction assembly (comprising a plurality of dilating cannulae over a K-wire) to distract tissue between the skin of the patient and the surgical target site according to the present invention.

FIG. 46 illustrates a tissue distraction assembly 40 forming part of the surgical access system according to the present invention. The tissue distraction assembly 40 includes a K-wire 42, an initial dilating cannula 44, and a sequential dilation system 50. In use, the K-wire 42 is disposed within the initial dilating cannula 44 and the assembly is advanced through the tissue towards the surgical target site (e.g. annulus). Again, this is preferably accomplished while employing the nerve detection and/or direction features described above. After the initial dilating assembly is advanced such that the distal end of the initial dilator 44 is positioned within the disc space, the sequential dilation system 50 consisting of one or more supplemental dilators 52, 54 may be employed for the purpose of further dilating the tissue down to the surgical target site. Once again, each component of the sequential dilation system 50 (namely, the K-wire 42 and the supplemental dilators 52, 54) may be, according to the present invention, provided with one or more electrodes (preferably at their distal regions) equipped for use with a nerve surveillance system, such as, by way of example, the type shown and described in the Neurophysiology Monitoring Patents.

Figure 47:
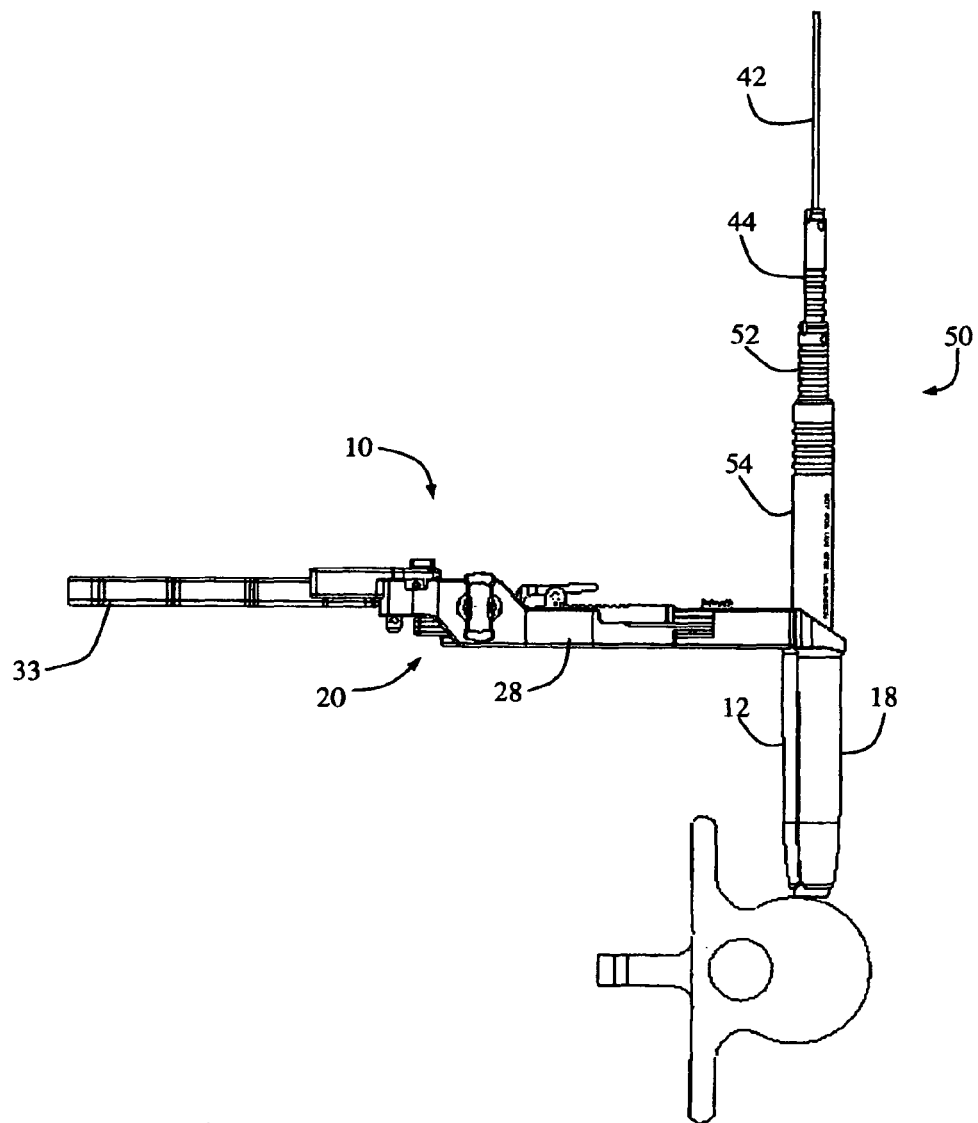
FIG. 47 is a side view of a retractor assembly according to the present invention, comprising a handle assembly having three (3) retractor blades extending there from (posterior, cephalad-most, and caudal-most), shown in a first, closed position and disposed over the tissue distraction assembly of FIG. 46.
Figure 48:
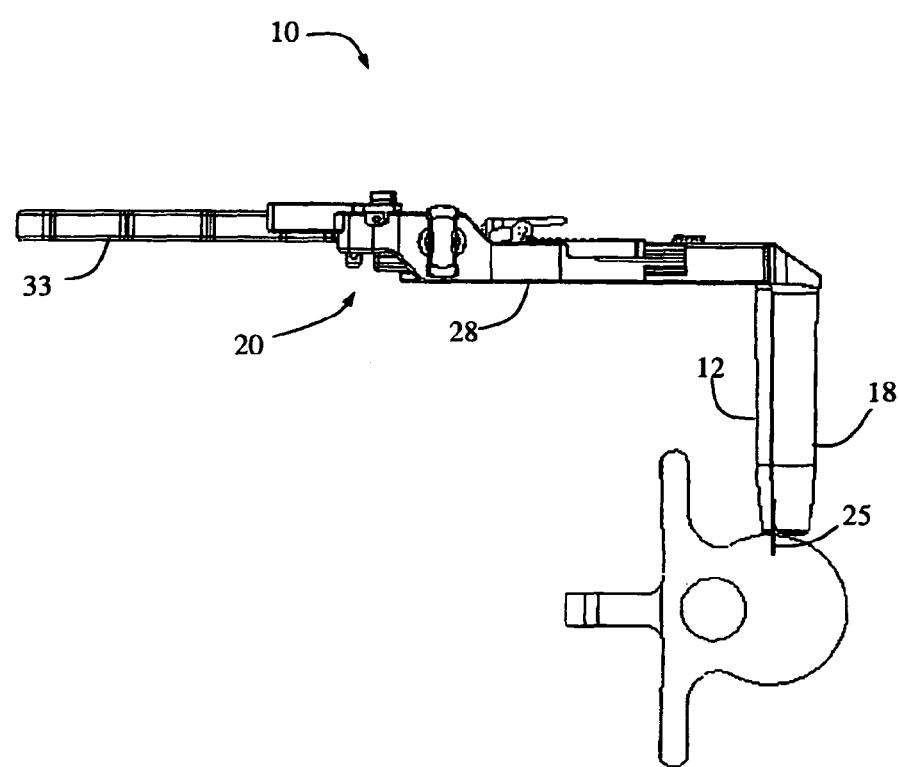
FIG. 48 is a side view of a retractor assembly according to the present invention, comprising a handle assembly having three (3) retractor blades extending there from (posterior, cephalad-most, and caudal-most) with the tissue distraction assembly of FIG. 46 removed and shim element introduced.
Figure 49:
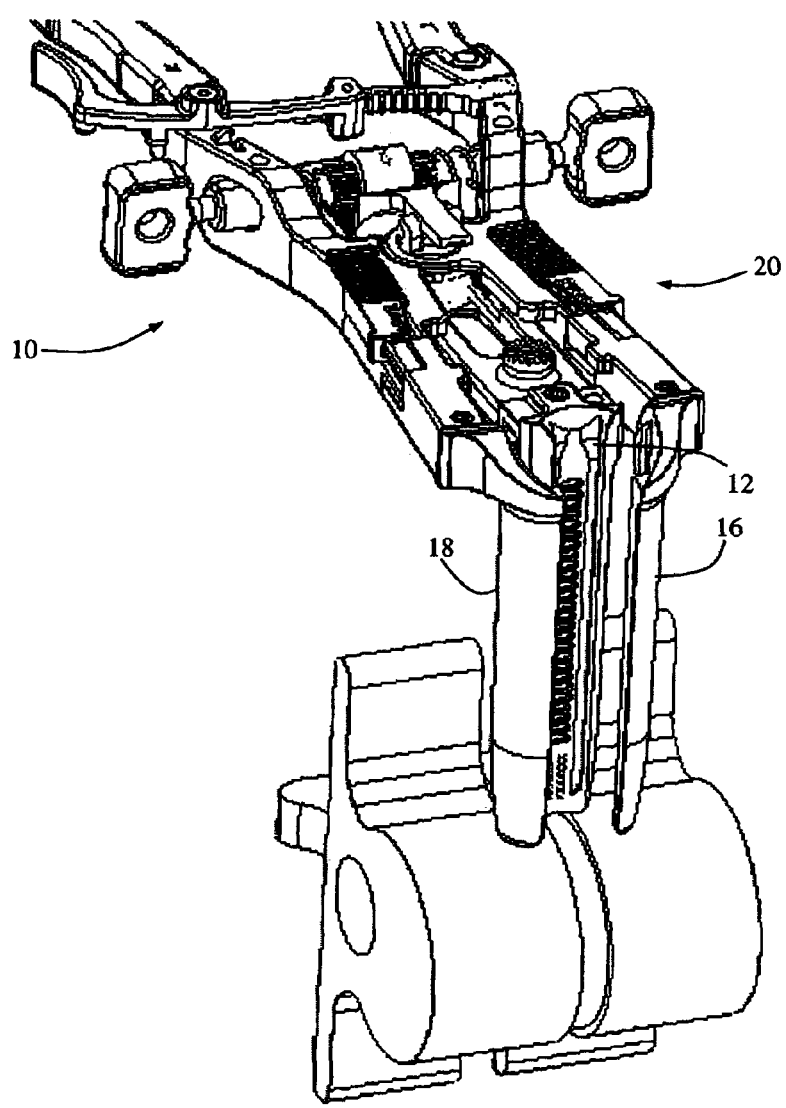
FIG. 49-50 are perspective and top views, respectively, of the retractor assembly in a second, opened (i.e. retracted) position to thereby create an operative corridor to a surgical target site according to the present invention.
Figure 50:
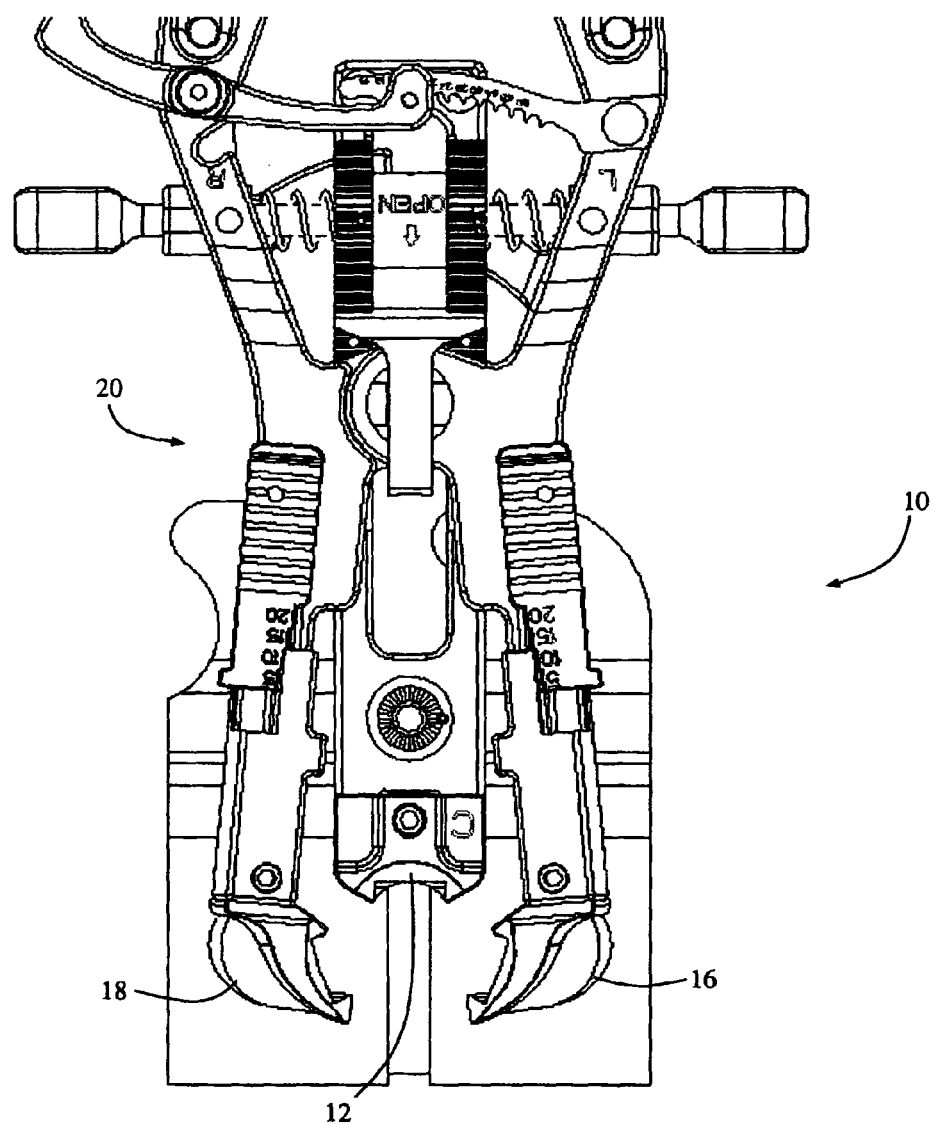
Figure 51:
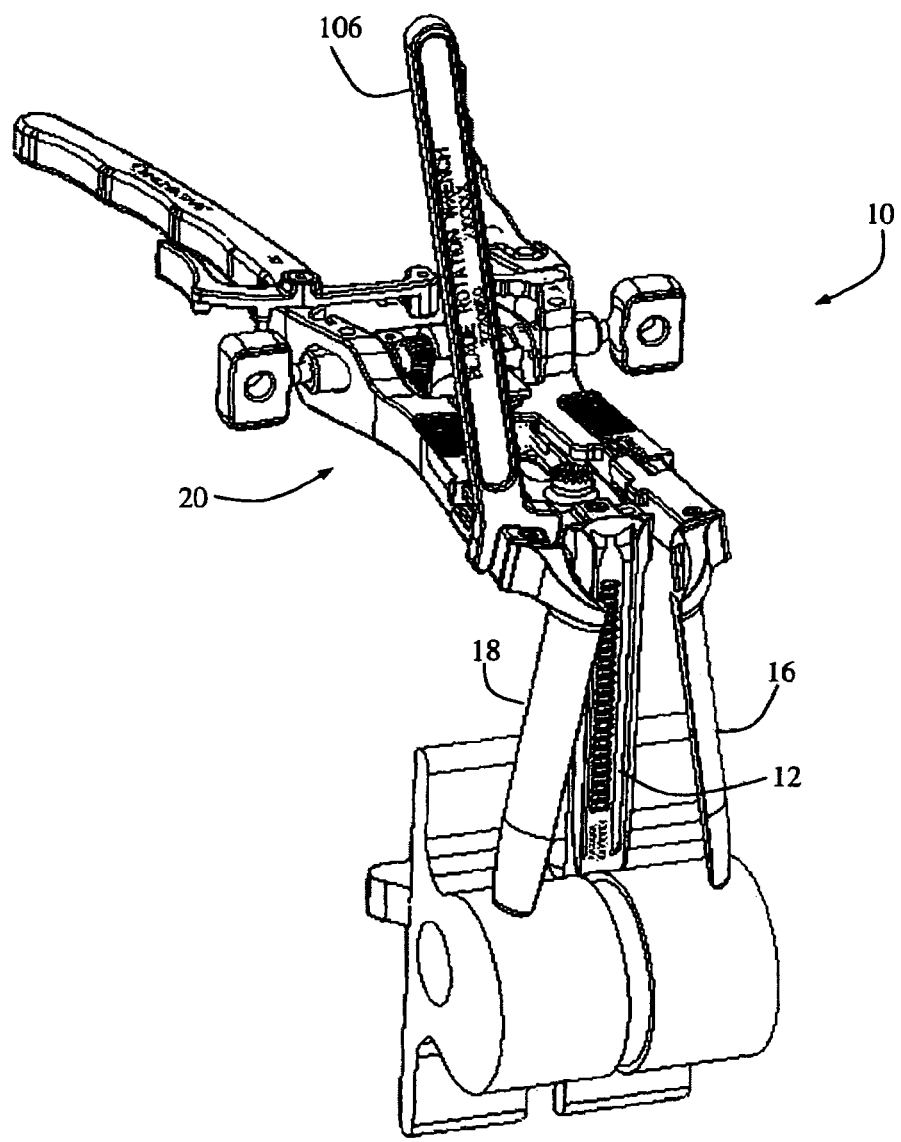
FIGS. 51-52 are perspective views of the retractor assembly of FIG. 50 with the retractor arms in a pivoted position.
Figure 52:
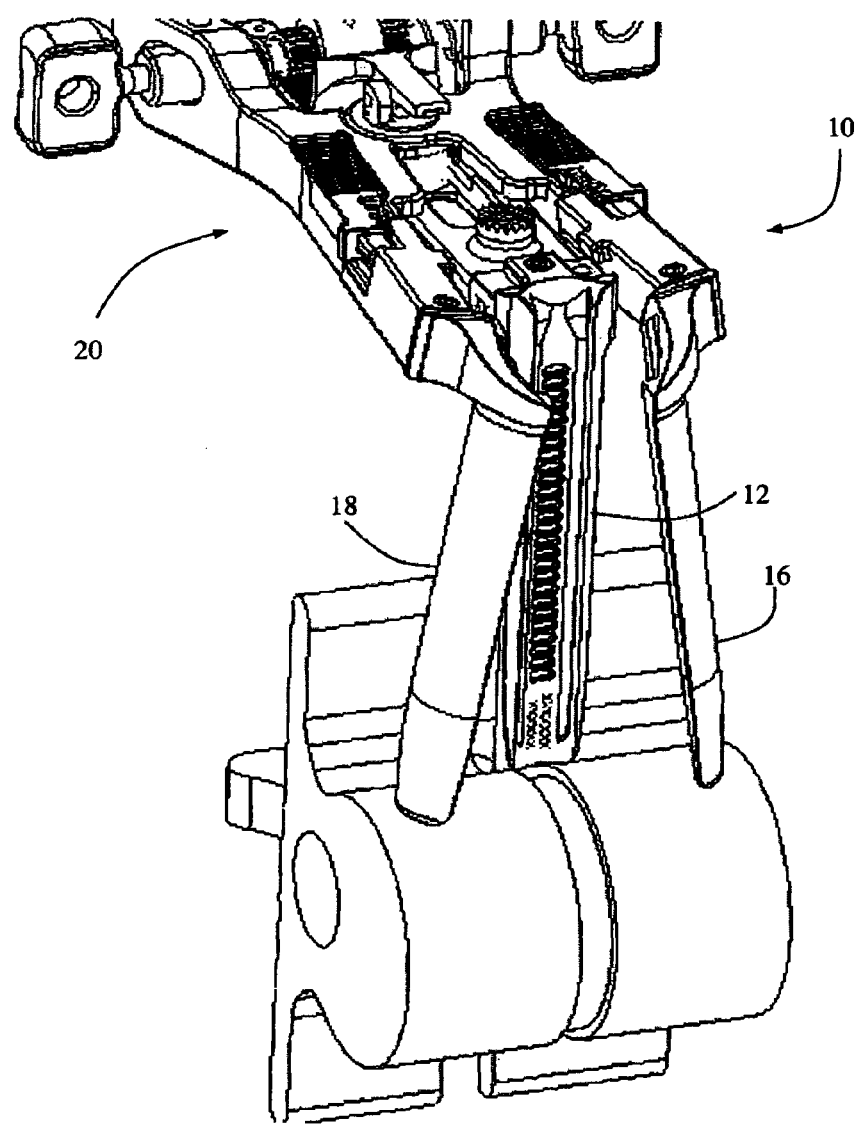
Figure 53:
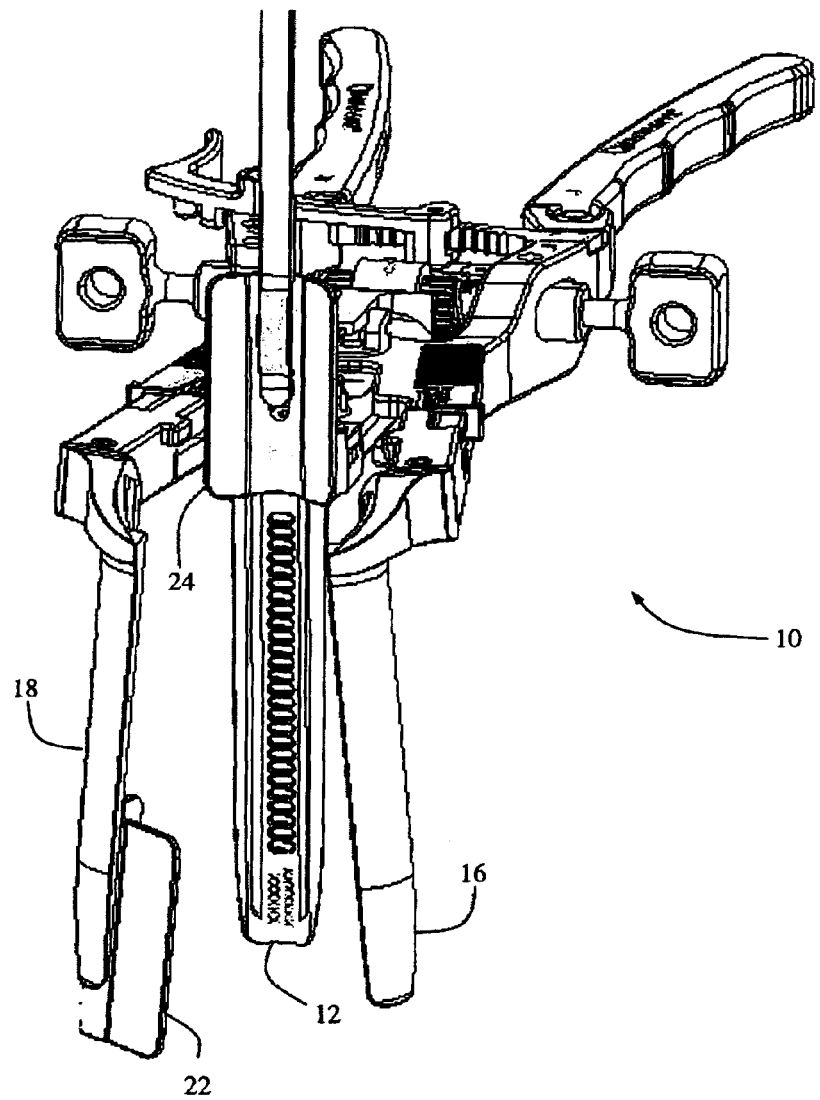
FIG. 53 is a perspective view of the retractor assembly in the second, opened (i.e. retracted) position (with the secondary distraction assembly removed) and with one retractor extender of FIGS. 6-7 coupled to a retractor blade and another retractor being inserted onto a second retractor blade according to the present invention.

As shown in FIG. 47, the retraction assembly 10 of the present invention is thereafter advanced along the exterior of the sequential dilation system 50. This is accomplished by maintaining the retractor blades 12, 16, 18 in a first, closed position (with the retractor blades 12-16 in generally abutting relation to one another as shown in FIGS. 2-3). Once advanced to the surgical target site, the sequential dilation assembly 50 may be removed and the shim element 25 engaged with the first retractor blade 12 such that the distal end thereof extends into the disc space as shown in FIG. 48. At this point, the handle assembly 20 may be operated to move the retractor blades 16, 18 into a second, "retracted" position as shown generally in FIGS. 49-50. As will be appreciated, the first retractor blade 12 is allowed to stay in the same general position during this process, such that the second and third retractor blades 16, 18 move away from the first retractor blade 12. Optionally, the second retractor blade 16 and/or the third retractor blade 18 may be pivoted in an outward direction as shown in FIGS. 51-52. At this point, the narrow and wide retractor extenders 22, 24, 60 may be engaged with any combination of retractor blades 12, 16, 18 as described above and as shown in FIG. 53.

Figure 54:
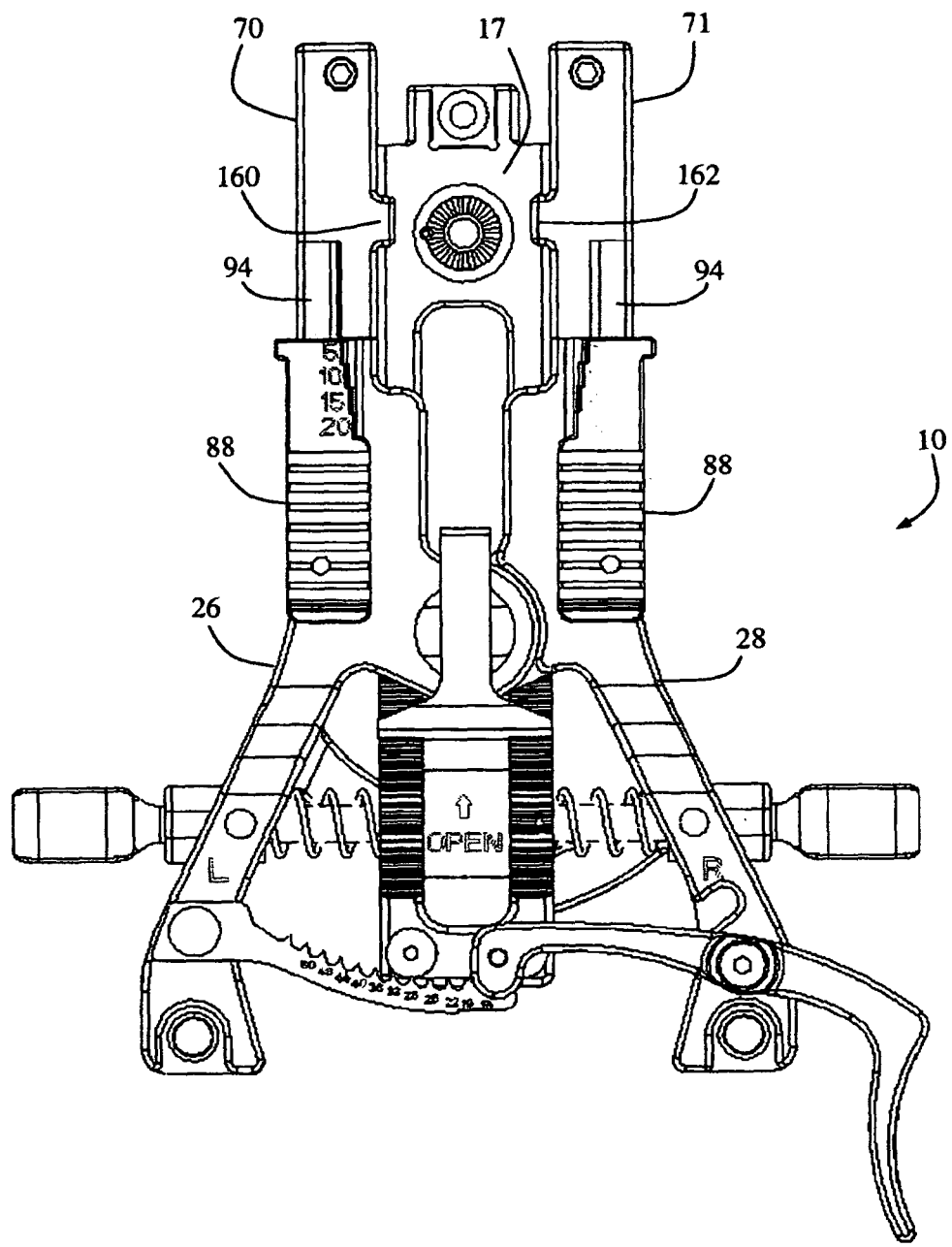
FIGS. 54-55 are perspective views of a handle assembly forming part of the tissue retraction assembly of FIG. 1 shown in an initial closed position.
Figure 55:
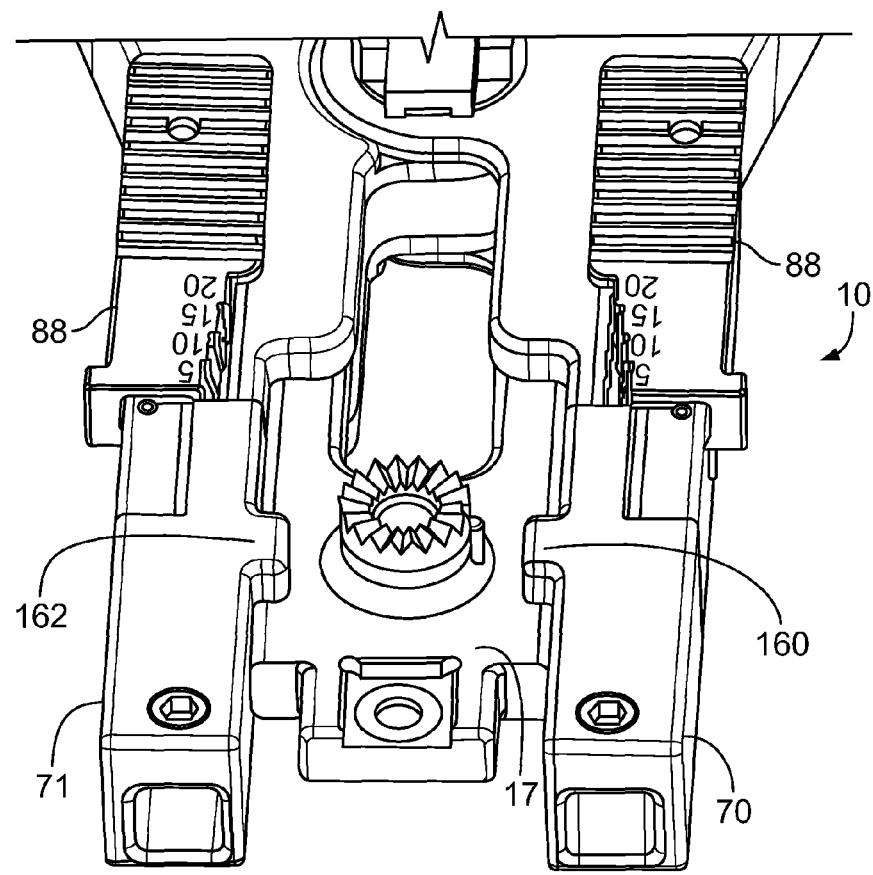

Various improvements and modifications may be made to the surgical access system disclosed herein without deviating from the scope of the present invention. For example, as exemplified in FIGS. 54-56, the tissue retraction system 10 may include an optional locking feature to maintain the blades 16, 18 in an initial alignment (e.g. generally parallel) during insertion. By way of example only, this locking feature may consist of a pair of tabs 160, 162 located on the distal pivot member 70, 71 of first and second arm members 26, 28, respectively. The tabs 160, 162 are dimensioned to extend at least partially over the translating member 17 such that when the tissue retraction system 10 is in an initial closed position as shown in FIGS. 54-55 (e.g. as the tissue retraction system 10 is advanced along the exterior of sequential dilation system 50), the distal pivot members 70, 71 are prevented from pivoting, thereby maintaining the retractor blades 16, 18 in an initial alignment.

Figure 24:
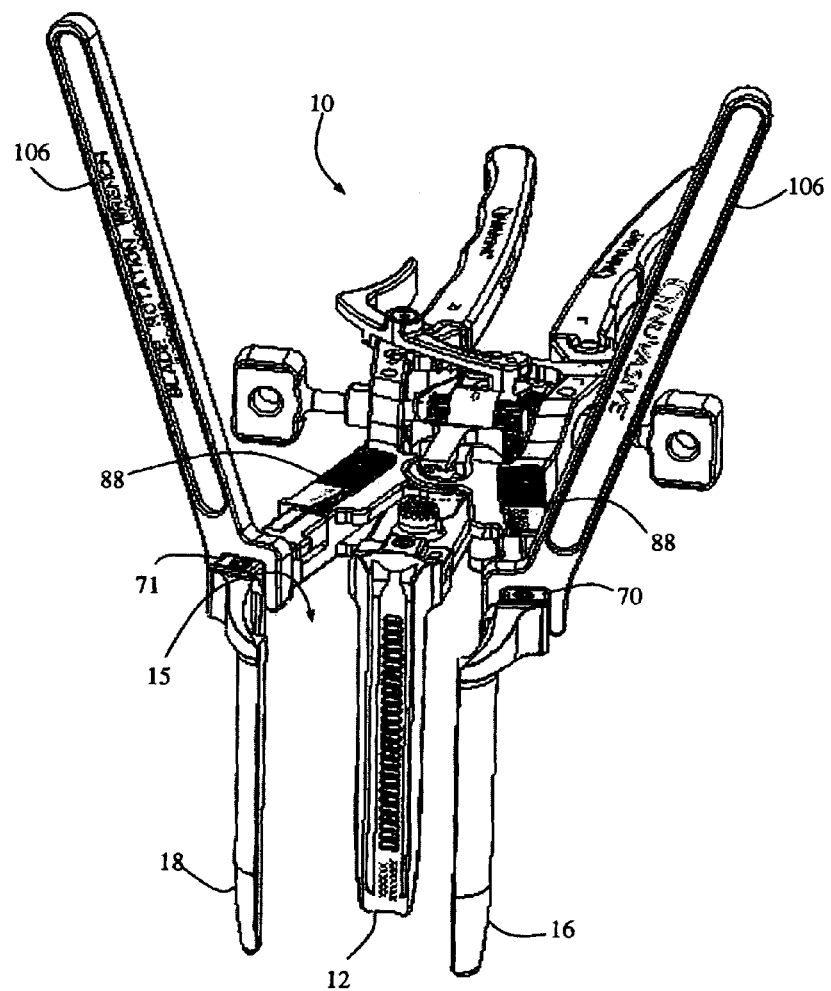
FIG. 24 is a perspective view of the tissue retraction assembly of FIG. 1 in conjunction with a pair of pivot wrenches before the blades have been pivoted.
Figure 56:
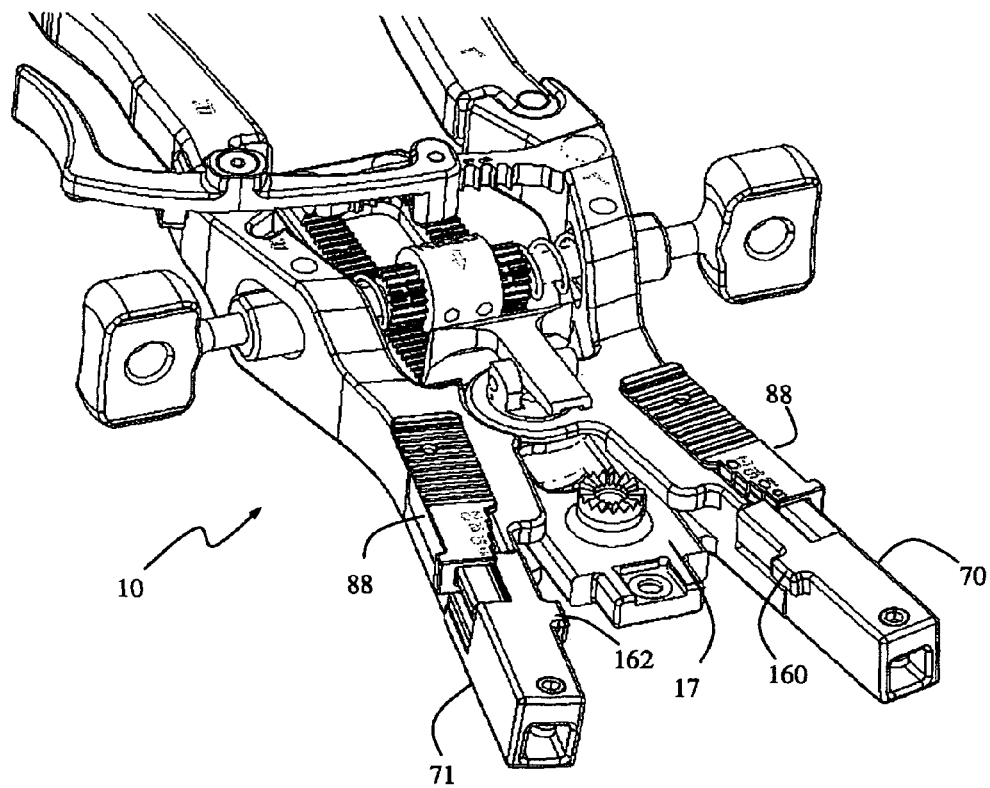
FIG. 56 is a perspective view of the handle assembly of FIG. 54 shown in a secondary open position.

Once the tissue retraction system 10 is fully in place and the sequential dilation system 50 has been removed as described above, the handle assembly 20 may be operated to move the first and second arm members 26, 28 into a second position shown generally in FIG. 56. In so doing, retractor blades 16, 18 are also moved into a second, "retracted" position. The presence of the patient's soft tissue defining the walls of the operative corridor is generally sufficient to maintain the retractor blades 16, 18 in the initial (e.g. generally vertical) alignment despite the fact that locking tabs 160, 162 are no longer engaged with translating member 17. At this point, the surgeon may elect to expand the operative corridor 15 by manually pivoting the retractor blades 16, 18 in a generally outward direction, using by way of example only either a pivot wrench 106 (FIGS. 24-26) and/or a blade expander 112 (FIGS. 31-33) as described above.

As mentioned above, any number of distraction components and/or retraction components (including but not limited to those described herein) may be equipped to detect the presence of (and optionally the distance and/or direction to) neural structures during tissue distraction and/or retraction. This is accomplished by employing the following steps: (1) one or more stimulation electrodes are provided on the various distraction and/or retraction components; (2) a stimulation source (e.g. voltage or current) is coupled to the stimulation electrodes; (3) a stimulation signal is emitted from the stimulation electrodes as the various components are advanced towards or maintained at or near the surgical target site; and (4) the patient is monitored to determine if the stimulation signal causes muscles associated with nerves or neural structures within the tissue to innervate. If the nerves innervate, this may indicate that neural structures may be in close proximity to the distraction and/or retraction components.

Neural monitoring may be accomplished via any number of suitable fashions, including but not limited to observing visual twitches in muscle groups associated with the neural structures likely to found in the tissue, as well as any number of monitoring systems, including but not limited to any commercially available "traditional" electromyography (EMG) system (that is, typically operated by a neurophysiologist). Such monitoring may also be carried out via the surgeon-driven EMG monitoring system shown and described in the commonly owned and co-pending Neurophysiology Monitoring Patents referenced above. In any case (visual monitoring, traditional EMG and/or surgeon-driven EMG monitoring), the access system of the present invention may advantageously be used to traverse tissue that would ordinarily be deemed unsafe or undesirable, thereby broadening the number of manners in which a given surgical target site may be accessed.

Figure 57:
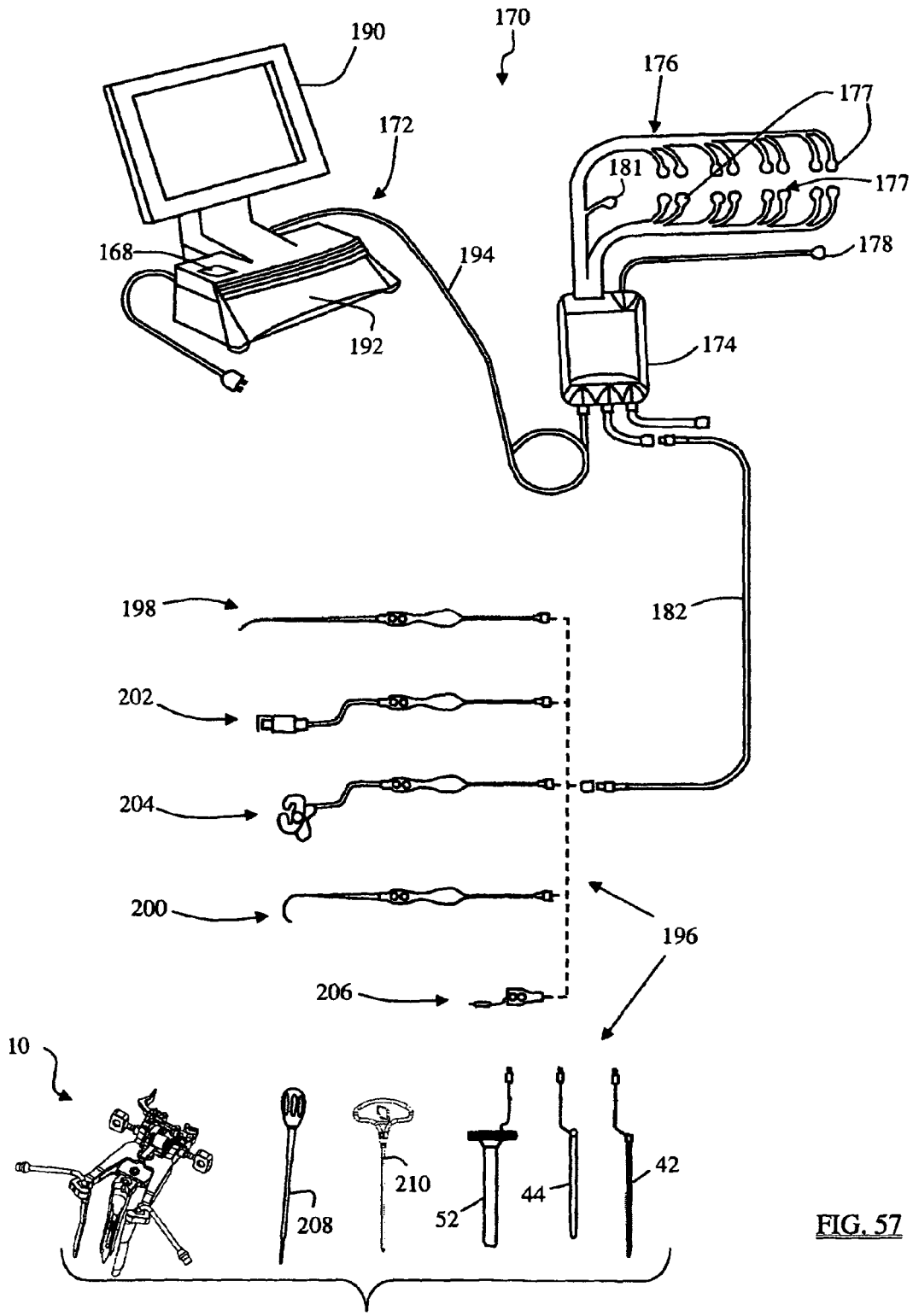
FIG. 57 is a perspective view of one example of a nerve monitoring system for performing nerve monitoring before, during and after creation of an operative corridor to a surgical target site using the surgical access system in accordance with the present invention.
Figure 58:
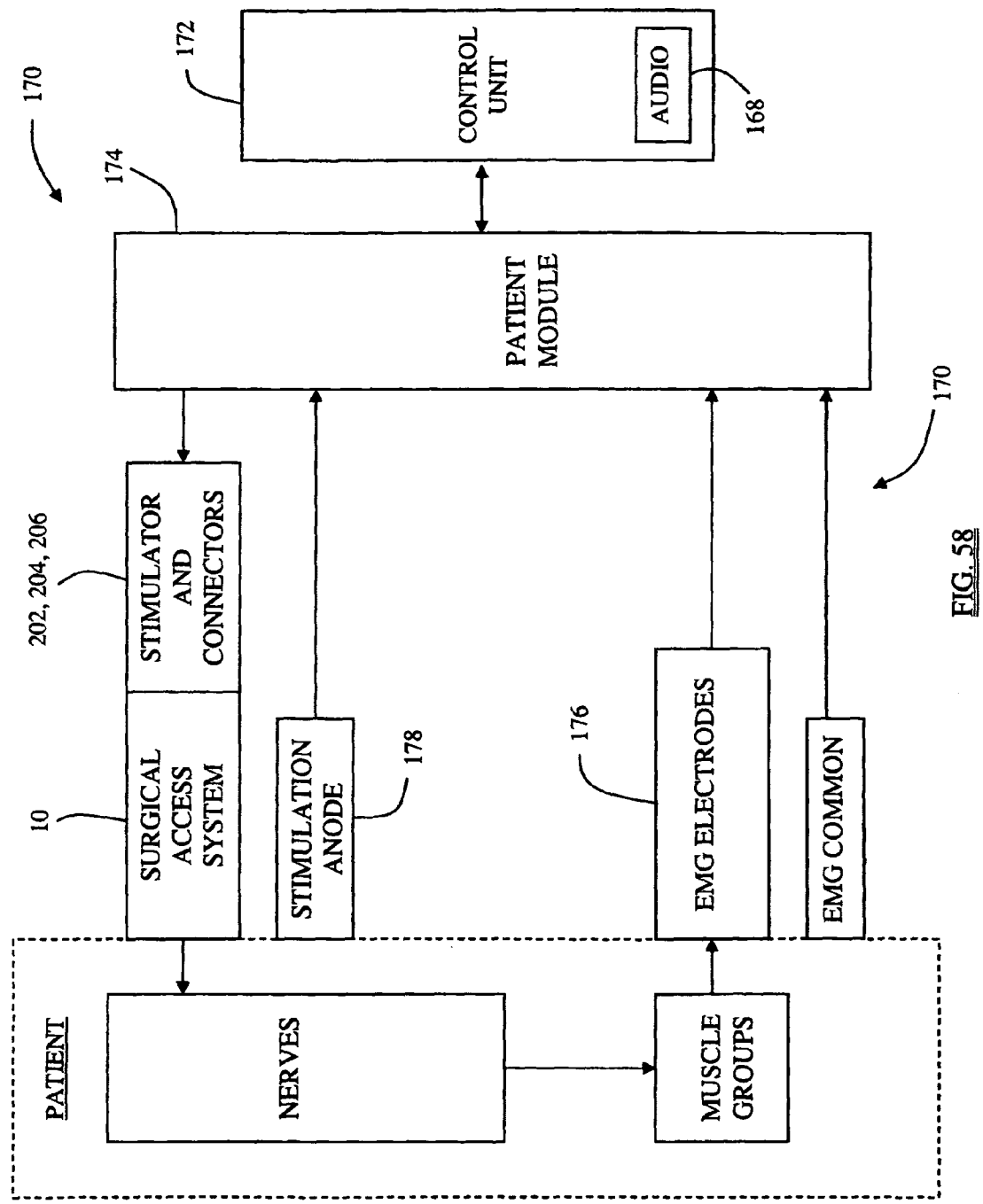
FIG. 58 is a block diagram of the nerve monitoring system shown in FIG. 57.

FIGS. 57-58 illustrate, by way of example only, a monitoring system 170 of the type disclosed in the Neurophysiology Monitoring Patents suitable for use with the surgical access system 10 of the present invention. The monitoring system 170 includes a control unit 172, a patient module 174, and an EMG harness 176 and return electrode 178 coupled to the patient module 174, and a cable 182 for establishing electrical communication between the patient module 174 and any number of surgical accessories 196, including the surgical access system of the present invention (retractor assembly 10 of FIG. 1 and distraction assemblies 40, 50 of FIGS. 46-47, including K-wire 42, initial dilator 44 and sequentially dilating cannulae 52, 54). The surgical accessories 196 may further include, but are not necessarily limited to, devices for performing pedicle screw tests (such as a screw test probe 198), neural pathology monitoring devices (such as a nerve root retractor 200), coupling devices for electronically coupling surgical instruments to the system 170 (such as electric coupling devices 202, 204 and stimulator driver 206), and pilot hole forming components (such as a tap member 208, pedicle access probe 210, or other similar device). More specifically, this electrical communication can be achieved by providing, by way of example only, a hand-held stimulation driver 206 capable of selectively providing a stimulation signal (due to the operation of manually operated buttons on the hand-held stimulation controller 206) to one or more connectors (e.g., coupling devices 202, 204). The coupling devices 202, 204 are suitable to establish electrical communication between the hand-held stimulation controller 206 and (by way of example only) the stimulation electrodes on the K-wire 42, the dilators 44, 52, 54, the retractor blades 12, 16, 18 and/or the shim members 22, 24, 25, 60 (collectively "surgical access instruments").

In order to use the monitoring system 170, then, these surgical access instruments must be connected to at least one of coupling devices 202, 204 (or their equivalent), at which point the user may selectively initiate a stimulation signal (preferably, a current signal) from the control unit 172 to a particular surgical access instruments. Stimulating the electrode(s) on these surgical access instruments before, during and/or after establishing operative corridor will cause nerves that come into close or relative proximity to the surgical access instruments to depolarize, producing a response in a myotome associated with the innervated nerve.

The control unit 172 includes a touch screen display 190 and a base 192, which collectively contain the essential processing capabilities (software and/or hardware) for controlling the monitoring system 170. The control unit 172 may include an audio unit 168 that emits sounds according to a location of a surgical element with respect to a nerve. The patient module 174 is connected to the control unit 172 via a data cable 194, which establishes the electrical connections and communications (digital and/or analog) between the control unit 172 and patient module 174. The main functions of the control unit 172 include receiving user commands via the touch screen display 190, activating stimulation electrodes on the surgical access instruments, processing signal data according to defined algorithms, displaying received parameters and processed data, and monitoring system status and report fault conditions. The touch screen display 190 is preferably equipped with a graphical user interface (GUI) capable of communicating information to the user and receiving instructions from the user. The display 190 and/or base 192 may contain patient module interface circuitry (hardware and/or software) that commands the stimulation sources, receives digitized signals and other information from the patient module 174, processes the EMG responses to extract characteristic information for each muscle group, and displays the processed data to the operator via the display 190.

In one embodiment, the monitoring system 170 is capable of determining nerve direction relative to one or more of the K-wire 42, the dilators 44, 52, 54, the retractor blades 12, 16, 18 and/or the shim elements 22, 24, 25, 60 before, during and/or following the creation of an operative corridor to a surgical target site. Monitoring system 170 accomplishes this by having the control unit 172 and patient module 174 cooperate to send electrical stimulation signals to one or more of the stimulation electrodes provided on these instruments. Depending upon the location of the surgical access system 10 within a patient (and more particularly, to any neural structures), the stimulation signals may cause nerves adjacent to or in the general proximity of the surgical access system 10 to depolarize. This causes muscle groups to innervate and generate EMG responses, which can be sensed via the EMG harness 176. The nerve direction feature of the system 170 is based on assessing the evoked response of the various muscle myotomes monitored by the system 170 via the EMG harness 176.

By monitoring the myotomes associated with the nerves (via the EMG harness 176 and recording electrode 177) and assessing the resulting EMG responses (via the control unit 172), the surgical access system 10 is capable of detecting the presence of (and optionally the distant and/or direction to) such nerves. This provides the ability to actively negotiate around or past such nerves to safely and reproducibly form the operative corridor to a particular surgical target site, as well as monitor to ensure that no neural structures migrate into contact with the surgical access system 10 after the operative corridor has been established. In spinal surgery, for example, this is particularly advantageous in that the surgical access system 10 may be particularly suited for establishing an operative corridor to an intervertebral target site in a postero-lateral, trans-psoas fashion so as to avoid the bony posterior elements of the spinal column.

Figure 59:
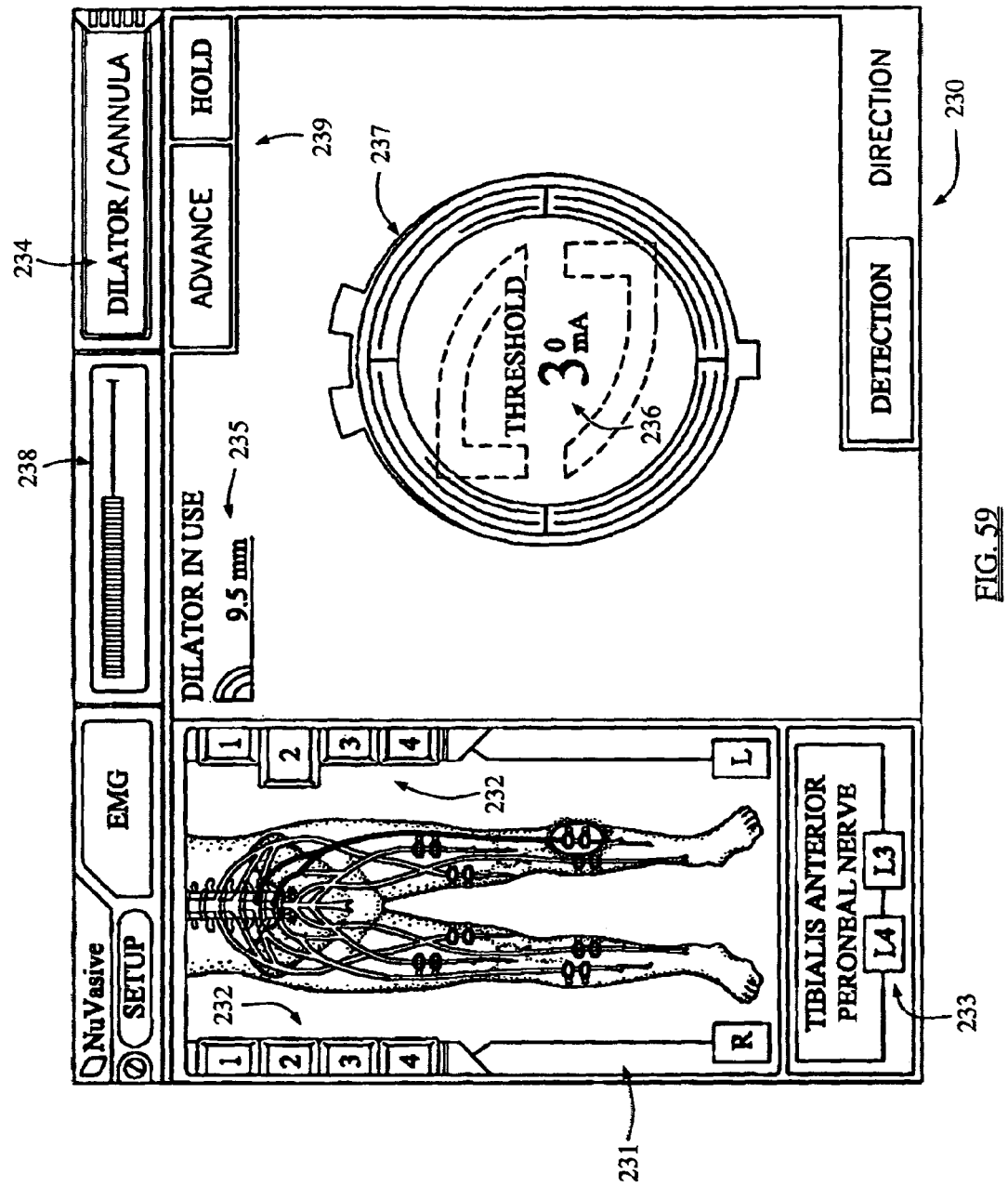
FIGS. 59-60 are screen displays illustrating various features and information communicated to a user during the use of the nerve monitoring system of FIG. 57.
Figure 60:
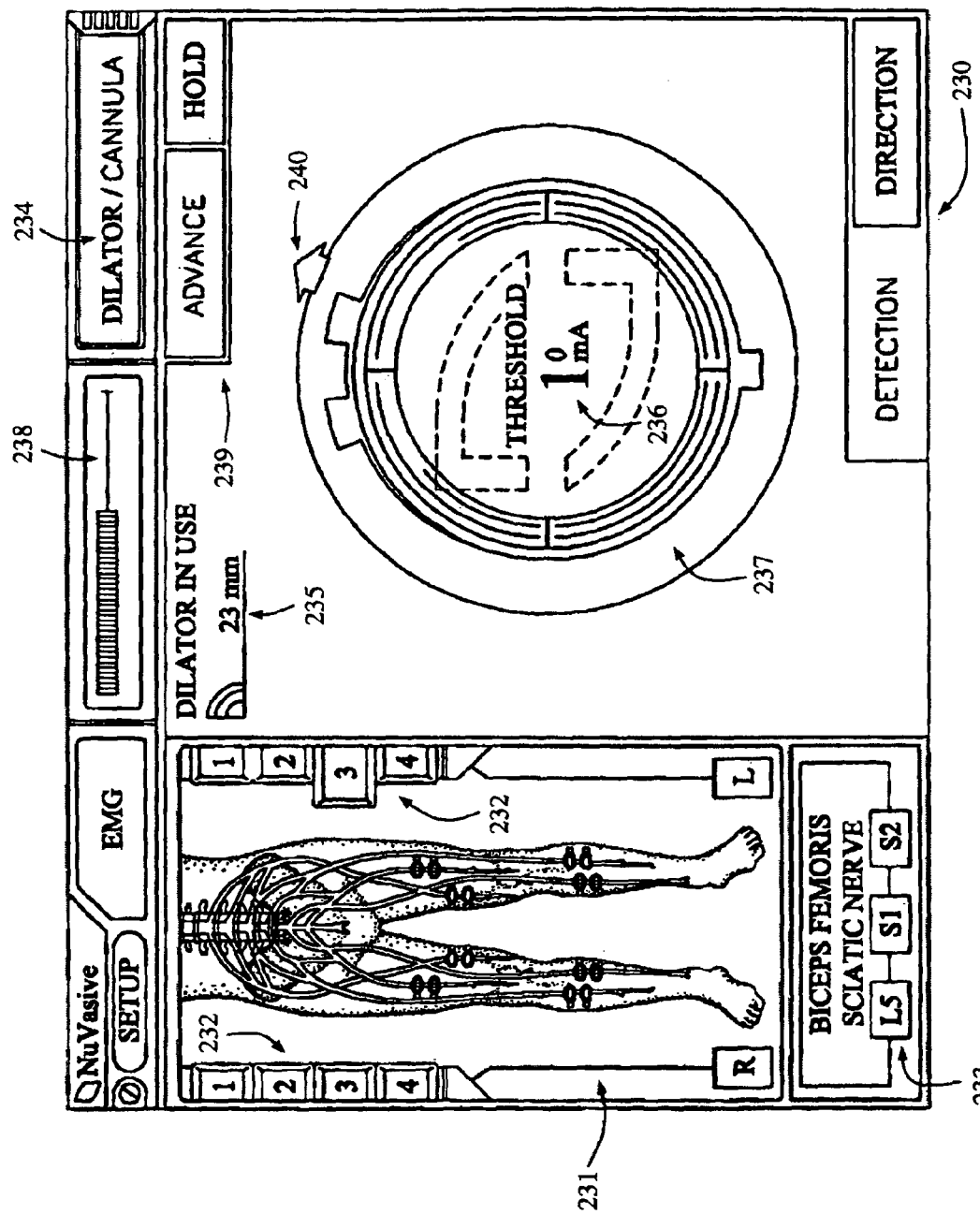

FIGS. 59-60 are exemplary screen displays (to be shown on the display 190) illustrating one embodiment of the nerve direction feature of the monitoring system shown and described with reference to FIGS. 57-58. These screen displays are intended to communicate a variety of information to the surgeon in an easy-to-interpret fashion. This information may include, but is not necessarily limited to, a display of the function 230 (in this case "DIRECTION"), a graphical representation of a patient 231, the myotome levels being monitored 232, the nerve or group associated with a displayed myotome 233, the name of the instrument being used 234 (in this case, a dilator 52, 54), the size of the instrument being used 235, the stimulation threshold current 236, a graphical representation of the instrument being used 237 (in this case, a cross-sectional view of a dilator 52, 54) to provide a reference point from which to illustrate relative direction of the instrument to the nerve, the stimulation current being applied to the stimulation electrodes 238, instructions for the user 239 (in this case, "ADVANCE" and/or "HOLD"), and (in FIG. 60) an arrow 240 indicating the direction from the instrument to a nerve. This information may be communicated in any number of suitable fashions, including but not limited to the use of visual indicia (such as alpha-numeric characters, light-emitting elements, and/or graphics) and audio communications (such as a speaker element). Although shown with specific reference to a dilating cannula (such as at 234), it is to be readily appreciated that the present invention is deemed to include providing similar information on the display 190 during the use of any or all of the various instruments forming the surgical access system 10 of the present invention, including the distraction assembly 40 (i.e. the K-wire 42 and dilators 44, 52, 54) and/or the retractor blades 12, 16, 18 and/or the shim elements 22, 24, 25, 60.

Referring to FIGS. 61-65, a supplemental blade assembly 300 may be provided for optional attachment and use with the tissue retraction assembly 10 described herein. Supplemental blade assembly 300 provides for selectively increasing the number of retractor blades forming the operative corridor during (or before) use. The ability to selectively increase the number of retractor blades affords additional user control over the size and/or configuration of the access corridor, advantageously increasing the versatility of retractor assembly 10. By way of example only, attaching the supplemental blade assembly 300 may effectively increase the width of the operative corridor from approximately 50 mm to 75 mm. Although supplemental blade assembly 300 is shown and described herein in use with a three-bladed configuration of the retractor assembly 10 (thereby comprising a fourth retractor blade as referenced herein), it is to be readily appreciated that the supplemental blade assembly 300 may be used with a retractor assembly 10 configured with any number of primary retractor blades (defined herein as retractor blades attached directly to the handle assembly such as described above with reference to retractor assembly 10).

Figure 61:
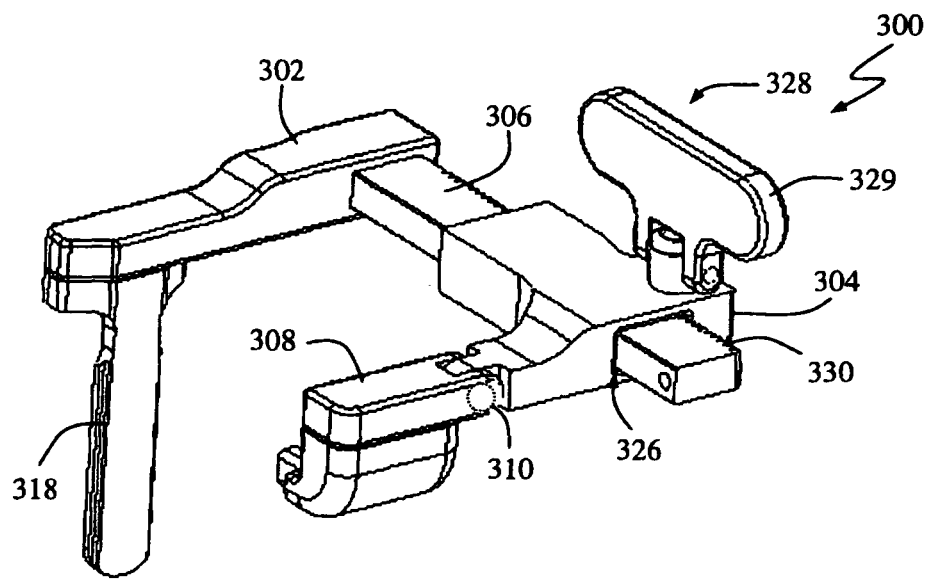
FIGS. 61-62 are perspective views of one example of a supplemental retractor blade assembly (shown without the supplemental retractor blade) according to one aspect of the present invention.
Figure 62:
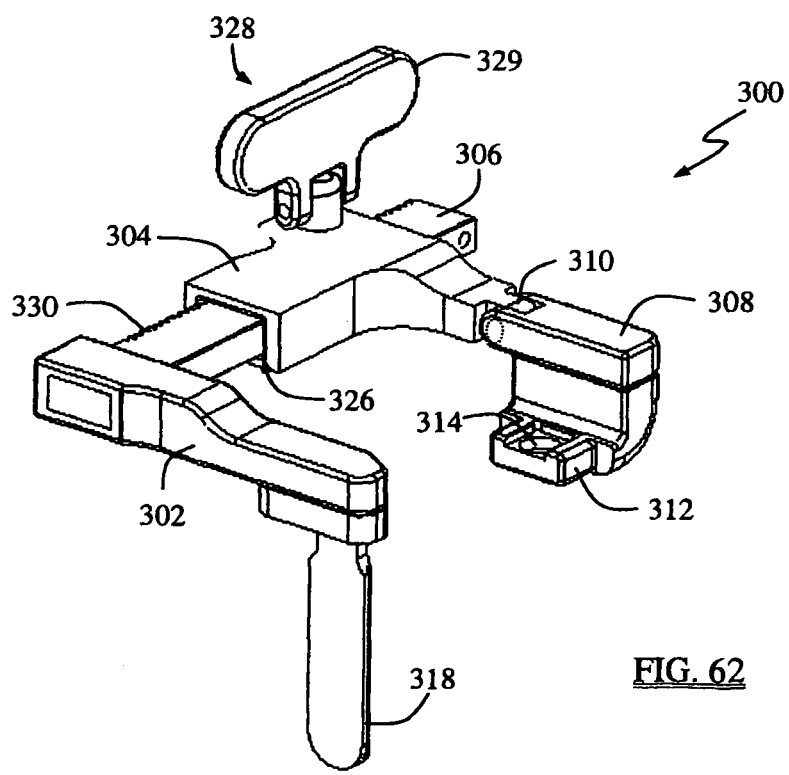
Figure 63:
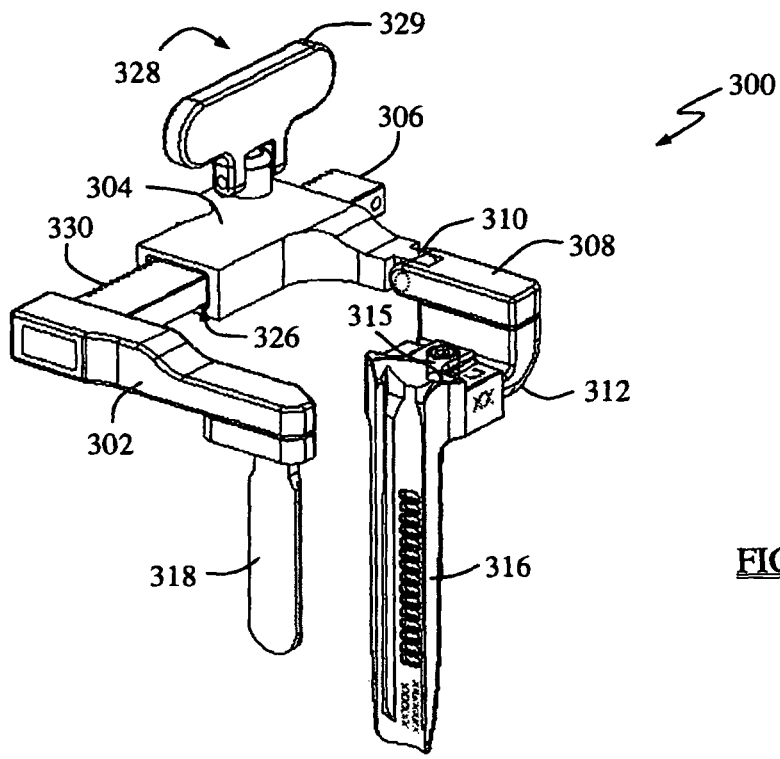
FIGS. 63-65 are perspective views of the supplemental blade assembly of FIG. 61 including a supplemental retractor blade.
Figure 64:
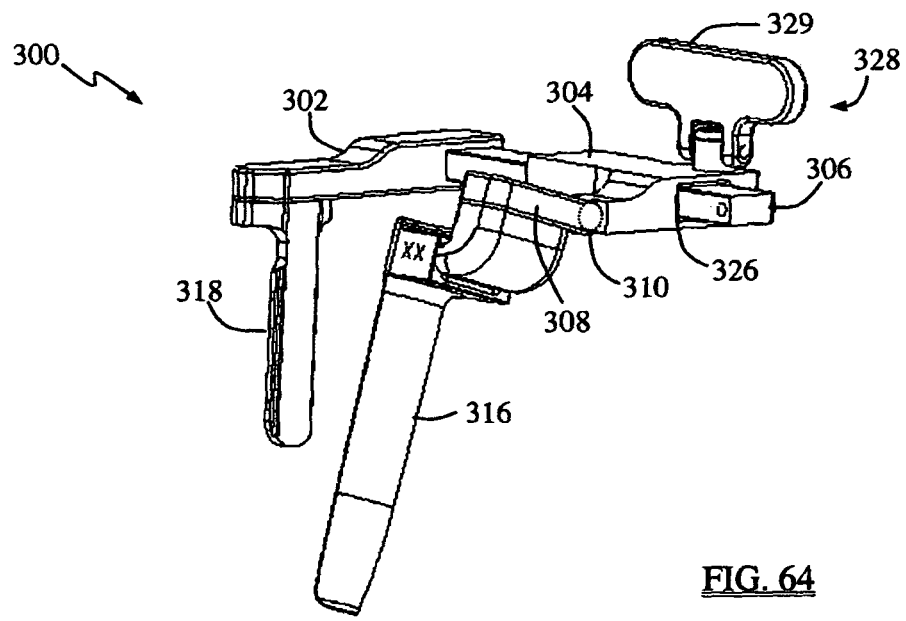
Figure 65:
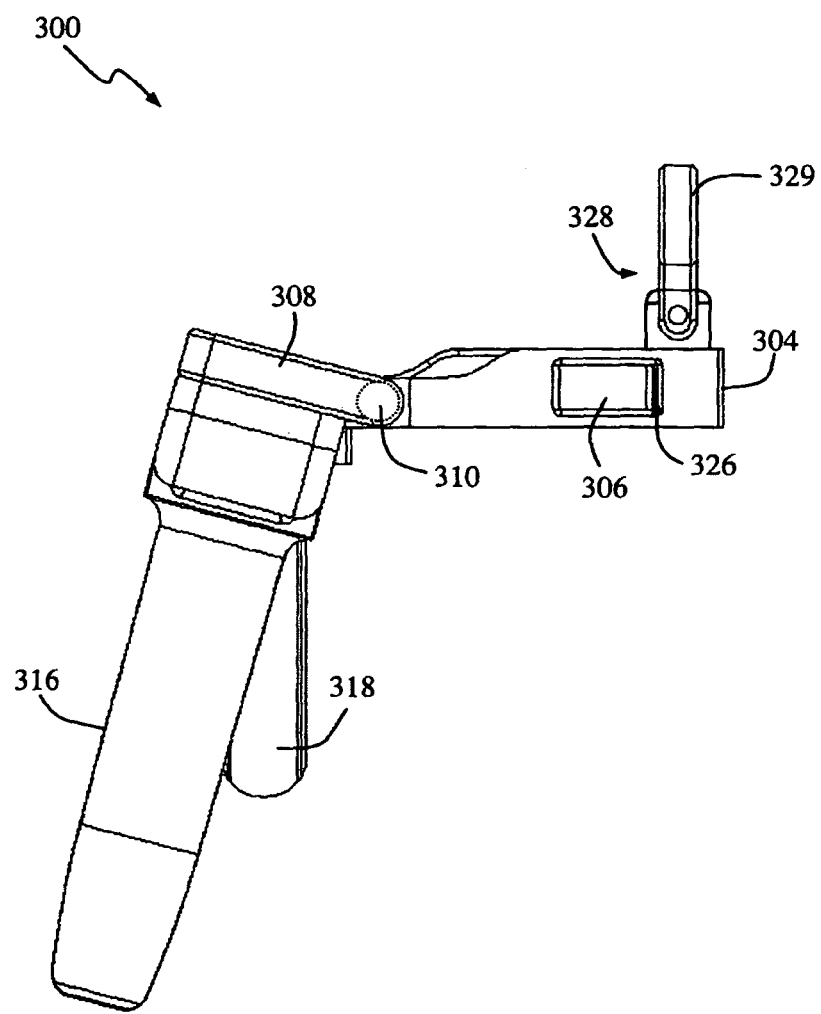
Figure 73:
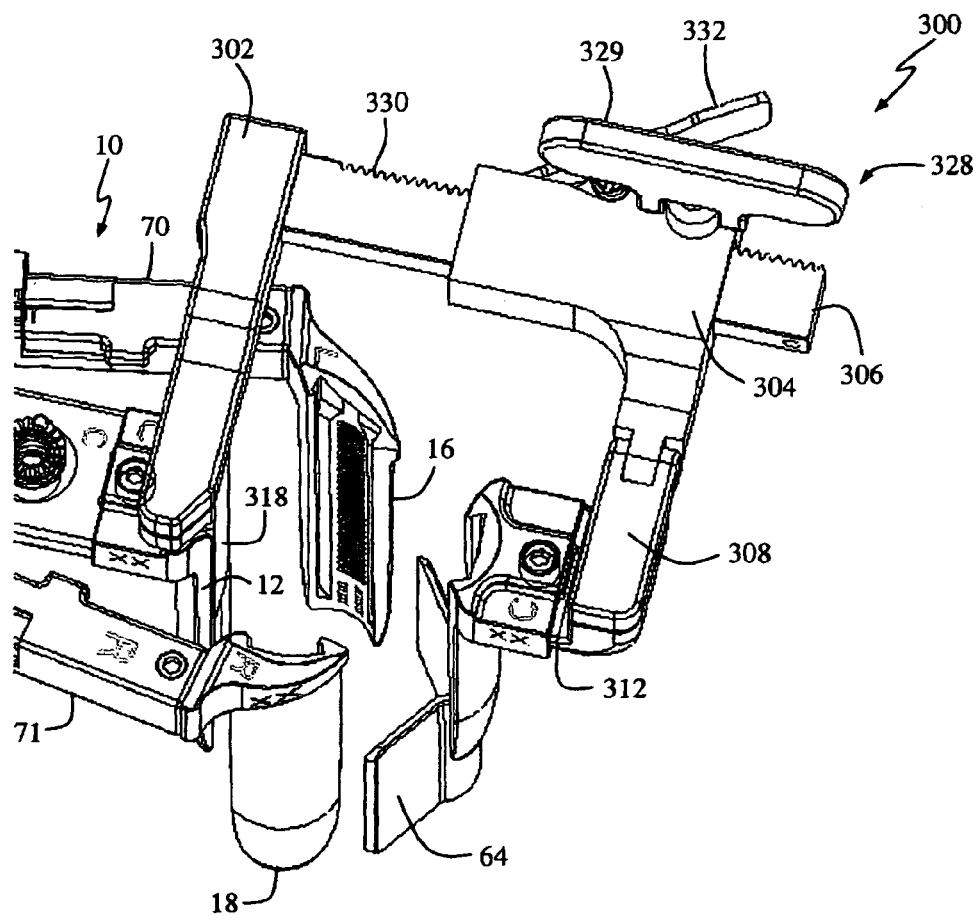
FIGS. 73-75 are perspective, top, and side views of the supplemental blade assembly of FIG. 63 mated with the retractor assembly of FIG. 5 wherein a supplemental retractor blade is outfitted with a retractor extender.
Figure 74:
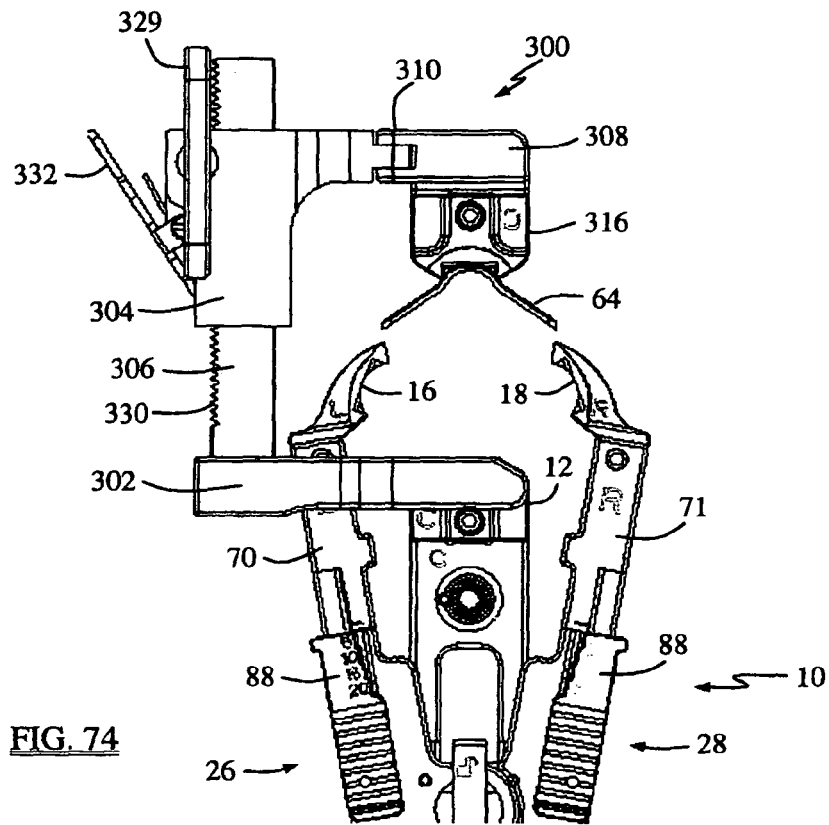
Figure 75:
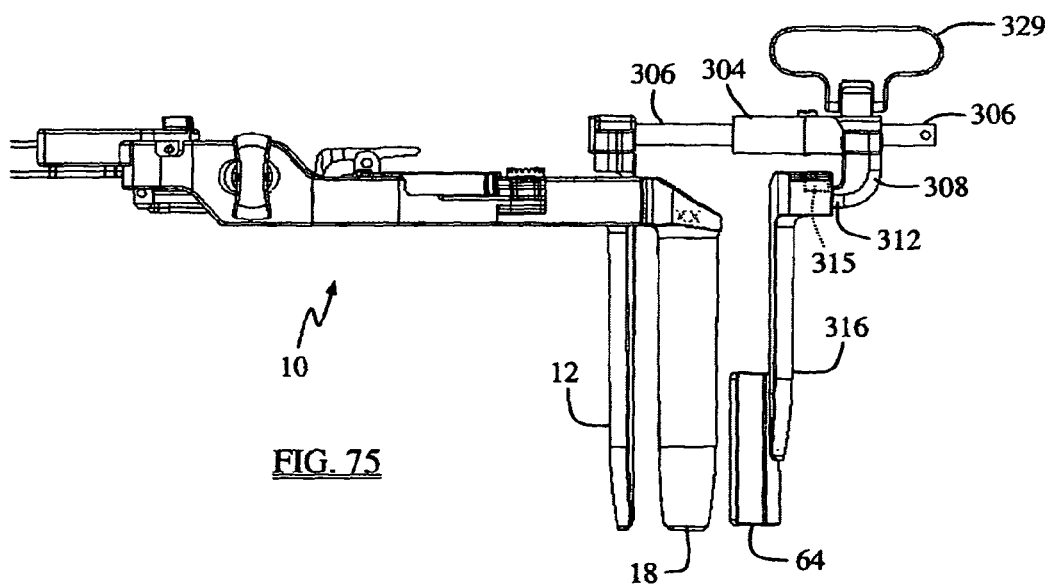

As illustrated in FIGS. 61-62, supplemental blade assembly 300 comprises a support member 302, an expansion track 306 extending generally perpendicularly therefrom, and an expansion piece 304 moveably mounted on expansion track 306. Expansion piece 304 further includes a pivot arm 308 attached thereto via pivot joint 310. Pivot arm 308 further includes an engagement platform 312 having a blade aperture 314 for engaging with the proximal end of a supplemental retractor blade 316. The proximal end of supplemental retractor blade 316 rests on engagement platform 312 while a protrusion 315 positioned on the proximal end interacts with the blade aperture 314 in a male-female relationship, thereby securing supplemental retractor blade 316 to pivot arm 308. As previously discussed with reference to primary retractor blades 12, 16, and 18, supplemental retractor blade 316 may be composed of any material suitable for introduction into the human body, including but not necessarily limited to aluminum, titanium, and/or clear polycarbonate that would ensure rigidity during tissue retraction. The supplemental retractor blade 316 may be optionally coated with a carbon fiber reinforced coating to increase strength and durability. The supplemental retractor blade 316 may be optionally constructed from partially or wholly radiolucent materials (e.g. aluminum, PEEK, carbon-fiber, and titanium) to improve the visibility of the surgeon during imaging (e.g. radiographic, MRI, CT, fluoroscope, etc. . . . ). The supplemental retractor blade 316 may also be composed of a material that would destruct when autoclaved (such as polymer containing a portion of glass particles), which may be advantageous in preventing the unauthorized re-use of blade 316 (which would be provided to the user in a sterile state). The supplemental retractor blade 316 may be provided in any number of suitable lengths, depending upon the anatomical environment, surgical approach, and length of primary retractor blades 12, 16, 18, such as (by way of example only) the range from 20 mm to 150 mm. Supplemental retractor blade 316 may be configured for use with any of retractor extenders 22, 24, 60 and/or shim element 25 in the same manner discussed above with respect to primary retractor blades 12, 16, 18 as illustrated by way of example only in FIGS. 73-75.

Figure 68:
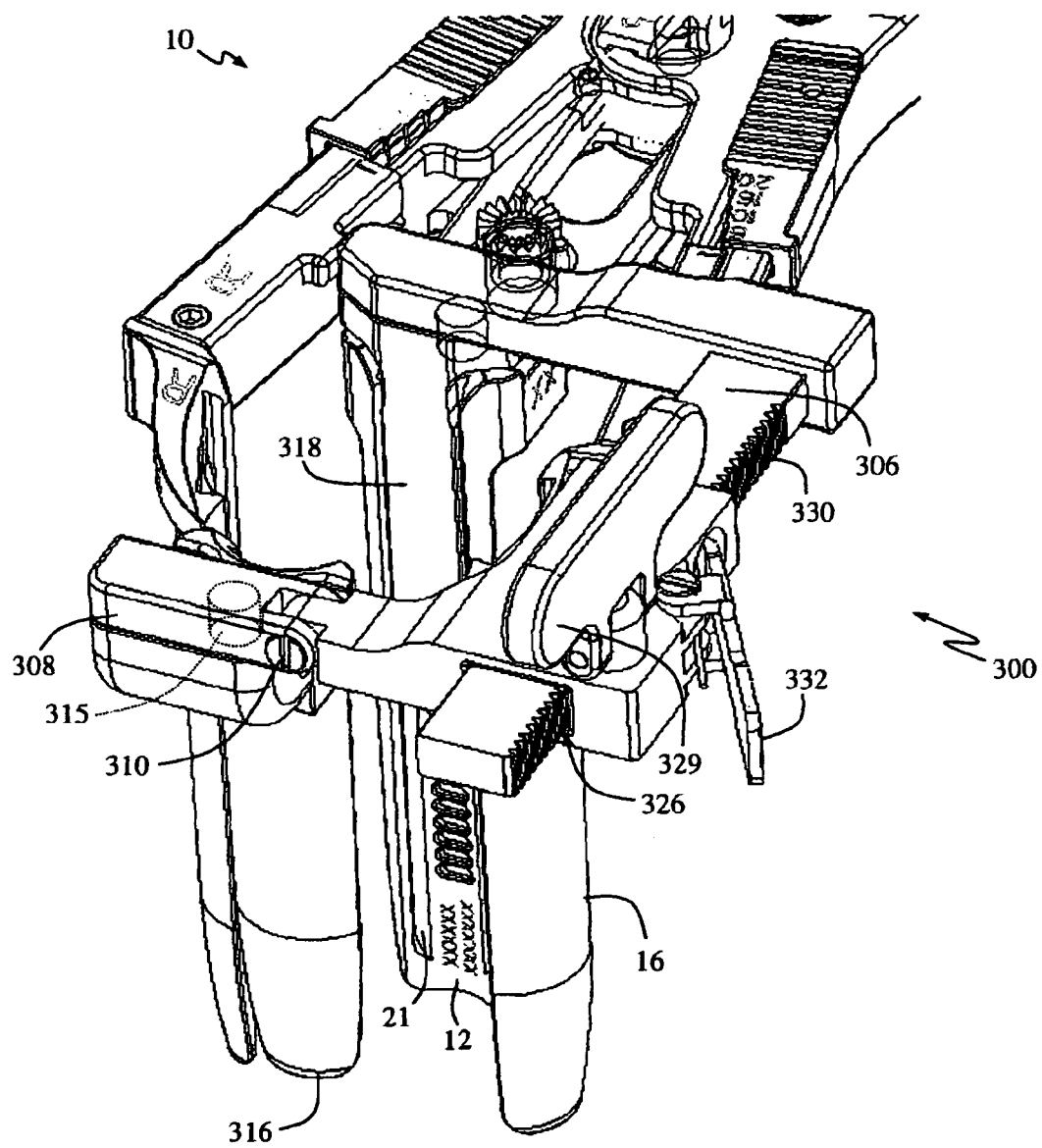
Figure 69:
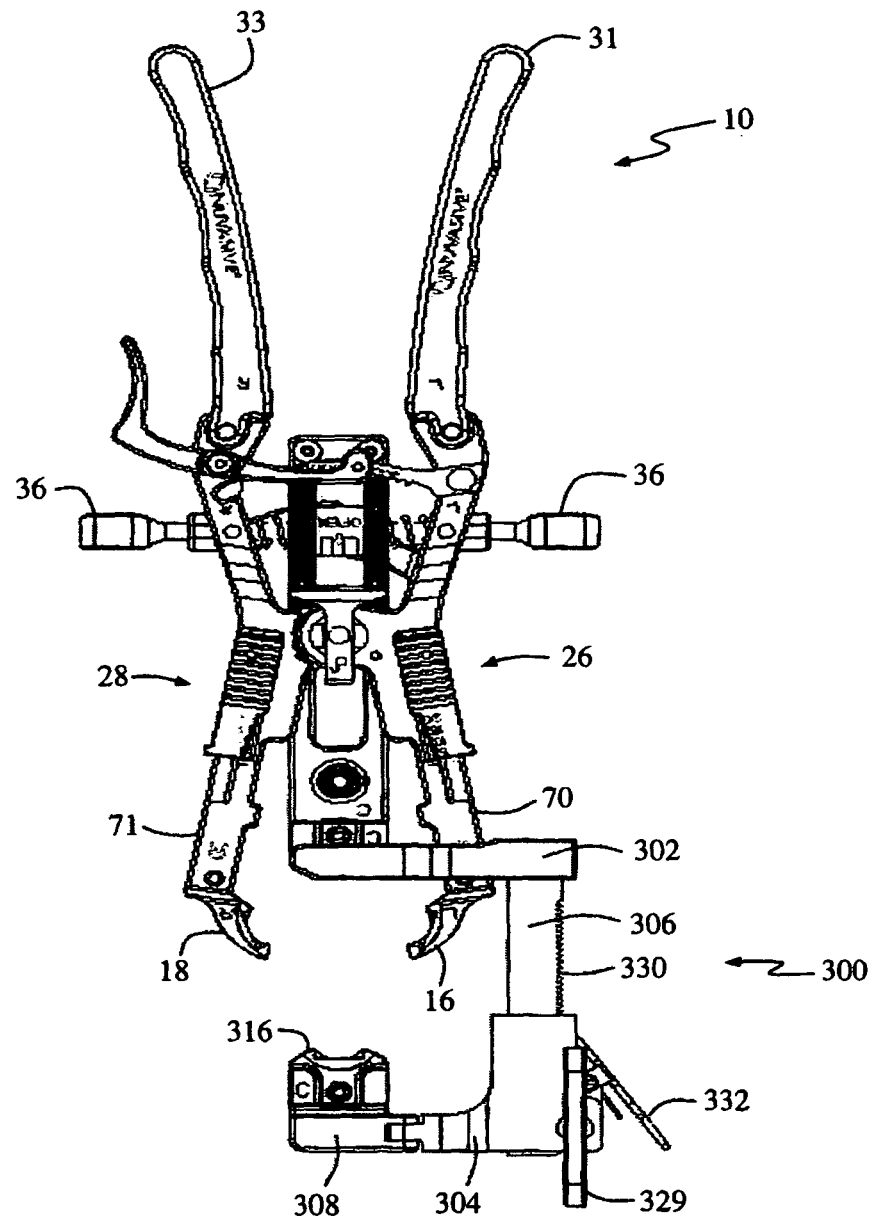
FIG. 69 is a top view of the supplemental blade assembly of FIG. 63 mated with the retractor assembly of FIG. 5.
Figure 70:
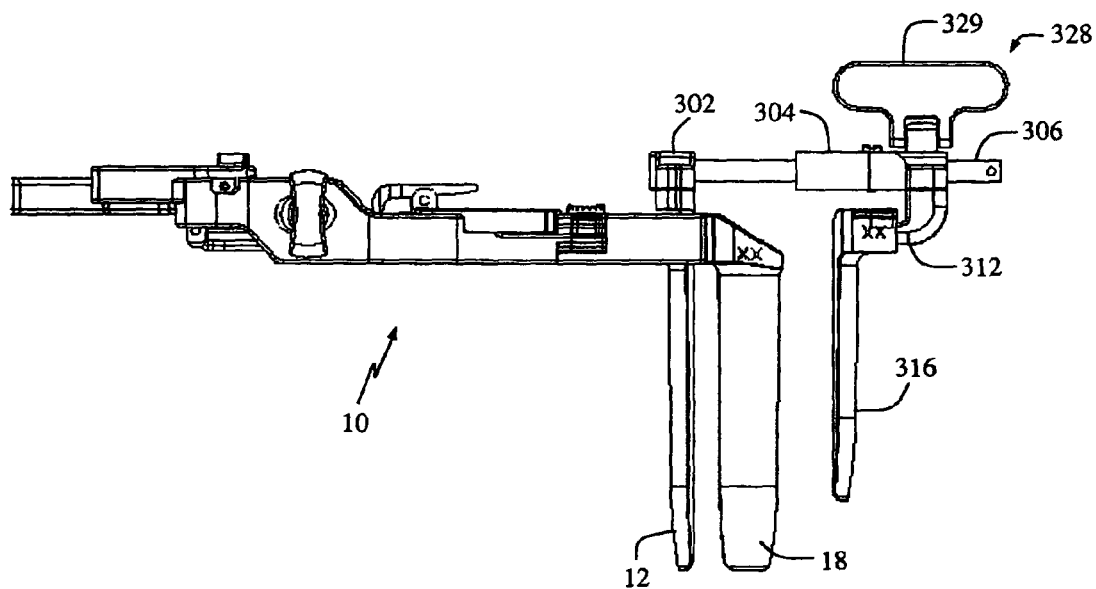
FIG. 70 is a side view of the supplemental blade assembly of FIG. 63 mated with the retractor assembly of FIG. 5.

As illustrated in FIGS. 61-62, support member 302 further includes a mating extension 318 which extends inferiorly from a first end of the support member 302. The mating extension 318 is configured to engage with receiving portions 21 which form a mating slot 322 on the interior aspect of primary retractor blade 12, as best viewed in FIG. 66. In use, mating extension 318 may be slidably engaged within mating slot 322 so as to affix supplemental blade assembly 300 to primary retractor blade 12 and thus retractor assembly 10. When fully engaged with the retractor assembly 10, the support member 302 extends laterally beyond and above one of arm members 26, 28 so as not to obstruct the operating corridor created by retractor assembly 10. Expansion track 306 extends generally perpendicularly from a second end of support member 302. When the supplemental blade assembly 300 is positioned during use in a lateral access procedure, the expansion track 306 will extend in an anterior direction from the support member 302. Expansion piece 304 includes an aperture 326 extending therethrough and dimensioned to receive the expansion track 306. Expansion piece 304 is moveably mounted on expansion track 306 by way of the interaction between the expansion track 306 and the aperture 326. A migration knob 328 positioned on expansion piece 304 includes a handle portion 329 and an inferior portion (not shown) extending into aperture 326. Within the aperture 326, engagement features on the inferior portion of migration knob 328 engage corresponding engagement features 330 on expansion track 306 such that rotation of the migration knob 328 (via rotation of handle portion 329) causes expansion piece 304 to move along the expansion track 306 in either a positive (i.e. away from support member 302) or negative (i.e. toward support member 302) direction. In one embodiment, engagement features 330 may consist of a plurality of tooth-like protrusions having a generally triangular cross section. A spring biased restriction member 332 (best viewed in FIG. 68) also engages with engagement features 330 as expansion piece 304 migrates along expansion track 306. With the restriction member 332 engaged, expansion piece 304 is prevented from moving along expansion track 306 in a negative direction. Manually depressing restriction member 332 disengages the restriction member 332 from the engagement features 330 allowing negative movement of the expansion piece 304 if necessary. Pivot arm 308 extends generally perpendicularly from expansion piece 304 (and is generally parallel to support member 302) such that when supplemental blade assembly 300 is mated with retractor assembly 10, supplemental retractor blade 316 will be positioned opposite primary retractor blade 12, as best viewed in FIGS. 68-69. Pivot joint 310 allows supplemental retractor blade 316 to pivot along an axis generally perpendicular to support member 302 so as to selectively position the supplemental retractor blade 316 in the most advantageous position (FIGS. 64-65 and 71-72).

Figure 66:
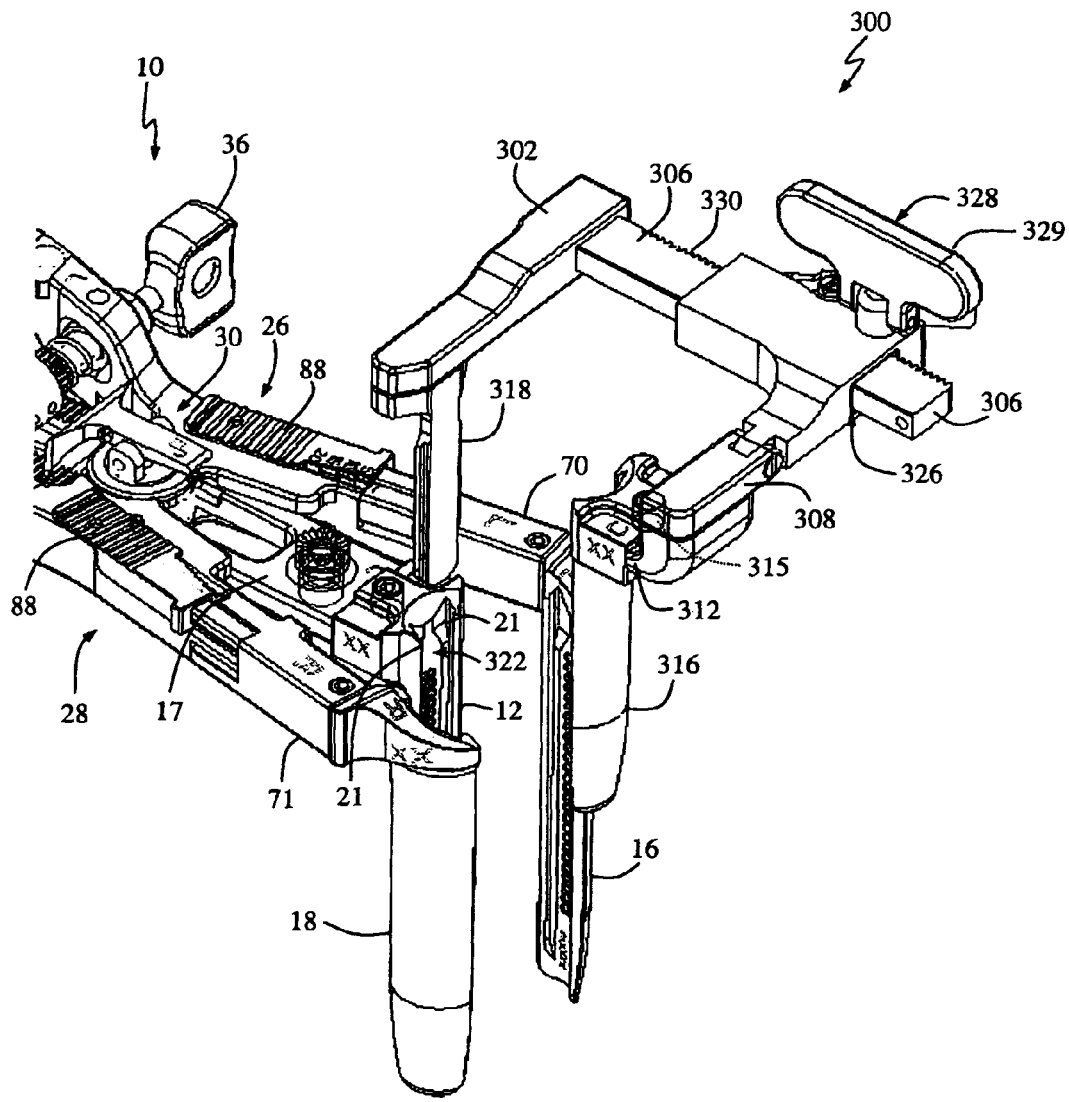
FIG. 66 is a perspective view of the supplemental blade assembly of FIG. 63 prior to being mated to the retractor assembly of FIG. 5.
Figure 67:
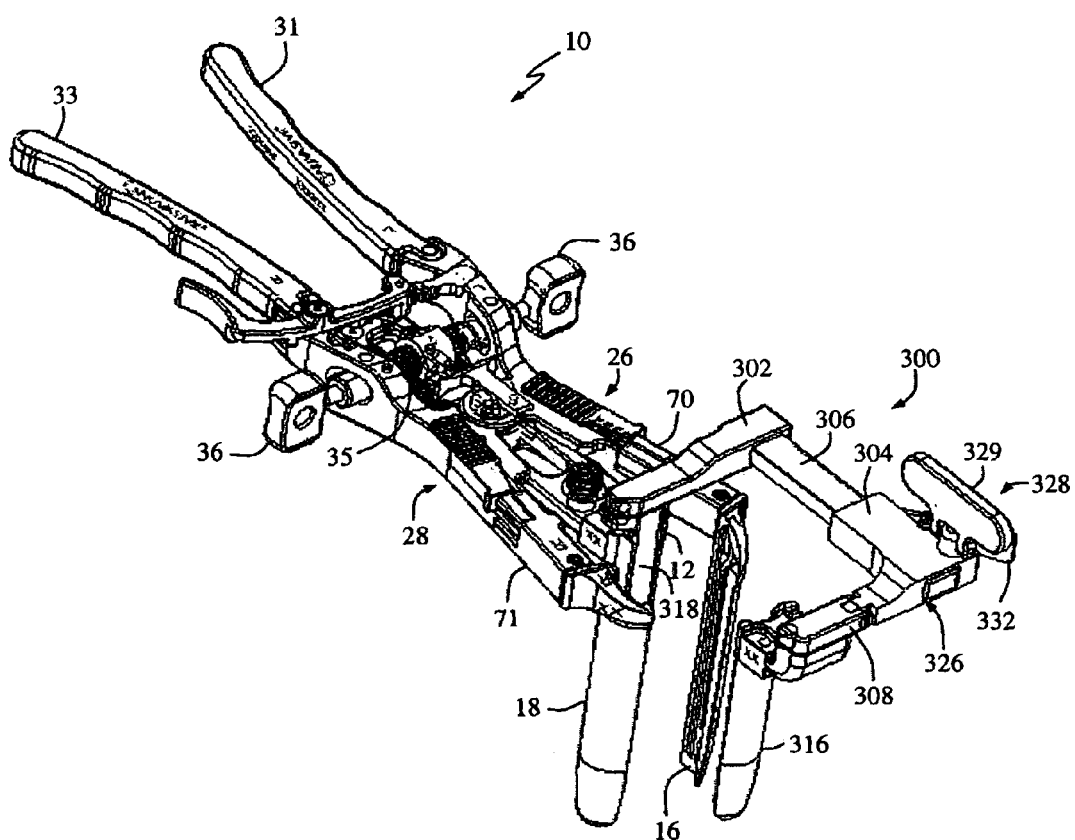
FIGS. 67-68 are perspective views of the supplemental blade assembly of FIG. 63 mated with the retractor assembly of FIG. 5 according to one embodiment of the present invention.
Figure 71:
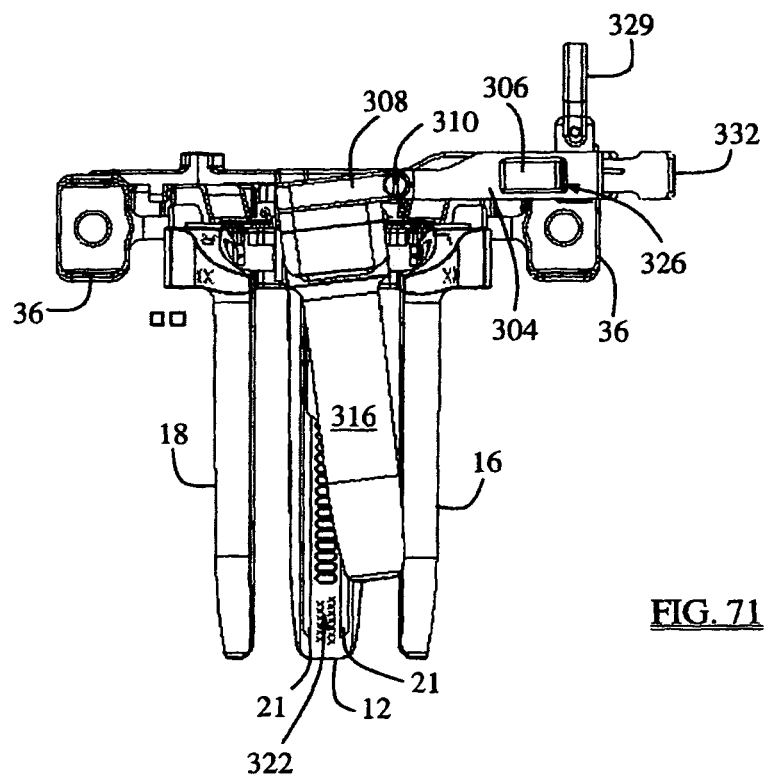
FIG. 71-72 front views of the supplemental blade assembly of FIG. 63 mated with the retractor assembly of FIG. 5 wherein a supplemental retractor blade is pivoted to a desired angular position.
Figure 72:
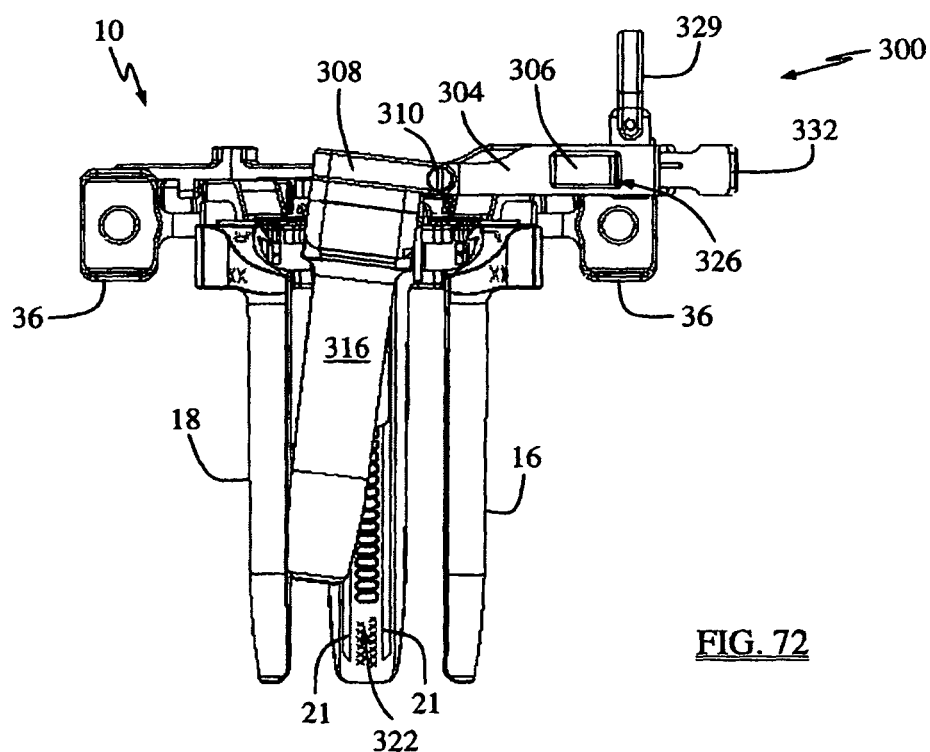

With reference to FIG. 66, a preferred method of using supplemental blade assembly 300 in conjunction with retractor assembly 10 is shown. The retractor assembly 10 is first advanced to the target site (after tissue distraction) and an initial operating corridor is formed according to the methods described above (i.e. moving retractor blades 16, 18 from a "closed" position to a "retracted" position). Once the operating corridor is created with primary retractor blades 12, 16, 18, the supplemental blade assembly 300 may be utilized to expand the operating corridor and/or provide an extra barrier to prevent ingress of body tissue into the corridor. To do so, mating extension 318 is slid into the mating slot 322 on primary retractor blade 12 to secure the supplemental assembly 300 in position. Preferably, supplemental blade assembly 300 is initially engaged to retractor assembly 10 a in a first "closed" position wherein expansion piece 304 (and hence supplemental blade 316) is in a position closet to support member 302. Next, migration knob 328 is manually rotated to advance expansion piece 302 in a positive direction along the expansion track 306 (thus retracting tissue with supplemental blade 316) until a desired "expanded" position is reached, as illustrated in FIGS. 67-70. Retractor extenders 22, 24, 60 and/or shim element 25 may be attached to supplemental retractor blade 316 (FIGS. 73-75) either before, during, or after expansion of the supplemental blade assembly 300 from the first "closed" position to the second "expanded" position. Retractor extenders 22, 24, 60, and/or shim element 25 may be utilized with respect to primary blades 12, 16, 18 as described above at any time during the procedure (i.e. before, during, and or after supplemental blade assembly 300 is introduced and expanded). Likewise, primary retractor blades 16, 18 may be selectively pivoted to a desired angulation at any time during the procedure (i.e. before, during, and or after supplemental blade assembly 300 is attached and expanded). The supplemental retractor blade 316 may be pivoted as shown in FIGS. 71-72 at any time during use, however it may be advantageous to complete such pivoting while supplemental blade assembly 300 is in the first "closed" position.

With reference now to FIGS. 76-85, there are shown examples of sequential retractor extenders 350 and 396. Sequential retractor extenders 350 and 396 extend from one or more of the retractor blades 12, 16, and 18 and supplemental retractor blade 316 to form a protective barrier to prevent the ingress or egress of instruments or biological structures (e.g. nerves, vasculature, organs, etc.). Sequential retractor extenders provide a large barrier area for blocking tissue ingress into the surgical corridor created by retraction assembly 10 but permit easy insertion through confined spaces. By way of example, the sequential retractor extenders 350 and 396 are particularly well suited for surgical procedures performed in the thoracic and thoracolumbar areas of the spine where access requires traversing the rib cage. In such a procedure, the large barrier area prevents the lung from entering the access corridor but can be easily inserted through the ribs. Sequential retractor extenders 350 and 396 may be made out any material suitable for use in the human body, including but not limited to biologically compatible plastic and/or metal, preferably partially or wholly radiolucent in nature material (such as aluminum, PEEK, carbon-fibers and titanium). The sequential retractor extenders 350 and 396 may be composed of a material that would destruct when autoclaved (such as polymer containing a portion of glass particles), which may be advantageous in preventing the unauthorized re-use of the sequential retractor extenders (which would be provided to the user in a sterile state).

FIGS. 76-78 illustrate the sequential retractor extender 350 according to one example. Sequential retractor extender 350 includes a first extender slide 352, a second extender slide 354, and an extension base 356. Extension base 356 is configured to releasably engage with one of retractor blades 12, 16, and 18 and supplemental retractor blade 316. In turn, first and second extender slides 352, 354 releasably engage with extender base 356. The edges on the back side 358 of extension base 356 form engagement elements 37 dimensioned to engage with the receiving portions 21 on the selected retractor blade(s) of blades 12, 16, 18, and 316. By way of example only, the engagement element 37 may have a generally dovetailed cross-sectional shape. Tab member 27 is equipped with an enlarged tooth 49 which engages within corresponding grooves 29 provided along the inner surface of the retractor blades 12, 16, 16, and 316 (as previously described with reference to retractor extenders 22, 24, and 60). The front side 360 of extension base 356 includes a pair of side-by-side guide channels including first guide channel 362 and second guide channel 364. Three guide rails 366 extending perpendicular to the front side 360 form the guide channels 362 and 364. The guide channels 362 and 364 are dimensioned to receive guide tracks 368 and 390 on the first and second extender slides 352, 354 respectively. A guide slot 365 located below the guide channels 362 and 364 (and bounded by retaining wall 367) receives a lower portion of guide tracks 368 and 390 while an upper tooth 369 engages an upper portion of guide tracks 368 and 390 to retain the extender slides 352, 354 in position.

Figure 117:
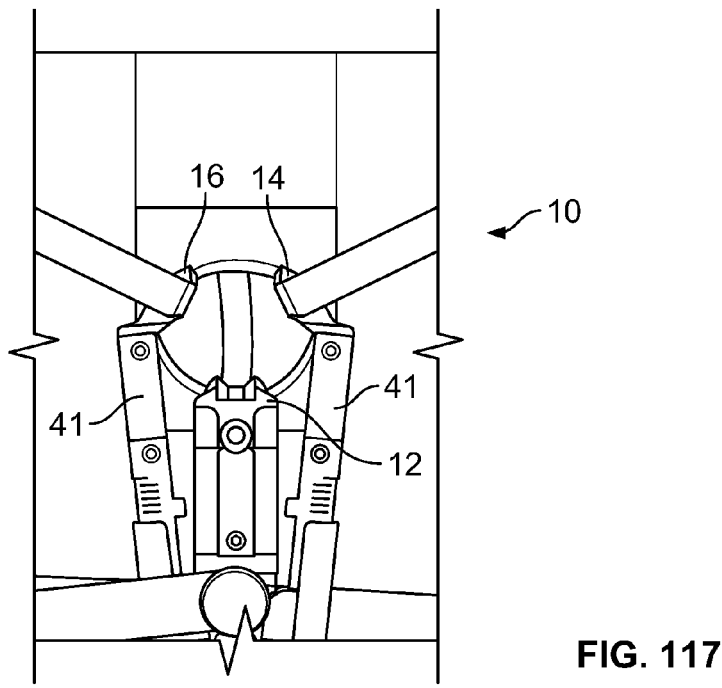

FIGS. 132-137 illustrate embodiments of arm extension 41, 141. The arm extensions 41, 141 may be attached to the retractor assembly 10 and are used to increase the size of the exposure area (FIG. 117). This allows the retractor assembly 10 to be modular, thus allowing a single retractor assembly 10 to be used to achieve a variety of sized exposure areas. This can be significant when the procedure being performed is a corpectomy. Retractors generally designed for procedures requiring smaller exposures (e.g. fusions) may not have the capability to expand the exposure large enough. With the arm extensions 41, 141 however, the corpectomy procedure can be completed without the need for an additional costly retractor system.

Example embodiments of arm extensions illustrated in FIGS. 132-133 and FIGS. 135-136 are arm extensions shaped and dimensioned to couple with distal pivot members 70. As described above, each distal pivot member 70 includes a blade aperture 78, and an aperture 80. Similar to the proximal end of the retractor blade 16, the arm extensions 41, have attachment features 544 on their proximal end of a retractor blade 16, the arm extensions 41, have attachment features 544 on their proximal end that interact with the blade aperture 78 in a male-female relationship, such that an attachment feature 544 fits into the blade aperture 78. The rigidly secure an arm extension 41 to the retractor arm 26, a pin or screw (not shown may be inserted into aperture 80 and become secured into the arm aperture 543. The arm extensions illustrated in FIGS. 134 and 137 also have attachment features 544, but they attach to a translating member 17, which is coupled to the handle assembly 20 (similar to what is described above for attaching the first retractor blade 12 to the translating member 17).

FIG. 78A illustrates the front side 370 of the first extender slide 352. FIG. 78B illustrates the back side 372 of first extender slide 352. Extender slide 352 includes a center stem 374 and an offset barrier arm 376. Guide track 368 extends generally perpendicularly from the center stem 374 on the back side of the first slide extender 352. A lower extension 378 is dimensioned to slide through guide channel 362 and into guide slot 365 behind retaining wall 367. As lower extension 378 is fully received in guide slot 365, upper extension 380 on guide track 368 snaps behind the upper tooth 369, thereby fixing the first extender slide 352 to the extension base 356. To remove the first extender slide 352, the user may simply apply forward pressure (i.e. away from the retractor blade) to disengage the upper extension 380 from behind the upper tooth 369 and then slide the lower extension out of guide slot 365, pulling up until the slide extender 352 is fully removed. Barrier arm 376 is offset from center stem 374 and angles toward the back side 372 before extending out laterally such that the barrier arm generally aligns with the front of the retractor blade.

FIG. 79A illustrates the front side 382 of the second extender slide 354. FIG. 79B illustrates the back side 384 of second extender slide 354. Extender slide 354 includes a center stem 386 and an offset barrier arm 388. Guide track 390 extends generally perpendicularly from the center stem 386 on the back side of the second slide extender 354. A lower extension 392 is dimensioned to slide through guide channel 362 and into guide slot 365 behind retaining wall 367. As lower extension 392 is fully received in guide slot 365, upper extension 394 on guide track 390 snaps behind the upper tooth 369, thereby fixing the second extender slide 354 to the extension base 356. To remove the second extender slide 354, the user may simply apply forward pressure (i.e. away from the retractor blade) to disengage the upper extension 394 from behind the upper tooth 369 and then slide the lower extension out of guide slot 365, pulling up until the slide extender 354 is fully removed. Barrier arm 388 is offset from center stem 386 and angles toward the back side 384 before extending out laterally such that the barrier arm generally aligns with the front of the retractor blade.

Figure 80A:
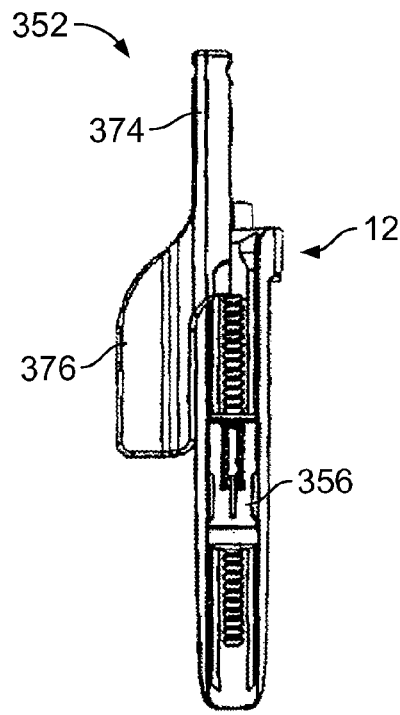
FIGS. 80A-80D are front views of the sequential retractor extender of FIG. 76 being sequentially engaged to the center retractor blade of FIG. 1.
Figure 80B:
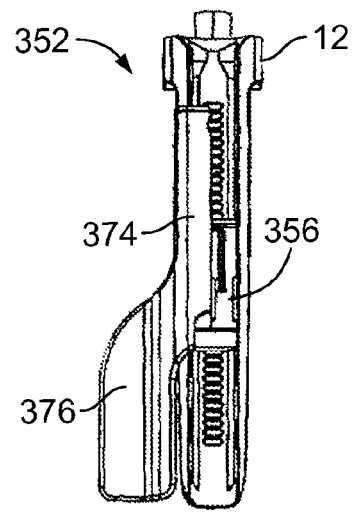
Figure 80C:
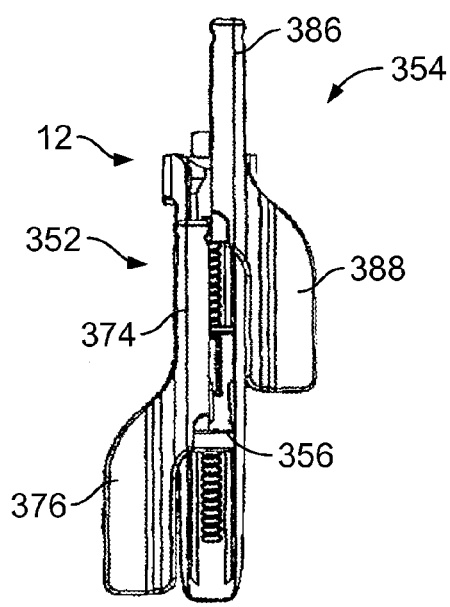
Figure 80D:
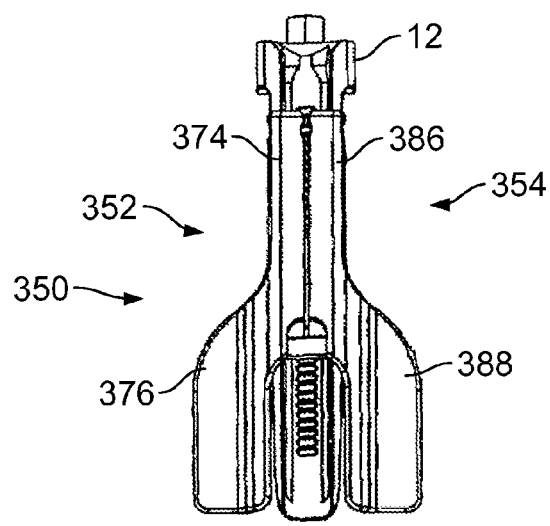

Turning to FIGS. 80A-80D; insertion of the sequential retractor extender 350 is illustrated. While FIGS. 80A-80D show the sequential retractor extender 350 being used in connection with retractor blade 12, it will be appreciated that the sequential retractor extender 350 may be used with any of blades 12, 14, 16, and supplemental blade 316 described above. Furthermore, while blade 12 is illustrated by itself (i.e. detached from retractor assembly 10) for the purposes of clarity, it is to be appreciated that the sequential retractor extender 350 is preferably intended to be inserted after the retractor blades of the retractor assembly 10 are advanced to the surgical target site. FIG. 80A illustrates the extension base 356 engaged within the receiving portions 21 of the blade 12 with tooth 49 engaged with the groove 29. The first extender slide 352 is advanced to the blade (manipulating the orientation of the slide 352 as needed, for example, to pass the barrier arm 376 between a pair of ribs) until the guide track 368 lines up with the appropriate guide channel 366. The extender slide 352 is then advanced downward until the lower extension 378 of guide track 368 is captured in guide slot 365 and upper extension 380 is engaged behind upper tooth 369, as shown in FIG. 80B. With the first extender slide 352 fixed in position, the second extender slide 354 is advanced to the blade (again manipulating the orientation of the slide 354 as needed, for example, to pass the barrier arm 388 between a pair of ribs) until the guide track 390 lines up with the appropriate guide channel 366 (FIG. 80C). The extender slide 354 is then advanced downward until the lower extension 392 of guide track 390 is captured in guide slot 365 and upper extension 394 is engaged behind upper tooth 369, as shown in FIG. 80D.

FIGS. 81-84 illustrate the sequential retractor extender 396 according to another example. Sequential retractor extender 396 includes a first extender slide 398 and a second extender slide 400. First and second extender slides 398 and 400 are configured to engage with one of retractor blades 12, 16, and 18 and supplemental retractor blade 316. FIG. 81 illustrates the front side of sequential retractor extender 396 while FIG. 82 illustrates the back side of retractor extender 396. FIG. 83 illustrates the back side 402 of first extender slide 398 and FIG. 84 illustrates the back side 417 of second extender slide 400. First extender slide 398 includes a center stem 404 and an offset barrier arm 406. A guide track 408 extends generally perpendicularly from the center stem 404 on the back side 402 of the first slide extender 398. Along a majority of the length of guide track 408 the width is such that it is approximately half of the receiving portion 21 of the selected retractor blade. The uppermost portion of guide track 408 extends to form engaging element 410 adapted to be slidably captured within the receiving portions 21 of the retractor blade. Barrier arm 406 is offset from center stem 404 and angles toward the back side 402 before extending out laterally such that the barrier arm generally aligns with the front of the retractor blade. Second extender slide 400 includes a center stem 412 and an offset barrier arm 414. A guide track 416 extends generally perpendicularly from the center stem 412 on the back side 417 of the second extender slide 400. Along a majority of the length of guide track 416 the width is such that it is approximately half the width of the receiving portions 21 of the selected retractor blade such that both guide track 408 of the first extender slide 398 and guide track 416 fit side-by-side within the receiving portion 21. The uppermost portion of guide track 416 extends to form engaging element 418 adapted to be slidably captured within the receiving portion 21 of the selected retractor blade. The length of the guide track 416 of second extender slide 400 is longer than the length of the guide track 408 of the first extender slide 398 such that the engaging element 418 of the second slide 400 rests on top of the engaging element 410 of first slide 398 when the extender slides are engaged with one of retractor blades 12, 14, 16, and 316. In a preferred embodiment, the first engaging element 410 may have a different shape, for example only triangular as depicted, than the second engaging element 418 (depicted by way of example as rectangular) such that the slides are easily distinguishable. Barrier arm 414 is offset from center stem 412 and angles toward the back side 417 before extending out laterally such that the barrier arm 414 generally aligns with the front of the retractor blade.

Figure 85A:
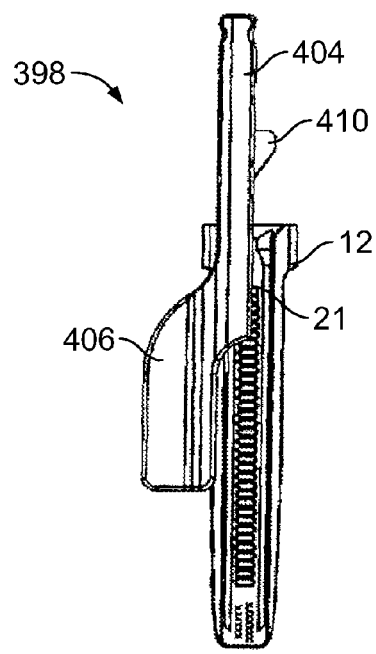
FIGS. 85A-85D are front views of the sequential retractor extender of FIG. 81 being sequentially engaged to the center retractor blade of FIG. 1.
Figure 85B:
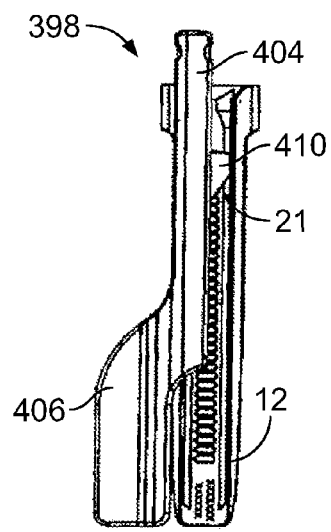
Figure 85C:
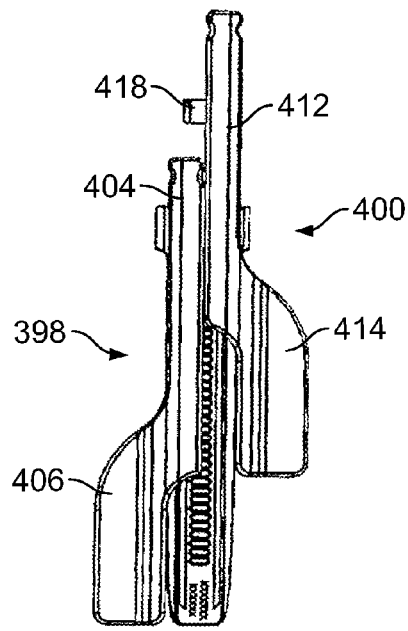
Figure 85D:
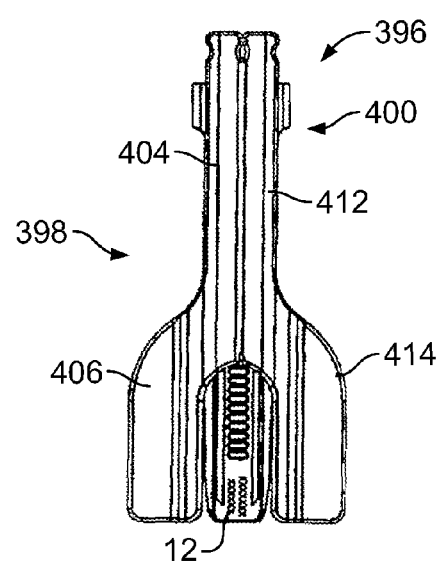

In FIGS. 85A-85D, the sequential insertion of the sequential retractor extender 396 is illustrated. While FIGS. 85A-85D show the sequential retractor extender 396 being used in connection with retractor blade 12, it will be appreciated that the sequential retractor extender 396 may be used with any of blades 12, 14, 16, and supplemental blade 316 described above. Furthermore, while blade 12 is illustrated by itself (i.e. detached from retractor assembly 10) for the purposes of clarity, it is to be appreciated that the sequential retractor extender 396 is preferably intended to be inserted after the retractor blades of the retractor assembly 10 are advanced to the surgical target site. FIG. 85A illustrates the first extender slide 398 being advanced to the blade (manipulating the orientation of the slide 398 as needed, for example, to pass the barrier arm 406 between a pair of ribs) until the engaging element 410 is slidably captured within the receiving portion 21 of the retractor blade 12 and advanced to a desired position (FIG. 85B). With the first extender slide 398 in position, the second extender slide 400 is advanced to the blade 12 (again manipulating the orientation of the slide 400 as needed, for example, to pass the barrier arm 414 between a pair of ribs) (FIG. 85C) until the engaging element 418 is slidably captured within the receiving portion 21 of the retractor blade 12 and advanced to a desired position (FIG. 85D).

With reference now to FIGS. 86-89, there is shown an example embodiment of an expandable retractor extender 420. The expandable retractor extenders 420 extends from one or more of the retractor blades 12, 16, and 18 and supplemental retractor blade 316 to form a protective barrier to prevent the ingress or egress of instruments or biological structures (e.g. nerves, vasculature, organs, etc.). Much like the sequential retractor extenders 350 and 396, the expandable retractor extender 420 provides a large barrier area for blocking tissue ingress into the surgical corridor created by retraction assembly 10 but permits easy insertion through confined spaces. By way of example, the expandable retractor extender 420 is particularly well suited for surgical procedures performed in the thoracic and thoracolumbar areas of the spine where access requires traversing the rib cage. In such a procedure, the large barrier area prevents the lung from entering the access corridor but can be easily inserted through the ribs.

Figure 86:
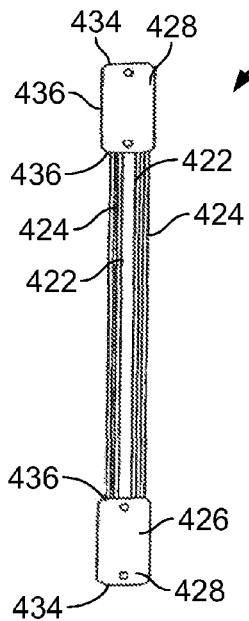
FIGS. 86-87 are front and side views, respectively, of an expanding retractor extender in a natural position, according to one example embodiment.
Figure 87:
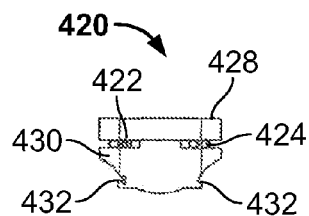
Figure 88:
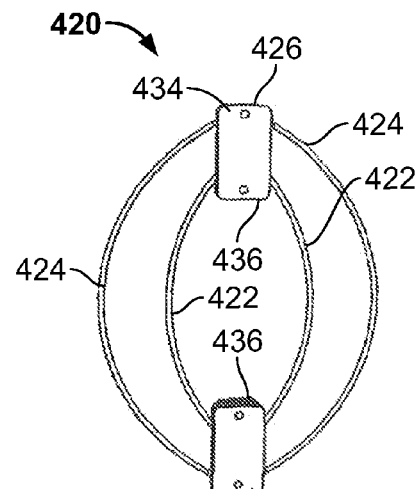
FIGS. 88-89 are front and side views, respectively, of an expanding retractor extender according to FIG. 86 in an expanded position.
Figure 89:
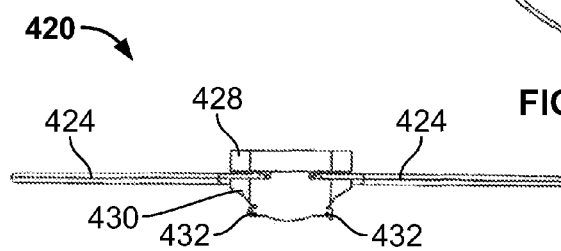

FIG. 86 depicts the expandable retractor extender 420 in a first natural position. Expandable retractor extender 420 a pair of inner wires 422 and a pair of outer wires 424 captured each end within endplates 426. End plates 426 have a forward plate 428 and rear plate 430. The rear plates 430 of endplates 426 are configured to be slidably captured within the receiving portion 21 of any of retractor blades 12, 14, 16, and 316. By way of example, the back edges on the rear plate 430 form engagement elements 432 dimensioned to engage with the receiving portions 21 on the selected retractor blade(s) of blades 12, 16, 18, and 316. By way of example only, the engagement element 432 may have a generally dove-tailed cross-sectional shape. Endplates 426 also have an outer end 434 and an inner end 436. The ends of inner wires 422 and outer wires 424 are captured between the forward plate 428 and rear plate 430 such that the ends cannot be removed from between the plates. Preferably, the ends are movably captured such that they can rotate between the plates 428 and 430. Inner wires 422 are shorter than outer wires 424 and are captured near the inner end 436. Outer wires 424 are captured near the outer ends 434. The inner wires 422 and outer wires 424 are preferably constructed from polymer or thin metal material with characteristics that allow the wires to bend and bow outward when the distance between the endplates 426 is reduced. Endplates 426 may be constructed from any material suitable for use in the human body, including but not limited to biologically compatible plastic and/or metal, preferably partially or wholly radiolucent in nature material (such as aluminum, PEEK, carbon-fibers and titanium). The endplates 426 and or wires 422, 424, may be composed of a material that would destruct when autoclaved (such as polymer containing a portion of glass particles), which may be advantageous in preventing the unauthorized re-use of the expanding retractor extender 420 (which would be provided to the user in a sterile state).

Figure 90A:
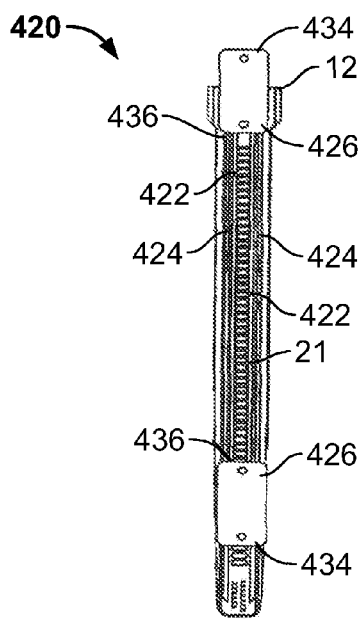
FIGS. 90A-90B are from views of the expanding retractor extender of FIG. 86 being engaged to the center retractor blade of FIG. 1 and expanded.
Figure 90B:
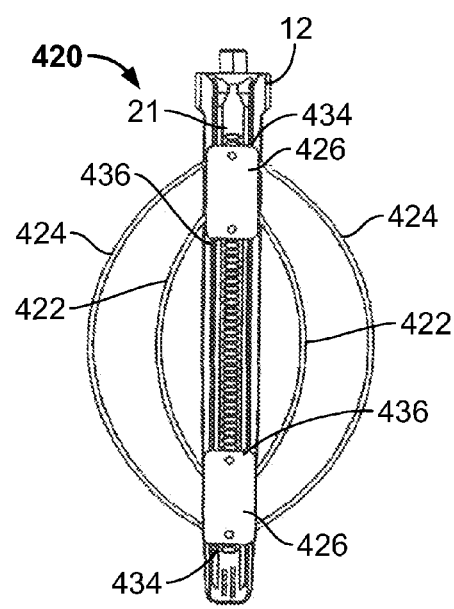

FIGS. 90A-90B demonstrate the use of expanding retractor extender 420. While FIGS. 90A-90B show the expanding retractor extender 420 being used in connection with retractor blade 12, it will be appreciated that the expanding retractor extender 420 may be used with any of blades 12, 14, 16, and supplemental blade 316 described above. Furthermore, while blade 12 is illustrated by itself (i.e. detached from retractor assembly 10) for the purposes of clarity, it is to be appreciated that the expanding retractor extender 420 is preferably intended to be inserted after the retractor blades of the retractor assembly 10 are advanced to the surgical target site. In FIG. 90A, the engagement members 432 on the rear plate 430 of one of endplates 426 are lined up and slidably inserted into the receiving portion 21 of the retractor blade 12. As the leading endplate is advanced down the receiving portion 21 of the retractor blade 12, the engagement members 432 on the trailing endplate 426 are lined up and slidably received in the receiving portion 21 of the retractor blade 12. When the leading endplate 426 reached the desired position along the retractor blade 12 advancement of the leading endplate ceases. Meanwhile, advancement of the trailing endplate continues and the distance between the trailing endplate and leading endplate is reduced. As the trailing endplate advances closer to the leading endplate the inner wire 422 pair and the outer wire pair 424 are forced to bow outward creating a tissue barrier surface. While the example embodiment has been described as having an inner pair of wires and an outer pair of wires, it is contemplated that additional pairs of wires may be added to decrease the spacing between wires in the expanded position. According to the embodiment shown, engagement elements 432 on rear plate 430 are dimensioned to frictionally engage the receiving portion 21 such that the advancement and, more importantly, retreat of the endplates requires the application of force by the user. According to an alternate embodiment (not shown) the rear plate 430 may be equipped with a tab 27 and tooth 49 configured to engage the grooves in the retractor blade as described previously.

Figure 91:
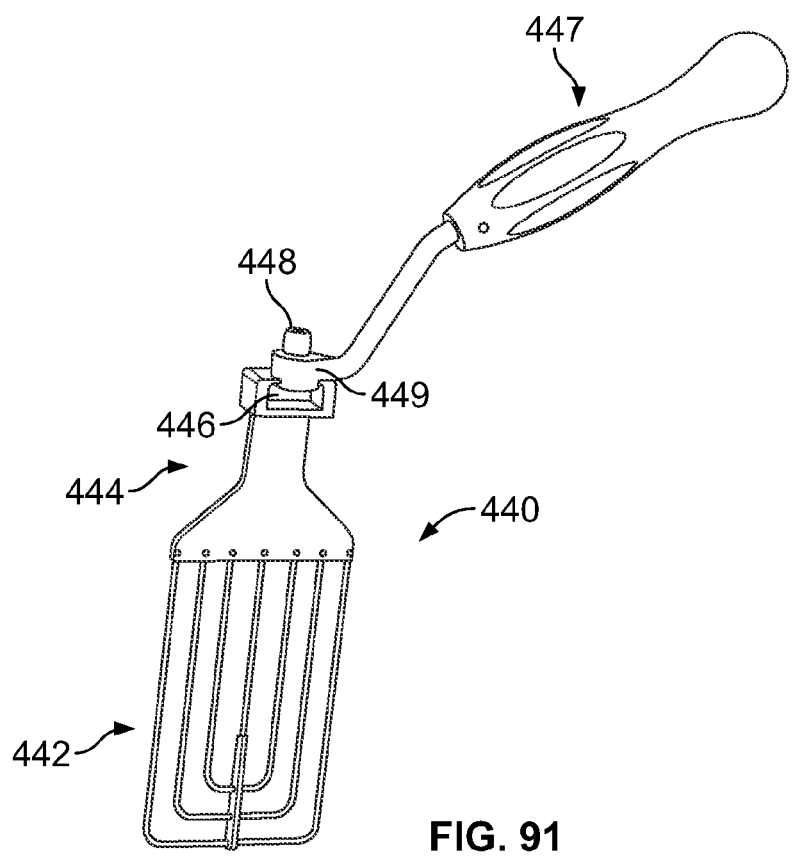
FIG. 91 is a perspective view of an alternate retractor blade configured especially for retracting lung tissue attached to a manual retractor handle, according to one example embodiment.
Figure 92:
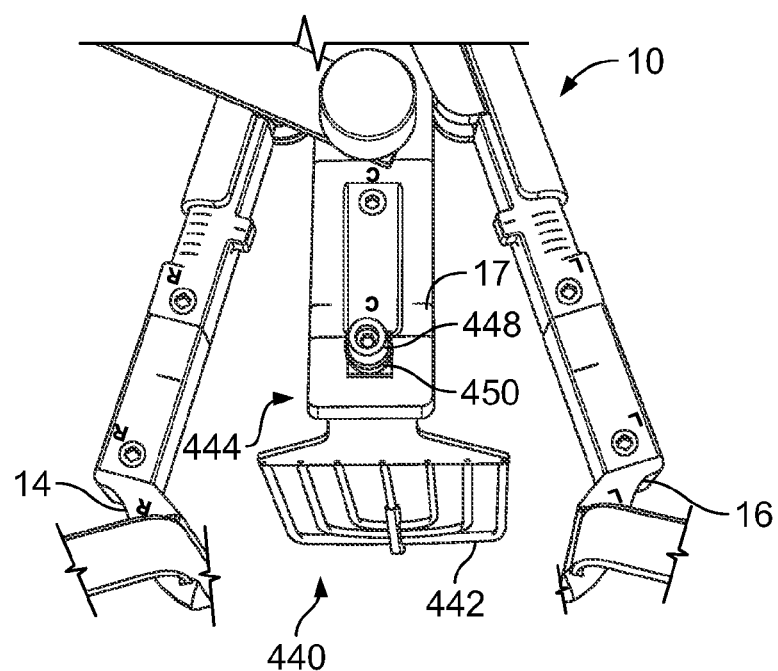
FIG. 92 is perspective view of the alternate retractor blade of FIG. 91 attached to the retractor assembly of FIG. 1 and replacing the center blade.

With reference to FIGS. 91-92 there is shown another alternate retractor blade 440 configured for use with the retractor assembly 10. In particular, the alternate retractor blade 440 is a lung retractor blade. The distal end 442 of retractor blade 440 has a wire design to allow for optimal fluoroscopy visibility. The proximal end 444 of retractor blade 440 is adapted to mate retractor blade for 440 with retractor assembly 10. To accomplish this, the proximal end of the retractor blade 440 includes an engagement cavity 446 and a set screw 448 having a distal end in communication with said cavity 446. Engagement cavity 446 is complementary in shape the engagement platform 312 on supplemental retractor assembly 300 as well as a similar platform (not shown) on translating member 17 of retractor assembly 10. According to the example shown then, alternate blade 440 may be used in place of the center blade 12 and/or the supplemental retractor blade 316. With the engagement platform of either supplemental retractor assembly 300 or translating member 17 positioned in the engagement cavity 446, the set screw 448 may be tightened to fix alternate blade in position. According to one example, the alternate blade 440 is intended to be attached to the retractor assembly 10 after the blades 14, 16 have been at least partially opened. By way of example, the retractor assembly may be advanced to the surgical target site over sequential dilation system with retractor blade 14 and retractor blade 16 in a closed position and with no blade attached to translating member 17. After opening retractor blades 14, 16, the alternate blade 440 may be advanced to the target site and thereafter attached to the retractor assembly. To accomplish this, alternate blade may be initially attached to a manual retraction handle 447. Retraction handle 447 includes a connection ring 449 configured to grasp and hold the set screw 448 and thereby leaving cavity 446 free to receive the engagement platform. According to one embodiment, a canted coil spring (not shown) is situated within an annular groove along the interior of connection ring 449. As the connection ring 449 is advanced over the setscrew the canted coil spring compresses. In its final position, the canted coil spring expands into annular groove 450 on set screw 448 and rigidly couples the handle 446 to alternate blade 440. The handle can then be used to manually retract tissue and guide the alternate blade to the translating member 17 for attachment. With the engagement platform positioned in the engagement cavity 446 the set screw may be tightened prior to disengaging the retraction handle as the annular groove 450 will travel around the canted coil spring. With the alternate blade 440 locked to the translating member 17, the retraction handle may be removed by applying upward force to cause the canted coil spring to compress and disengage the annular groove 450. The same steps may be performed to attach the alternate blade 440 to the supplemental retractor 300. Alternatively, the alternate blade 440 may be attached to the supplemental retractor prior to insertion.

Alternate blade (lung retractor) 440 has a tapered proximal end and a generally square distal end. Significantly, the generally square distal end has advantages over the typical rounded lung retractors in that the square end allows the blade 440 to generally match the lateral contour of a vertebral body and thus the blade 440 may be more intimately positioned next to a spinal disc space and particularly an anterior disc space. Having this intimate contact reduces the opportunity for tissue creep into the operative corridor. The tapered proximal end, including a slim attachment neck and angled sidewalls tapering out to meet the blade ends of the alternate blade 440 allows the blade 440 to fit under the ribs and perform its functions while being oriented transverse to the rib openings and maintaining its attachment to the attachment assembly 10. This low profile proximal end also helps to reduce tension on the skin. By way of example the attachment neck may have a length between 15 and 25 mm, and preferably 20 mm. The blade 440 may be provided in a number of lengths and widths to accommodate various patient needs. According to one example blades may be provided as "wide" blades and "narrow blades". The narrow blade may be approximately 30 mm and the wide blade 44 may be approximately 50 mm. Alternate blades 440 may be provided having lengths from approximately 100-180 mm.

The surgical retraction assembly 10 and the various components described herewith may be utilized to access various spinal target sites along the spine and through various access approaches. According to one embodiment, various methods for accessing thoracic and throacolumbar spinal target sites through a lateral approach for performing corpectomies are described below.

Figure 93:
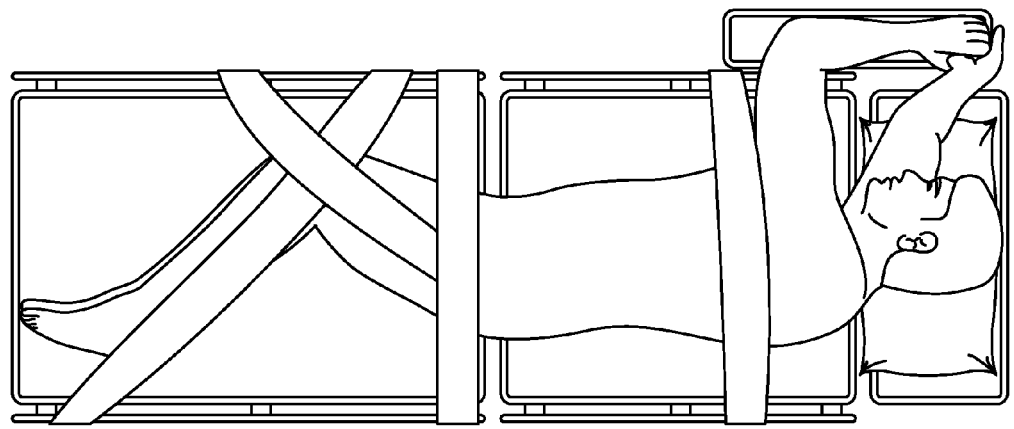
FIGS. 93-94 are figures illustrating the proper patient positioning for accessing various spinal target sites with the retractor assembly of FIG. 1.
Figure 94:
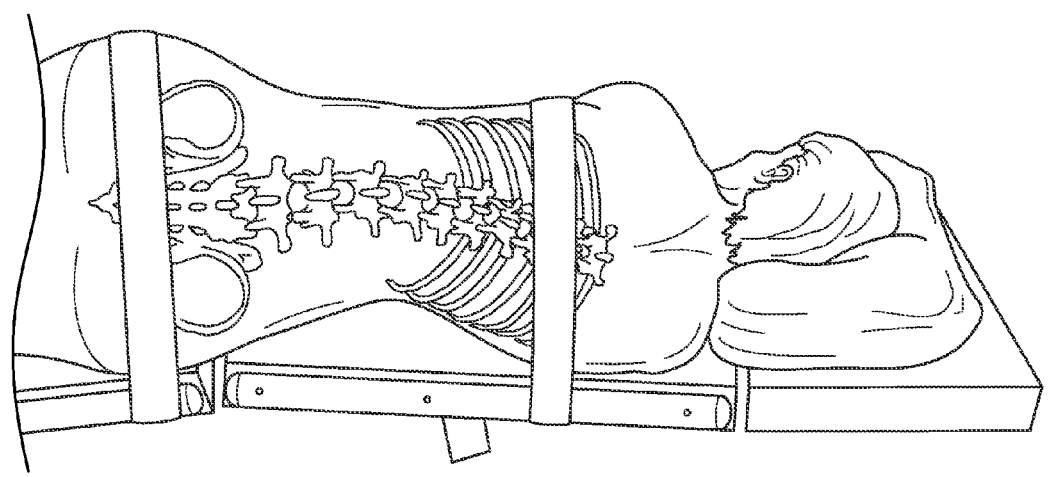

With reference to FIG. 93-94, the patient is first positioned according to a preferred position. By way of example, the patient is placed on a bendable surgical table in a direct lateral decubitus (90°) position. If the surgery involves lumbar levels (e.g., L4-L5), as well as thoracic levels, the patient is positioned so the table break is directly under the greater trochanter. If the surgery includes only thoracic levels, the patient is positioned with the table break under the mid-surgical level. The patient is then secured with tape at the following locations a) just below the iliac crest, b) over the thoracic region, c) from the iliac crest to the knee, then secured to the table, and d) from the table to the knee, past the ankle, then secured to the table. Once the patient is secured, the table should be adjusted so that the C-Arm provides true AP images when at 0° and true lateral images when at 90°.

Figure 95:
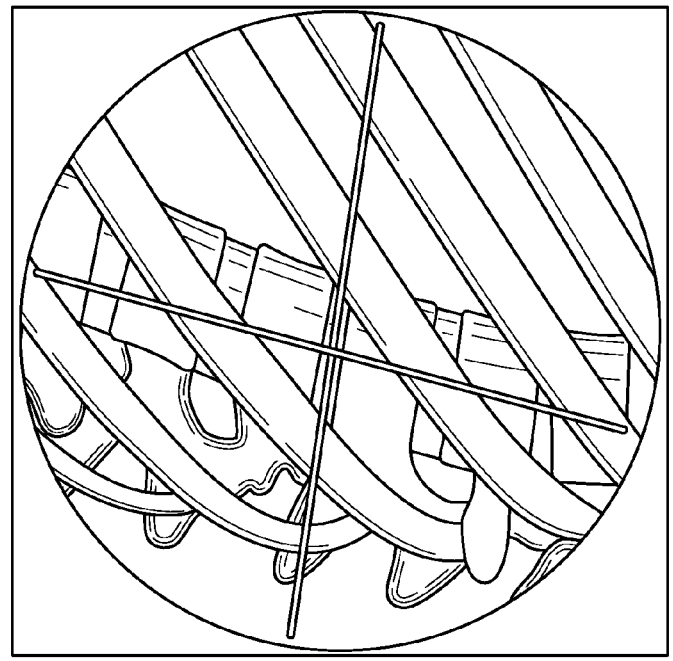

The first approach method described herein is a transpleural approach generally used for corpectomy procedures at T12 and above. With the patient properly positioned, the targeted spinal site is localized using lateral fluoroscopy. One K-wire is placed perpendicular to the spine at the level of the indicated vertebra or pathology. The other K-wire is placed parallel to the spine at the posterior middle-third of the vertebra (FIG. 95). The K-wires then used to make two marks on the skin corresponding to the K-wire positions that define the endplates of the superior and inferior vertebra. Two additional marks define the anterior and posterior margins of the vertebra to be resected. (FIG. 96).

Figure 96:
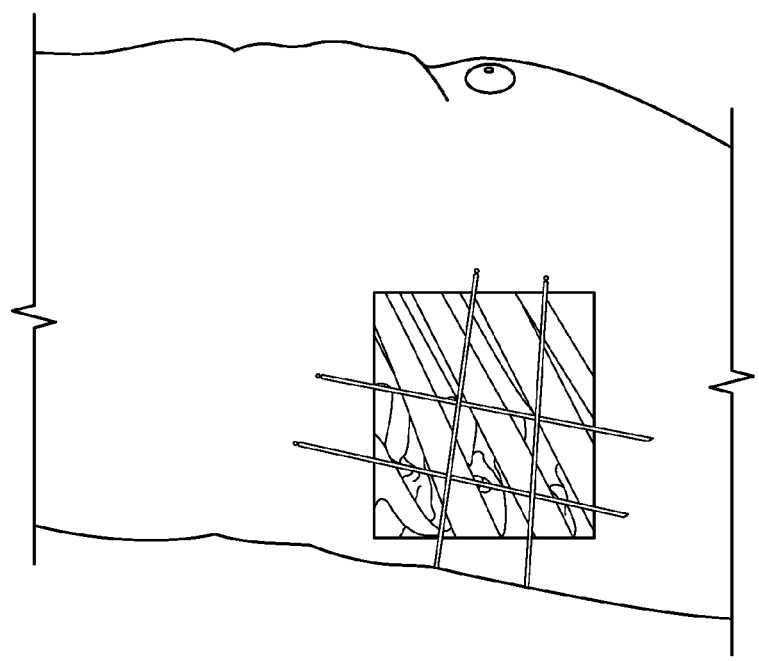
Figure 97:
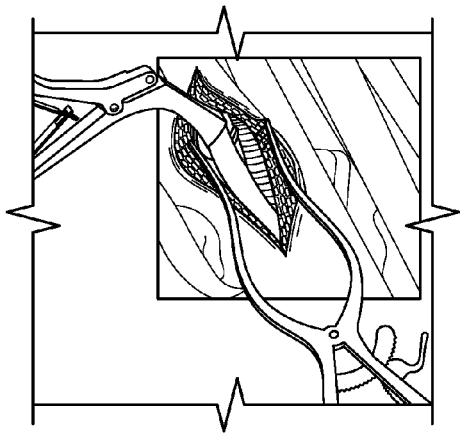

An incision is made parallel to the ribs across the region defined by the skin markings created during localization (FIG. 96). Dissection is performed through the subcutaneous tissue down to the ribs and then between the ribs through the intercostal muscles down to the pleura. An elevator/raspatory may be passed under the superior aspect of the rib to dissect the intercostal muscle off the rib, while releasing and preserving the neurovascular bundle that lies in the groove on the inferior/deep aspect of the rib. A portion of the rib (for example, ~3-5 cm) is then resected using a rib cutter or other resection instruments (FIG. 97). Entry into the pleural space is then attained using blunt hemostat dissection. While the technique described involves the resection of a small portion (~3-5 cm) of rib, alternative intercostal techniques may be utilized to preserve the rib. To do so the intercostals muscles are dissected and separated from the rib allowing the retractor assembly to pass between the ribs.

Figure 98A:
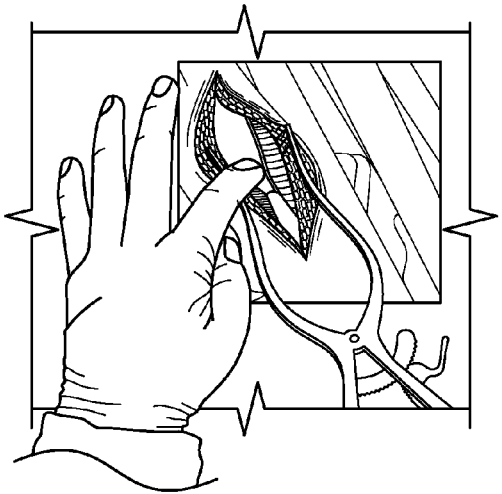
Figure 98B:
Figure 99A:
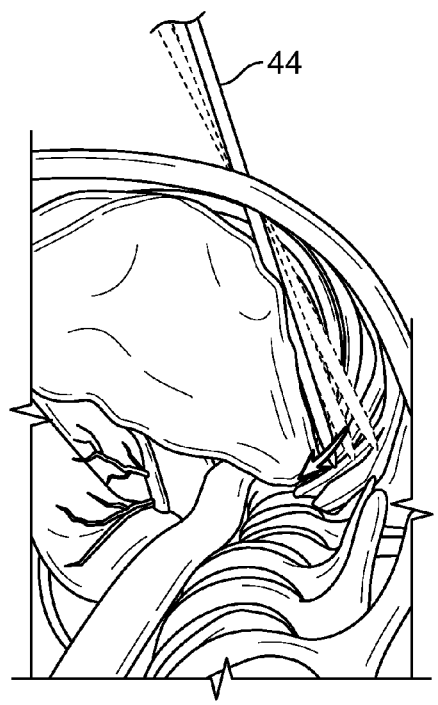
Figure 99B:
Figure 100:
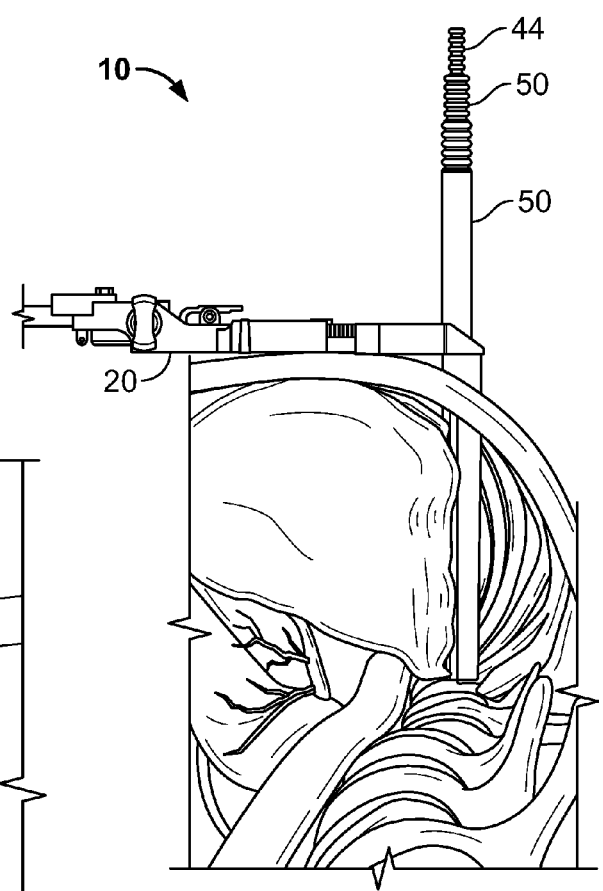

Once the parietal pleura is incised, the index finger is used to enter the pleural space and palpate the lung or diaphragm and displace the structures anteriorly (FIG. 98A-98B). The initial dilating cannula 44 is then introduced into the thoracic cavity and passed posteriorly along the ribs down to the posterior third of the targeted vertebral body (FIGS. 99A-99B). An AP fluoroscopy image may be used to confirm that the dilating cannula 44 is docked onto, and at the middle of, the targeted vertebra. The dilators of sequential dilating system 50 are subsequently passed over the initial dilating cannula 44 down to the spine (FIG. 100). Depth markings on the one or more of the initial dilating cannula 44 and sequential dilators 50 may indicate the size of the appropriate length retractor blades (12, 14, 16, 316, and/or 440) to be attached to the retractor assembly system 10.

Figure 101:
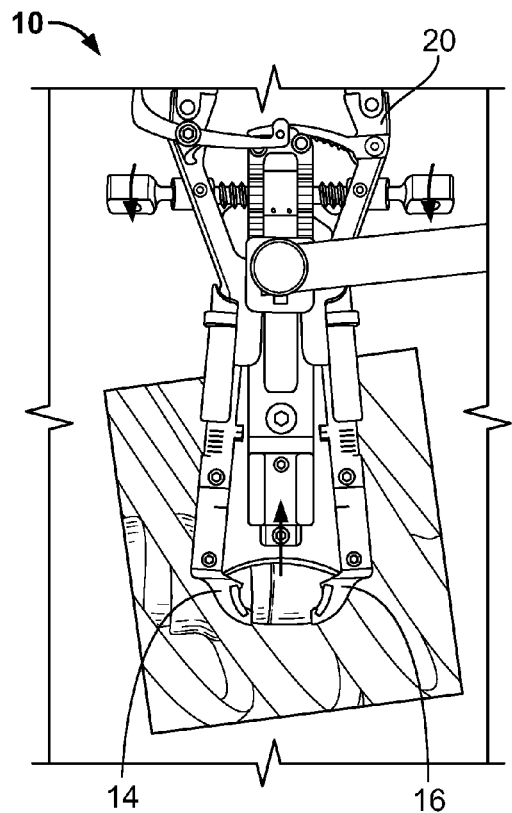

According to a first alternative, illustrated in FIG. 100, the retractor assembly 10 may be advanced to the target vertebra with the handle assembly 20 facing anteriorly. In this orientation, the center blade 12 is preferably not attached to the retractor assembly 10 and the assembly is passed over dilator 50 with only retractor blades 14 and 16 attached (FIG. 100). Crosstable AP fluoroscopy may be used to confirm the correct position of the retractor blades 14, 16 on the spine. The blades should preferably be parallel with the disc spaces, not the ribs. As in FIG. 101, the retractor assembly 10 is fixed in position by attachment to the articulating arm and then the blades 14, 16 are opened by squeezing the handle assembly 20.

Figure 102:
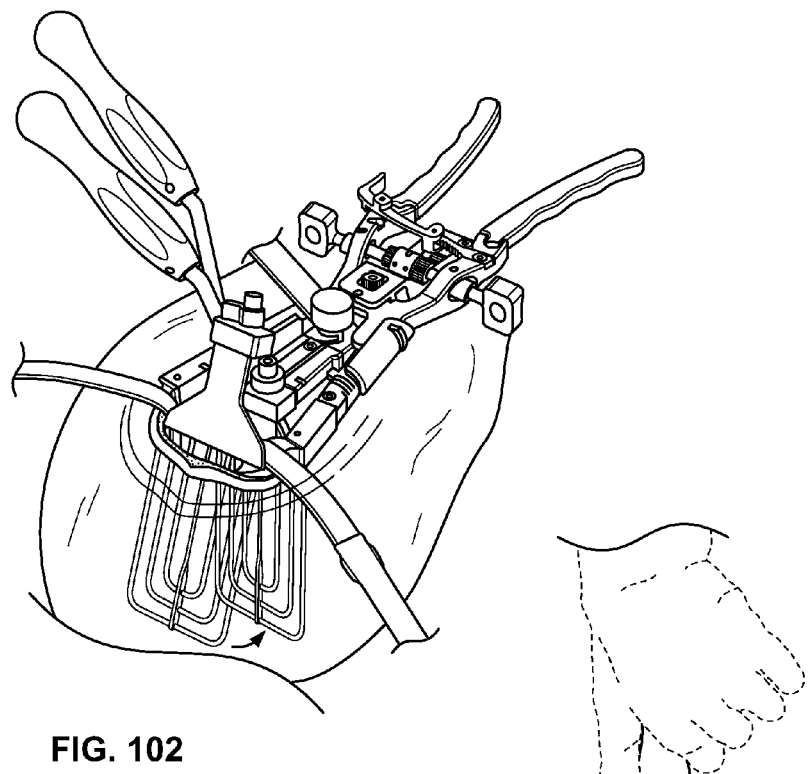
Figure 103:
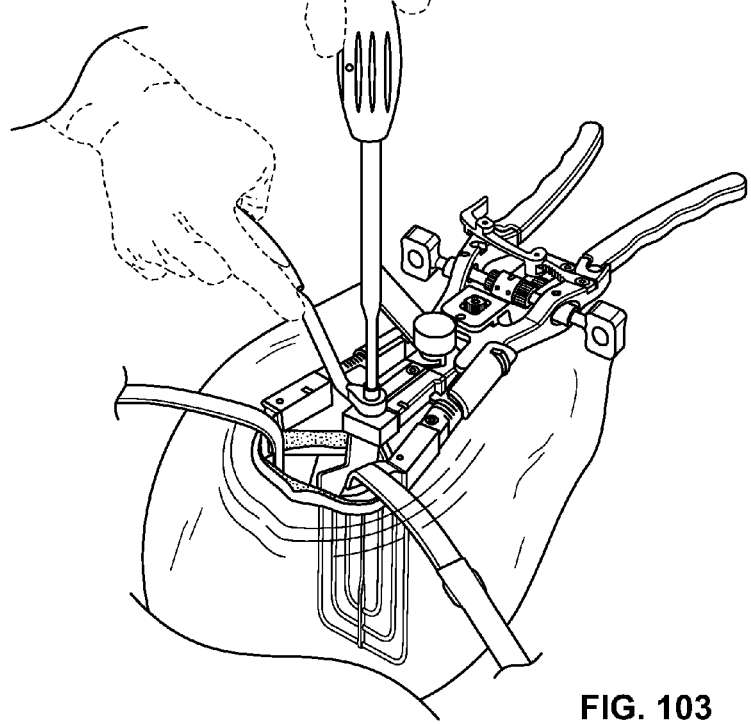
Figure 106:
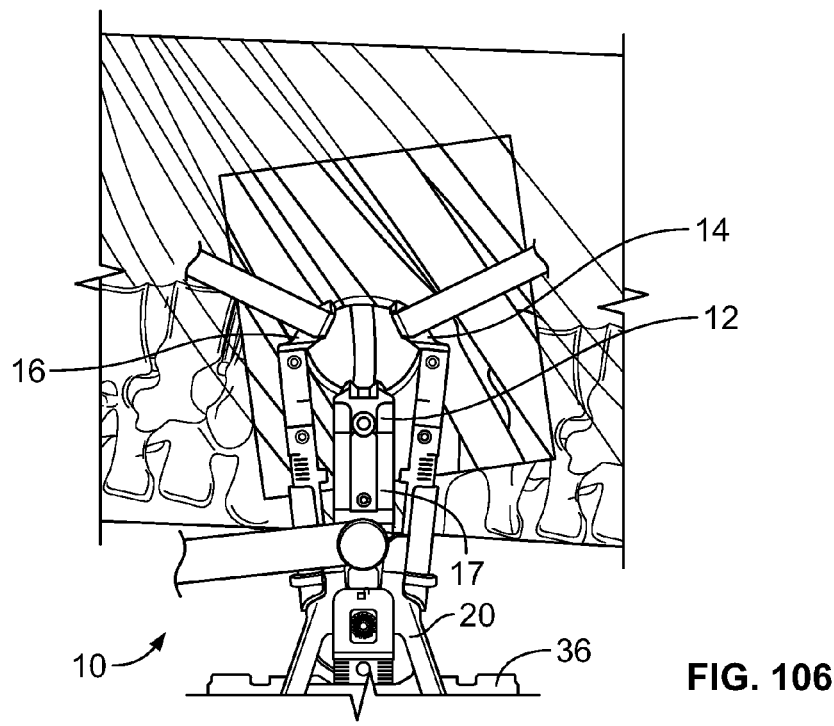

The appropriate length and width lung retractor 440 is attached to the manual retractor handle 447. The alternate retractor blade 440 is then placed between the ribs and used to retract the lung anteriorly (FIG. 102). Thereafter the alternate retractor blade 440 is attached to the translating member 17 of the retractor assembly 10 (FIG. 103), as described above. FIG. 104 illustrates the final exposure through which the corpectomy may be completed. It should be appreciated throughout that while the methods are described as using alternate blade 440 for lung retraction, any of the sequential retractor extenders 350 and 398 or expanding retractor extender 420 may be utilized in place of alternate blade 440 (with the center blade 12 reattached).

With reference to FIG. 105, a second alternative is illustrated in which the retractor assembly 10 may be advanced to the target vertebra with the handle assembly 20 facing posteriorly. The center blade 12 may be ~10 mm shorter than the blades 14 and 16 to provide access for decompressing the spinal cord. The retractor assembly 10 is introduced over the last sequential dilator 50 with the handle assembly 20 pointing posteriorly. A cross-table AP fluoroscopy image may be used to confirm the correct position of the retractor blades 12, 14, 16, on the spine, and to ensure that the blades are parallel with the disc space. The retractor assembly 10 is fixed in position by attachment to the articulating arm and then the blades 14, 16 are opened superior/inferiorly by squeezing the handle assembly 20. Anterior/posterior exposure is achieved by turning knob members 36.

Figure 107:
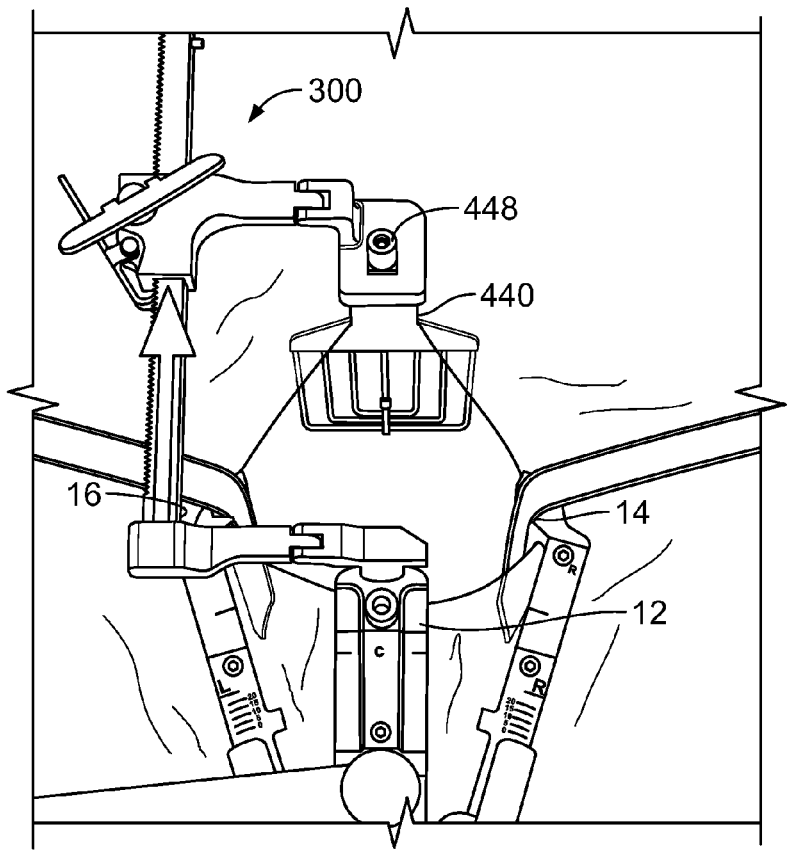

As in FIG. 107, for further retraction of the pleura and diaphragm, the supplemental retractor assembly 300 may be used with alternate retraction blade 440 attached (or any of sequential and expanding retractor extenders 350, 396, and 42 couple with blade 316). The supplemental retractor assembly 300 is attached onto the center blade 12, as described above. The appropriate length and width alternate blade 440 is attached to the retractor handle 447 and the lung and diaphragm are retracted anteriorly. The retractor handle 447 is used to guide the alternate blade 440 onto the supplemental retractor assembly 300 and hold in place while the set screw 448 is tightened.

Figure 108:
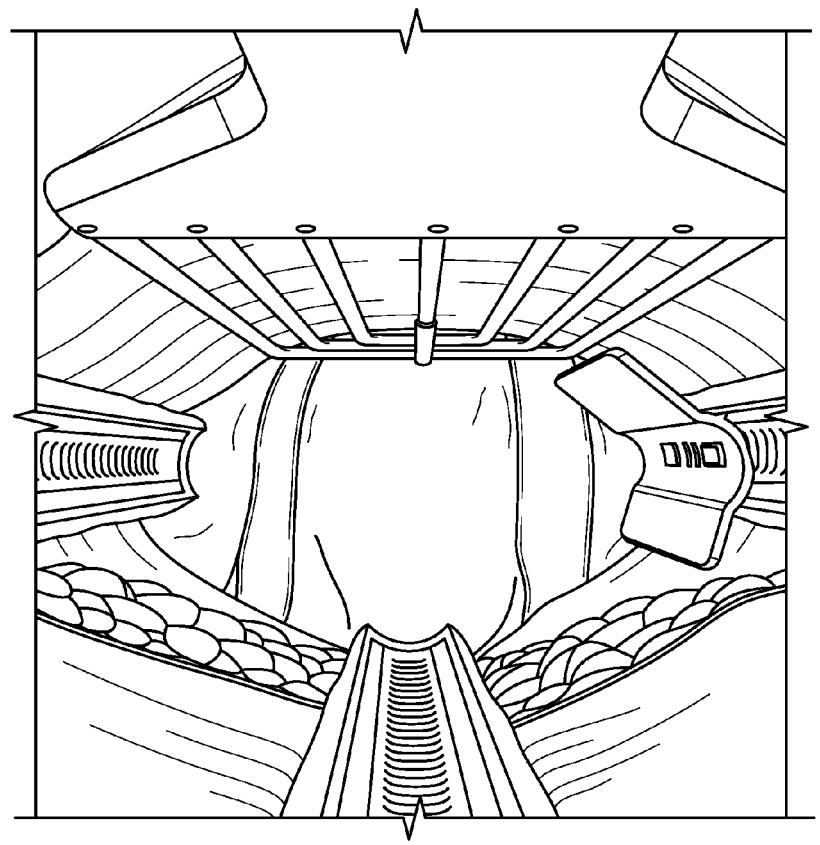

Under direct visualization, a determination should be made as to whether additional retraction of the lung and/or diaphragm is necessary in order to gain access to the spine. Retractor extenders 22, 24, 60, 350, 396, and 420 are available in various sizes to effectively widen or lengthen the blades to retract these tissues if necessary (FIG. 108). Also if necessary, either the pivot wrenches 106 or blade expander 112 can be used to rotate either one or both of the retractor blades 14 and 16. This expands the distal part of the exposure and may be helpful to preferentially adjust the exposure in either direction to gain optimal access to the pathology. Locks 88 will automatically slide forward to secure blade position.

FIG. 108 illustrates the final exposure through which the corpectomy may be performed.

Figure 109:
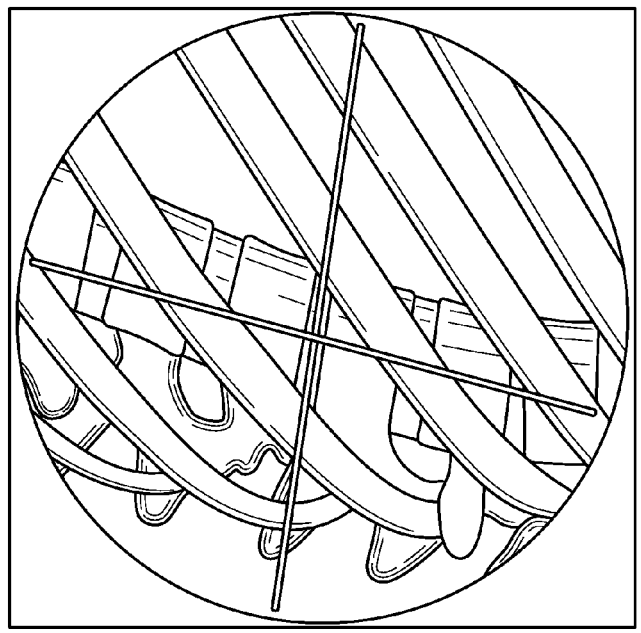
FIGS. 109-120 are figures illustrating steps to perform a lateral extracavitary/retroperitoneal approach to the throacolumbar junction, according to one example.

The next approach method described herein is an extracavitary/retropleural approach generally used for corpectomies at the thoracolumbar junction (L1). With the patient properly positioned, the targeted spinal site is localized using lateral fluoroscopy. One K-wire is placed perpendicular to the spine at the L1 vertebra or pathology. The other K-wire is placed parallel to the spine at the posterior middle-third of the vertebra (FIG. 109). The K-wires may then be used to make two marks on the skin to define the location of the skin incision.

Figure 110:
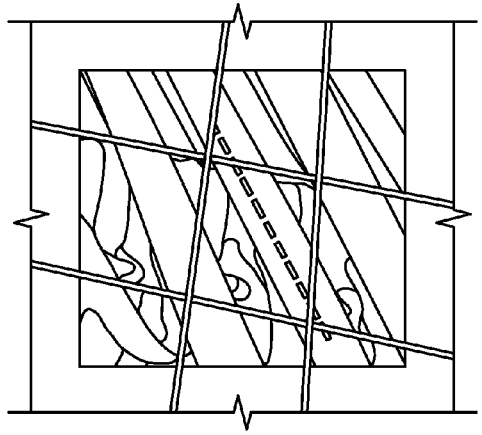
Figure 111:
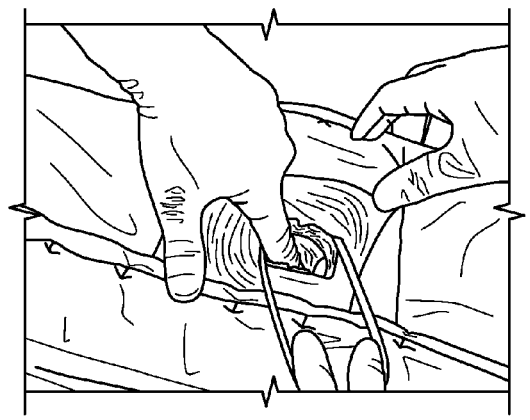
Figure 112:
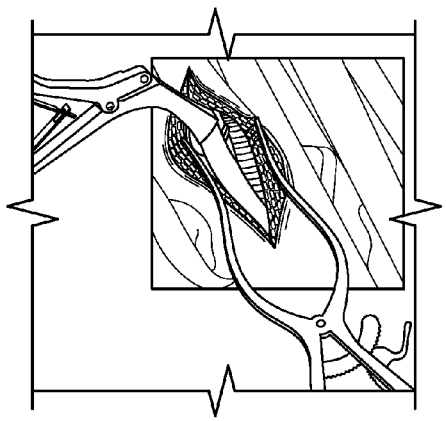
Figure 113:
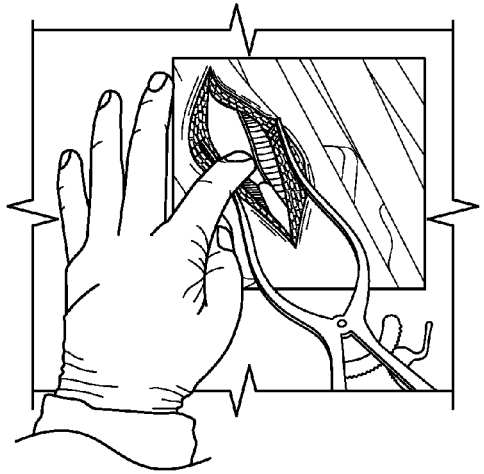

An incision made over the rib along the skin markings (FIG. 110). Dissection is performed through the subcutaneous tissue down to the ribs and then between the ribs through the intercostal muscles down to the pleura. An elevator/raspatory may be passed under the superior aspect of the rib to dissect the intercostal muscle off the rib, while releasing and preserving the neurovascular bundle that lies in the groove on the inferior/deep aspect of the rib. A portion of the rib (~3-5 cm) is then resected using a rib cutter or other resection instruments (FIG. 112). The index finger is used to palpate the pleural space and then sweep along the inferior aspect of the rib to detach the diaphragm from the rib. Once the diaphragm is released, the retroperitoneal and the retropleural cavities communicate. A finger is used to then sweep the diaphragm and pleura anteriorly and away from chest wall. (FIG. 113). It will again be appreciated that while the technique described involves the resection of a small portion (~3-5 cm) of rib, alternative intercostal techniques may be utilized to preserve the rib. To do so the intercostals muscles are dissected and separated from the rib allowing the retractor assembly to pass between and spread the ribs.

Figure 114:
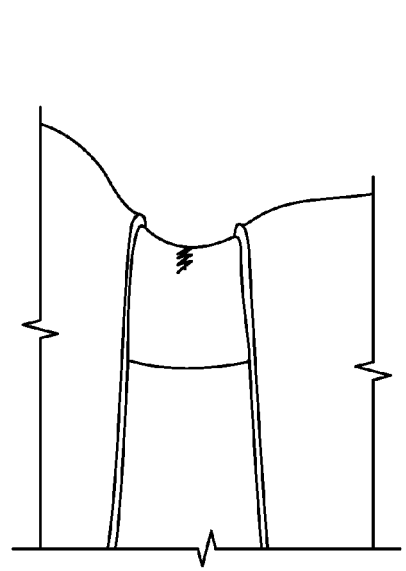

Turning to FIG. 114, another incision is made at a posterolateral location, typically a finger length's distance from the lateral incision and inferior to the $12^{th}$ rib (FIG. 114). It is through this incision that the retroperitoneal space will be accessed via blunt scissor and finger dissection. The blunt scissors are used to carefully spread the muscle fibers, while subsequent finger advancement enables the surgeon to determine whether resistance by the muscle tissue exists. Typically, a loss of resistance by the muscle tissue indicates that the retroperitoneal space has been reached. Care should be taken to avoid abrupt advancement, which could cause perforation of the peritoneum. Once inside the retroperitoneal space, the index finger is used to create space and sweep the peritoneum anteriorly. When the peritoneum is released, the finger is then used to palpate the L1 vertebra, or anterior tip of the transverse process.

Figure 115:
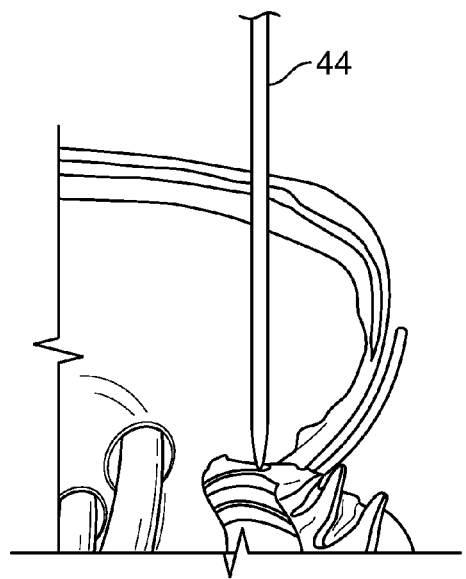
Figure 116:
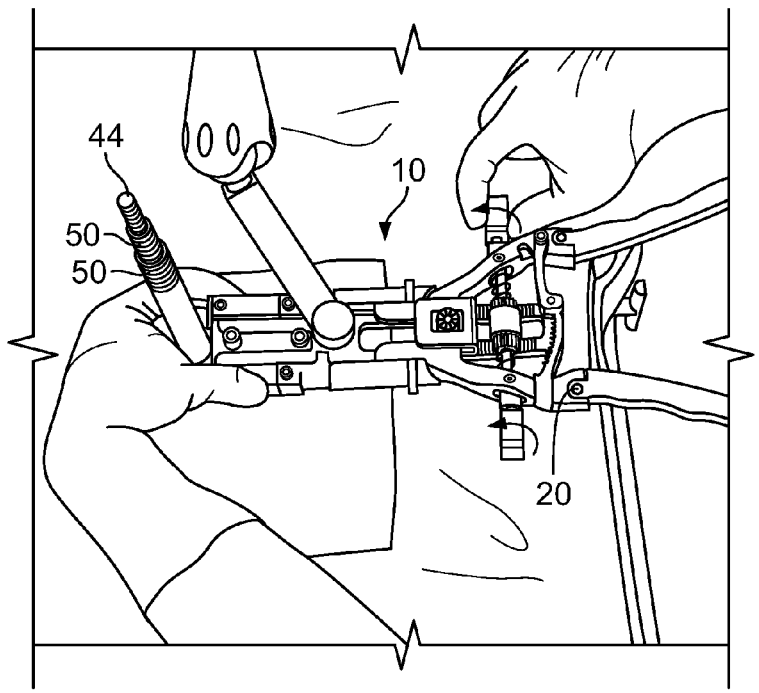

Next, the initial dilating cannula 44 is introduced through the lateral extracavitary skin incision (FIG. 115). Once the initial dilating cannula 44 is docked on the center of the mid vertebra, fluoroscopy should be used to confirm position. A lateral image should confirm that the initial dilating cannula 44 is approximately centered on the vertebra, and parallel with the disc. A cross-table AP image should confirm that the initial dilating cannula 44 is flush with the vertebra. The dilators of sequential dilating system 50 are subsequently passed over the initial dilating cannula 44 down to the spine (FIG. 116). Depth markings on the one or more of the initial dilating cannula 44 and sequential dilators 50 may indicate the size of the appropriate length retractor blades (12, 14, 16, 316, and/or 440) to be attached to the retractor assembly system 10. Arm extensions 41 may be attached to the retractor assembly 10 and used to increase the exposure size.

The retractor assembly 10 may be advanced to the target vertebra over the last dilator 50 with the handle assembly 20 facing posteriorly. A cross-table AP fluoroscopy image may be used to confirm the correct position of the retractor blades 12, 14, 16, on the spine, and to ensure that the blades are parallel with the disc space. The retractor assembly 10 is fixed in position by attachment to the articulating arm and then the blades 14, 16 are opened superior/inferiorly by squeezing the handle assembly 20. Anterior/posterior exposure is achieved by turning knob members 36.

Figure 118:
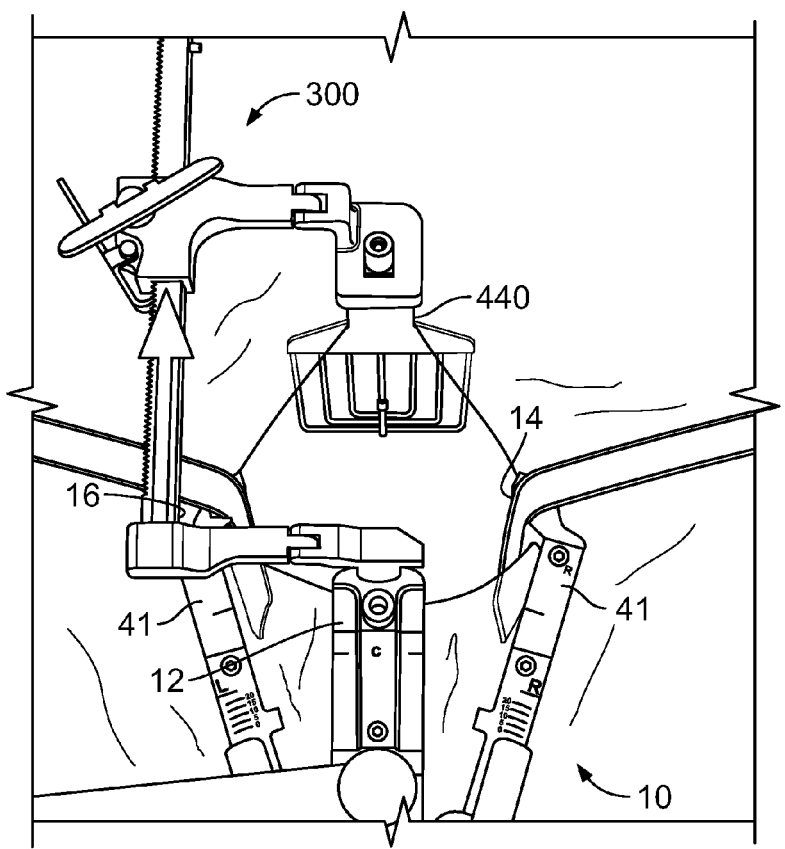

As in FIG. 118, for further retraction of the pleura and diaphragm, the supplemental retractor assembly 300 may be used with alternate retraction blade 440 attached (or any of sequential and expanding retractor extenders 350, 396, and 42 couple with blade 316). The supplemental retractor assembly 300 is attached onto the center blade 12, as described above. The appropriate length and width alternate blade 440 is attached to the retractor handle 447 and the lung and diaphragm are retracted anteriorly. The retractor handle 447 is used to guide the alternate blade 440 onto the supplemental retractor assembly 300 and hold in place while the set screw 448 is tightened.

Figure 119:
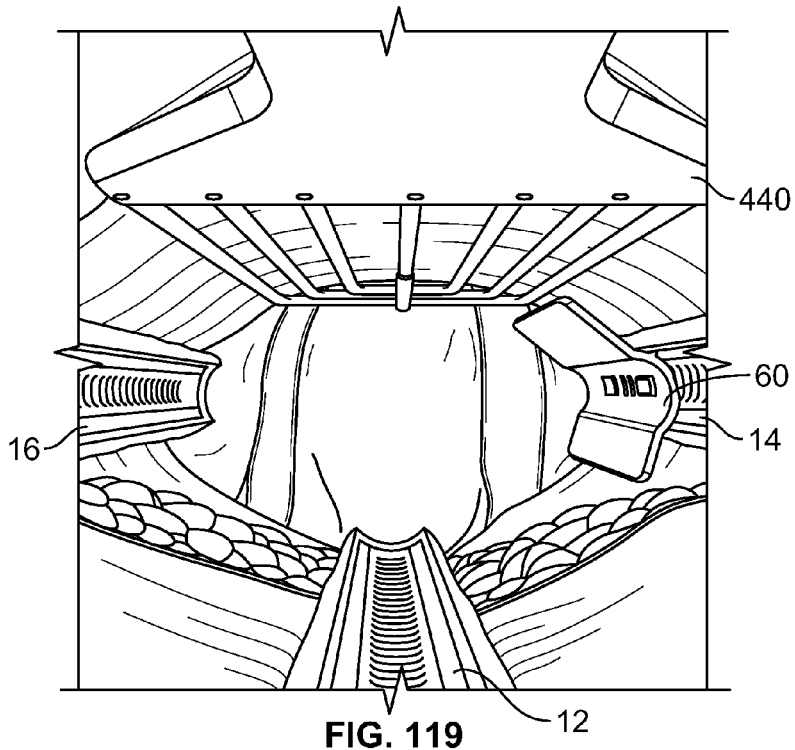
Figure 120:
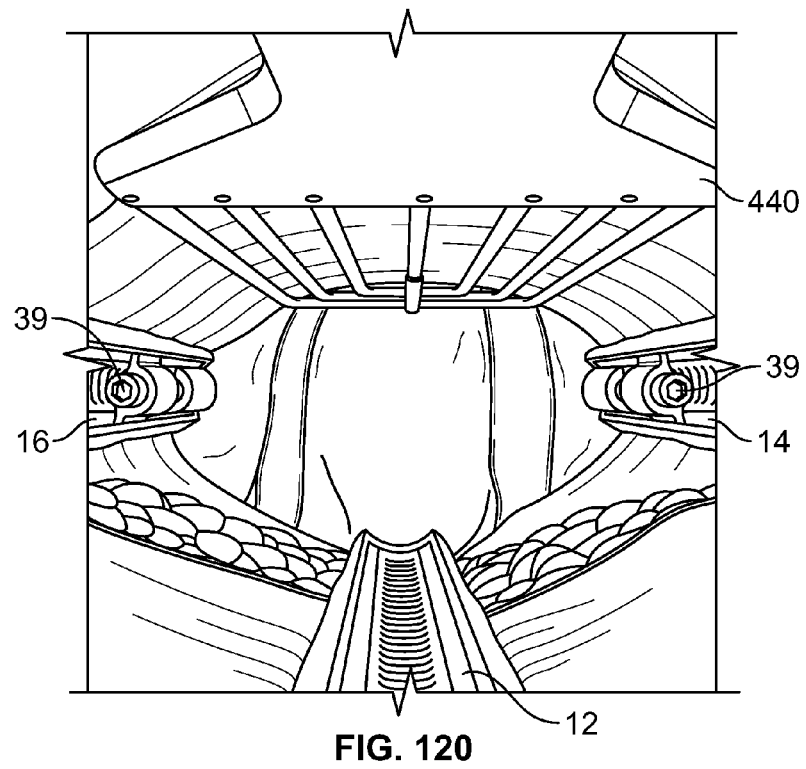

Under direct visualization, a determination may be made as to whether additional retraction of the lung and/or diaphragm is necessary in order to gain access to the spine. Retractor extenders 22, 24, 60, 350, 396, and 420 are available in various sizes to effectively widen or lengthen the blades to retract these tissues if necessary (FIG. 119). Also if necessary, either the pivot wrenches 106 or blade expander 112 can be used to rotate either one or both of the retractor blades 14 and 16. This expands the distal part of the exposure and may be helpful to preferentially adjust the exposure in either direction to gain optimal access to the pathology. Locks 88 will automatically slide forward to secure blade position. FIG. 119 illustrates the final exposure through which the corpectomy may be performed. Optionally, fixation shims 39 can be placed down the blades 14 and 16 and threaded into the vertebrae to attach the retractor assembly 10 to the spine and provide further stabilization.

Figure 121:
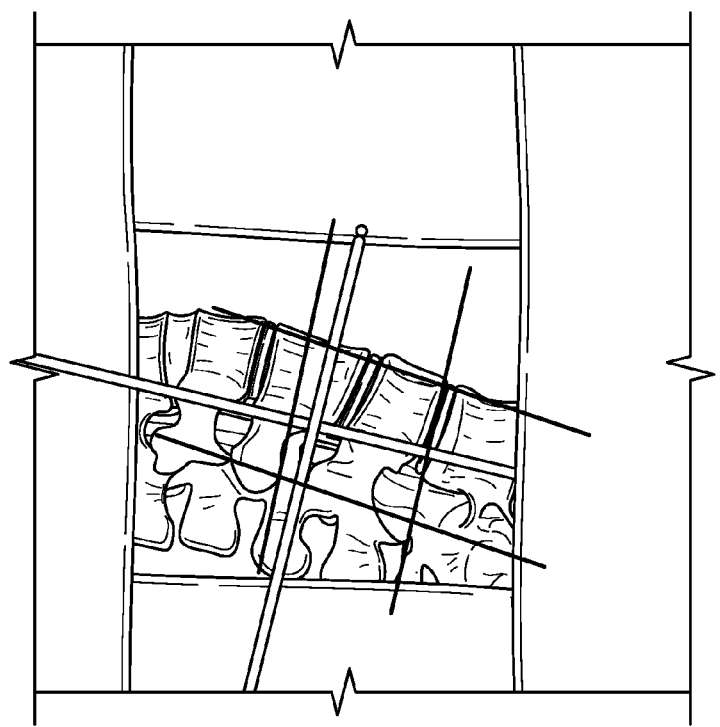
FIGS. 121-130 are figures illustrating the steps to perform a lateral retroperitoneal/transpsoas approach to the lumbar spine, according to one example.
Figure 122:
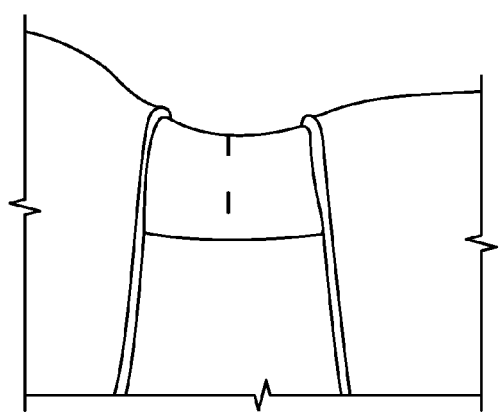
Figure 125:
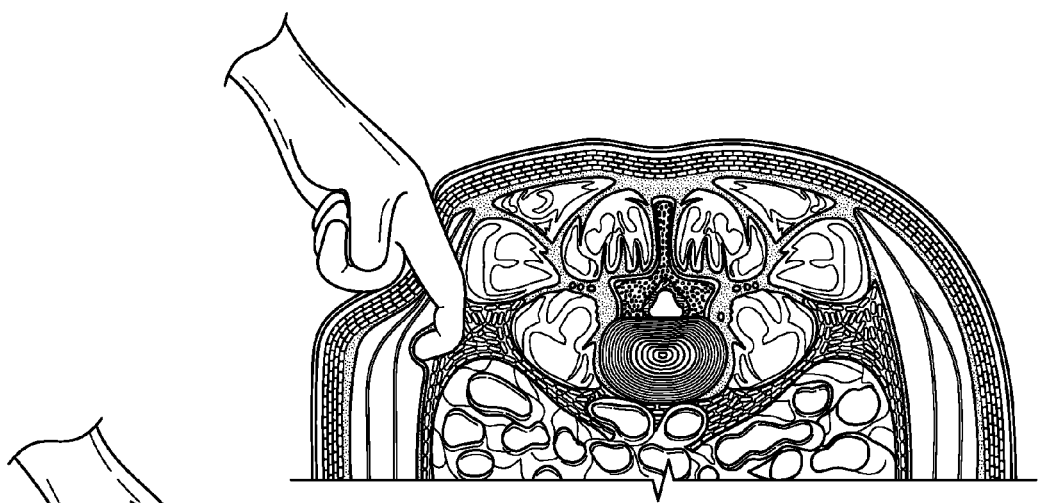
Figure 124:
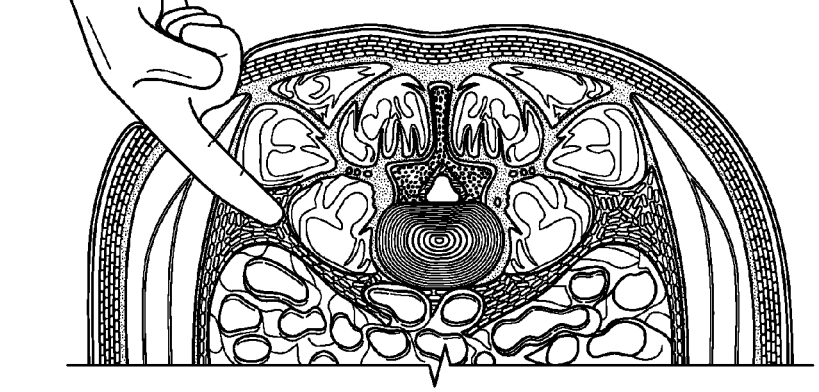
Figure 123:
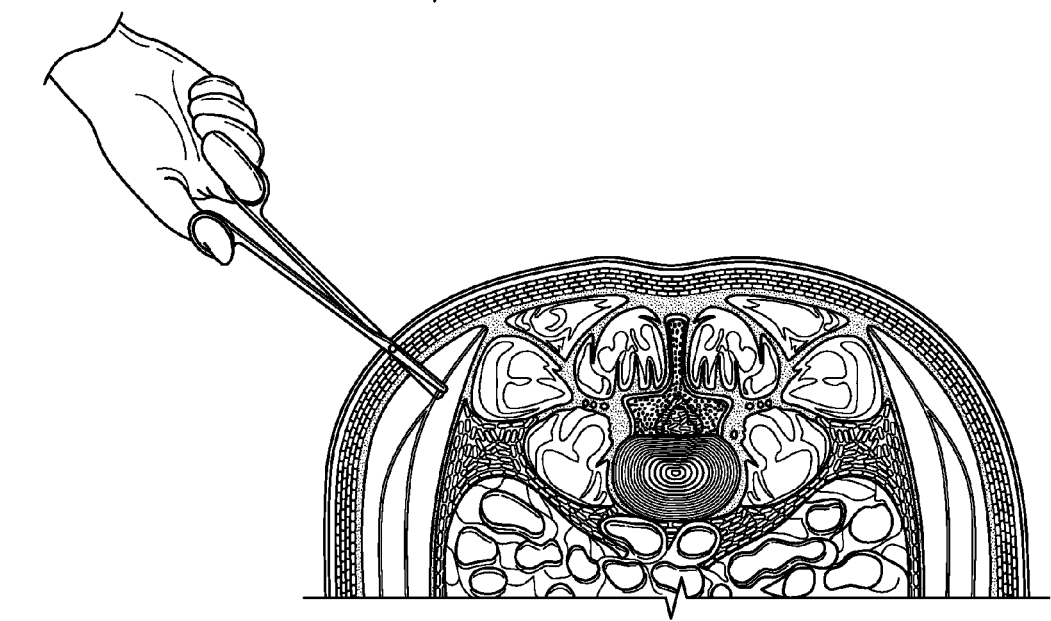

A third approach method described herein is a retroperitoneal transpsoas approach for corpectomies at L2 and below. With the patient properly positioned, the targeted spinal site is localized using lateral fluoroscopy. This is accomplished by crossing two K-wires over the pathologic level centered over the middle of the indicated vertebra (FIG. 121). A mark on the skin is made at the intersection of the K-wires to serve as the location of the skin incision for the operative corridor. Another mark is made on the skin at a posterolateral location between the illium and the rib cage, typically a finger length's distance from the lateral incision and just lateral to the erector spinae muscles (FIG. 122). It is through this incision that the retroperitoneal space will be accessed via blunt scissor and finger dissection (FIGS. 123-125).

Through the posterolateral incision, the subcutaneous tissue layers are dissected using alternating blunt scissor and finger dissection. The blunt scissors are used to carefully spread the muscle fibers, while subsequent finger advancement enables the surgeon to determine whether resistance by the muscle tissue exists. Typically, a loss of resistance by the muscle tissue indicates that the retroperitoneal space has been reached. Once inside the retroperitoneal space, the index finger is used to create space and sweep the peritoneum anteriorly (FIG. 125). When the peritoneum is released, the finger is then used to palpate the psoas muscle, or anterior tip of the transverse process for verification of position within the retroperitoneal space (FIG. 124).

Figure 127:
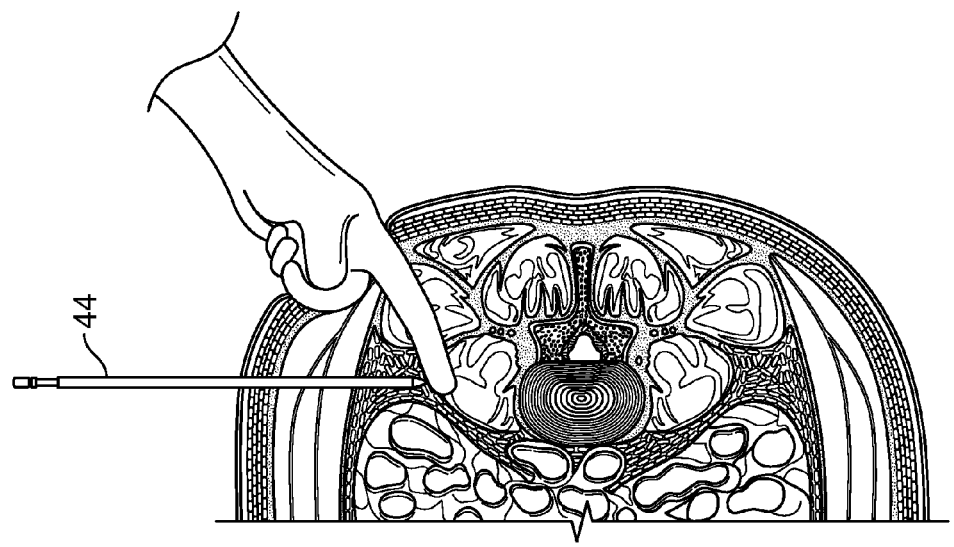
Figure 126:
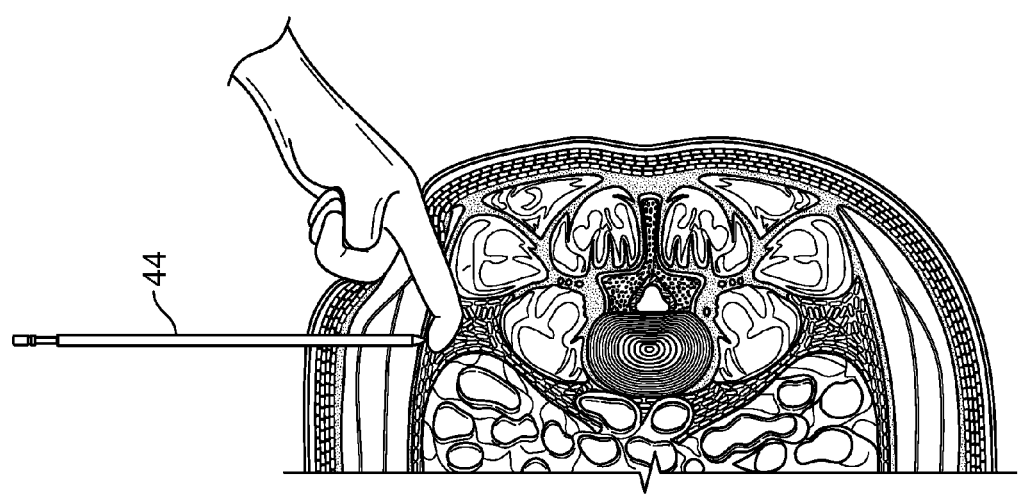

Once the retroperitoneal space is identified, the index finger is swept up to the inside abdominal wall underneath the direct lateral skin mark. This step ensures that a safe pathway exists between the abdominal wall and the psoas muscle. An incision is made at this location and the initial dilating cannula 44 is introduced and the index finger that is inside the retroperitoneal space is then used to escort the initial dilating cannula 44 safely down to the psoas muscle (FIG. 126-127). Upon reaching the psoas muscle with the initial dilating cannula 44, the location is verified with a lateral fluoro image. The ideal location is approximately at the center (or just posterior to center) of the vertebra.

Figure 128:
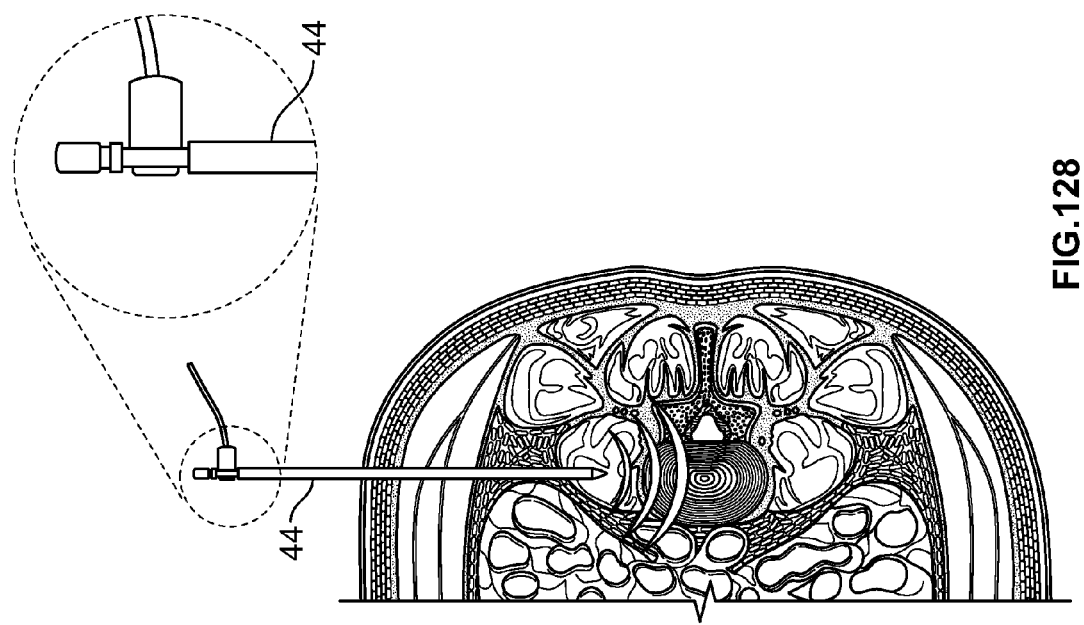

The fibers of the psoas muscle are then split using blunt dissection with the initial dilation cannula, which is slowly advanced while nerve monitoring is performed (as described above) in order to avoid the nerves located in the psoas (FIG. 128). If the initial dilation cannula 44 is determined to be too close to a nerve, the dilation cannula 44 is slowly rotated 360° to determine the location of the nerve. If alert-threshold levels indicate an unsafe proximity to a nerve, the dilation cannula 44 is removed from the psoas and moved slightly away from the location of the nerve, and a new path through the psoas muscle is attempted.

Figure 129:
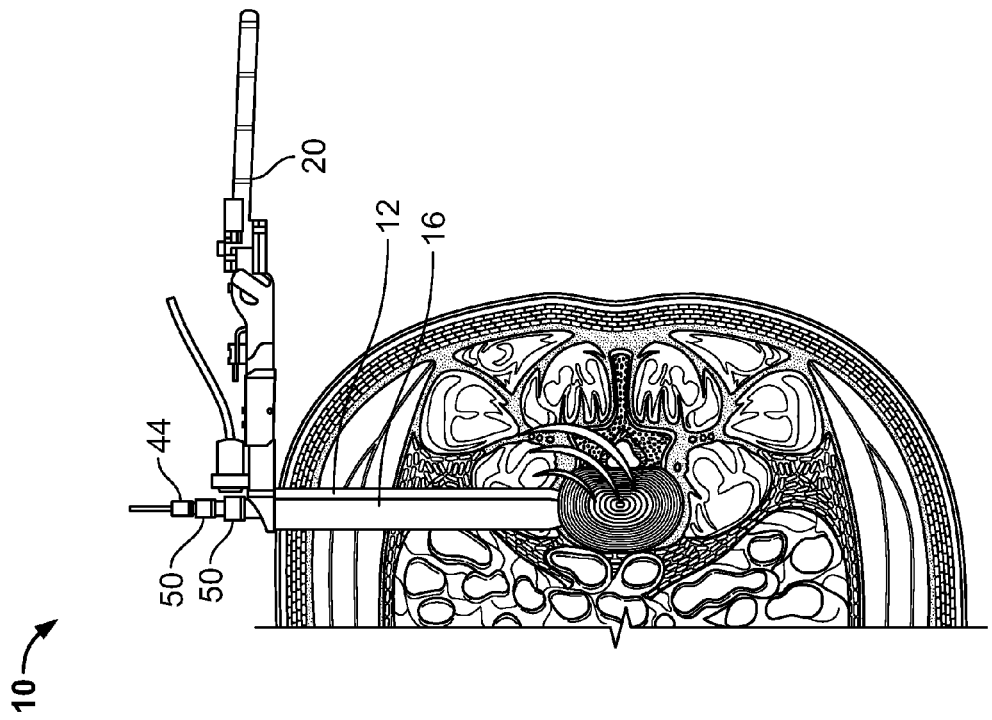

Once the initial dilator is docked on the posterior third of the mid vertebra, fluoroscopy should be used to confirm position. A lateral image should confirm that the initial dilation cannula 44 is approximately centered on the vertebra, and parallel with, the disc. A cross-table AP image should confirm that initial dilation cannula 44 is flush with the vertebra. The dilators of sequential dilating system 50 are subsequently passed over the initial dilating cannula 44 down to the spine (FIG. 129). Nerve monitoring may again be performed during dilation. Depth markings on the one or more of the initial dilating cannula 44 and sequential dilators 50 may indicate the size of the appropriate length retractor blades (12, 14, 16, 316, and/or 440) to be attached to the retractor assembly system 10.

The retractor assembly 10 is introduced over the final dilator 50 with the handles pointing posteriorly. The nerve monitoring may be performed by attaching a dynamic stimulation clip to the post on top of the center blade 12 to stimulate an electrode on the distal end of the blade (FIG. 129). Cross-table AP fluoroscopy is used to confirm the correct position of the retractor assembly blades 12, 14, 16 on the spine, and to ensure that the blades are parallel with the disc space.

The retractor assembly 10 is fixed in position by attachment to the articulating arm and then the blades 14, 16 are opened superior/inferiorly by squeezing the handle assembly 20. Anterior/posterior exposure is achieved by turning knob members 36.

As in FIG. 118, for further retraction of the pleura and diaphragm, the supplemental retractor assembly 300 may be used with alternate retraction blade 440 attached (or any of sequential and expanding retractor extenders 350, 396, and 42 couple with blade 316). The supplemental retractor assembly 300 is attached onto the center blade 12, as described above. The appropriate length and width alternate blade 440 is attached to the retractor handle 447 and the lung and diaphragm are retracted anteriorly. The retractor handle 447 is used to guide the alternate blade 440 onto the supplemental retractor assembly 300 and hold in place while the set screw 448 is tightened.

Figure 130:
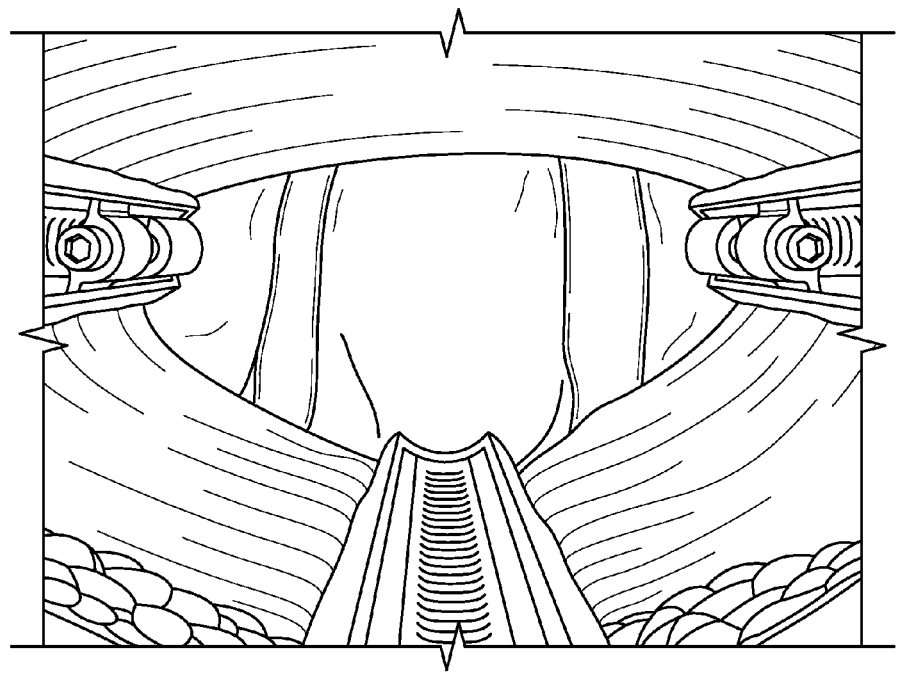

Additional retractor extenders can be placed down the blades if necessary. A Penfield, Nerve Retractor, or Psoas Retractor can be used to tuck residual tissue behind the extenders. Bipolar electrocautery can be used, if necessary, to further prepare for disc visualization. Also if necessary, either the pivot wrenches 106 or blade expander 112 can be used to rotate either one or both of the retractor blades 14 and 16. This expands the distal part of the exposure and may be helpful to preferentially adjust the exposure in either direction to gain optimal access to the pathology. Locks 88 will automatically slide forward to secure blade position. Optionally, fixation shims 39 can be placed down the blades 14 and 16 and threaded into the vertebrae to attach the retractor assembly 10 to the spine and provide further stabilization. FIG. 130 illustrates the final exposure through which the corpectomy may be performed.

Figure 131:
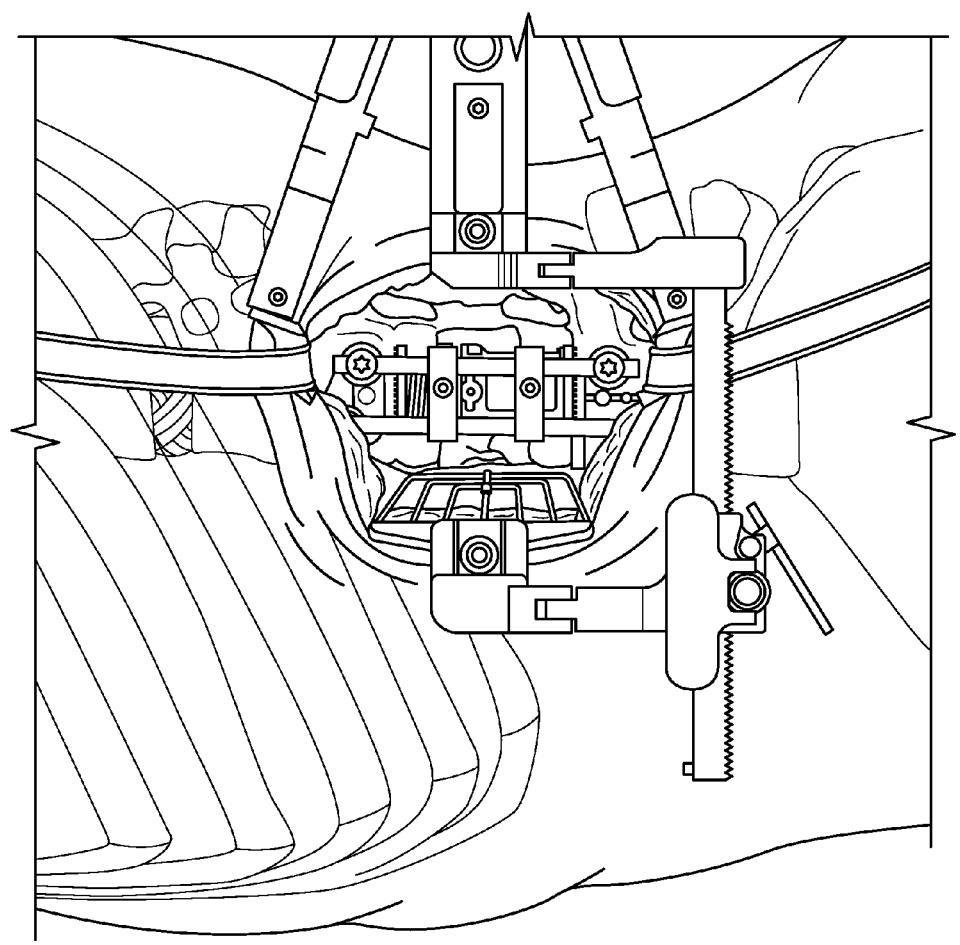
FIG. 131 is an illustration depicting a completed corpectomy procedure with a vertebral body replacement implant and supplemental fixation performed through a lateral approach.
Figure 132:
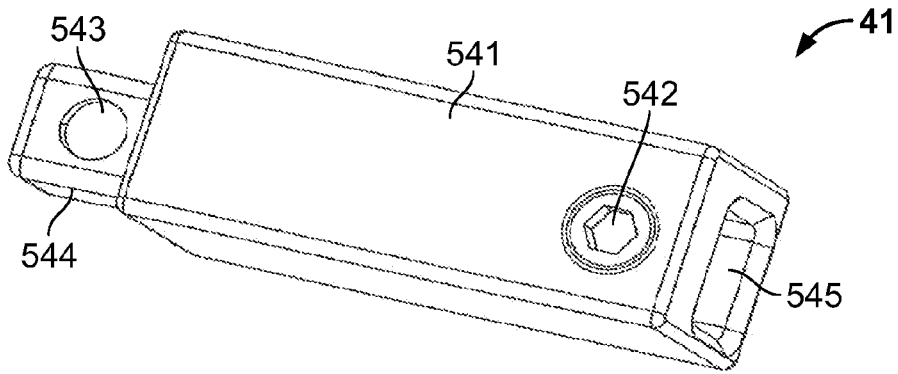
FIGS. 132-137 are views of retractor extensions that extend the distance between the handle and the retractor blades.
Figure 133:
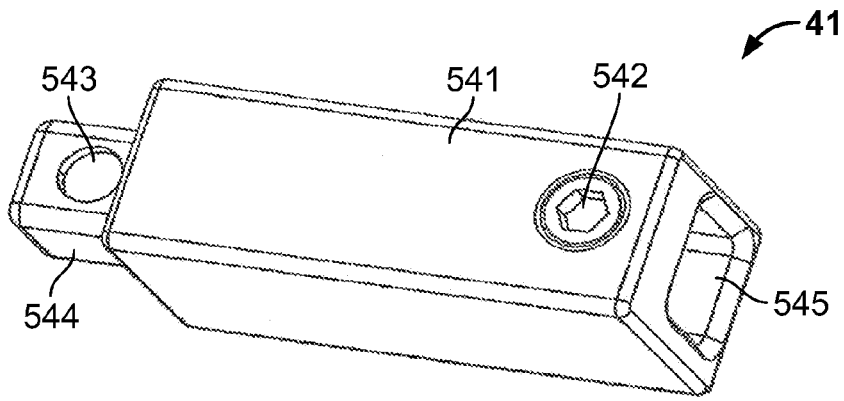
Figure 134:
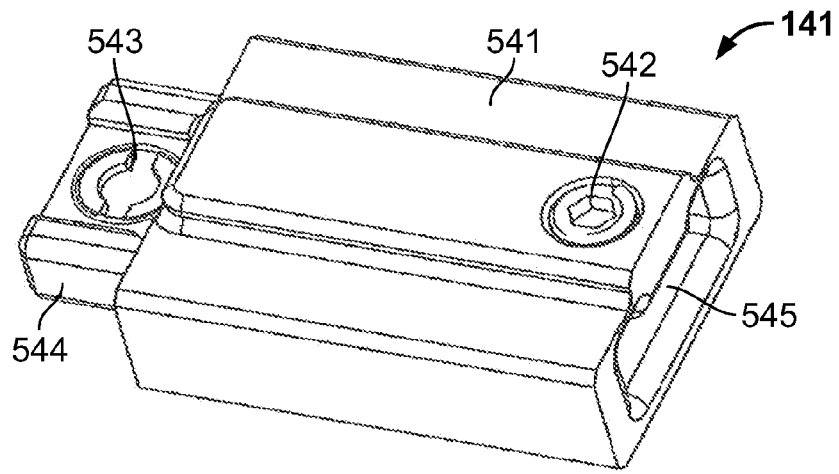
Figure 135:
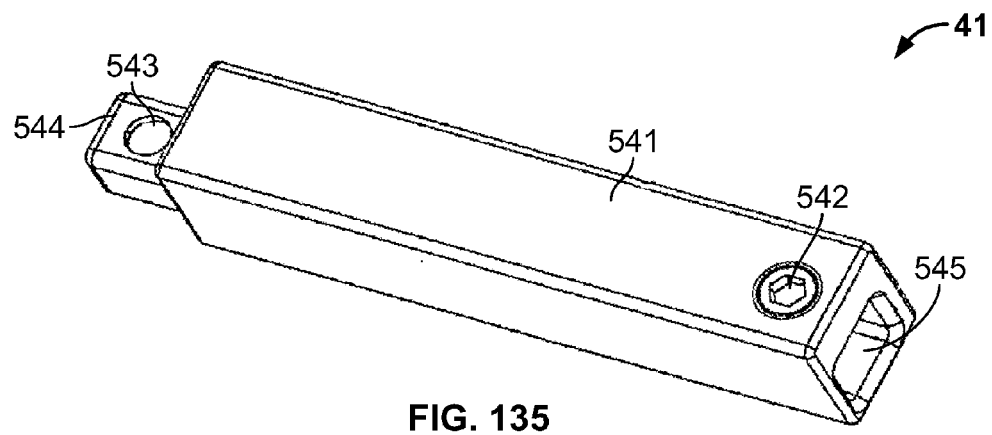
Figure 136:
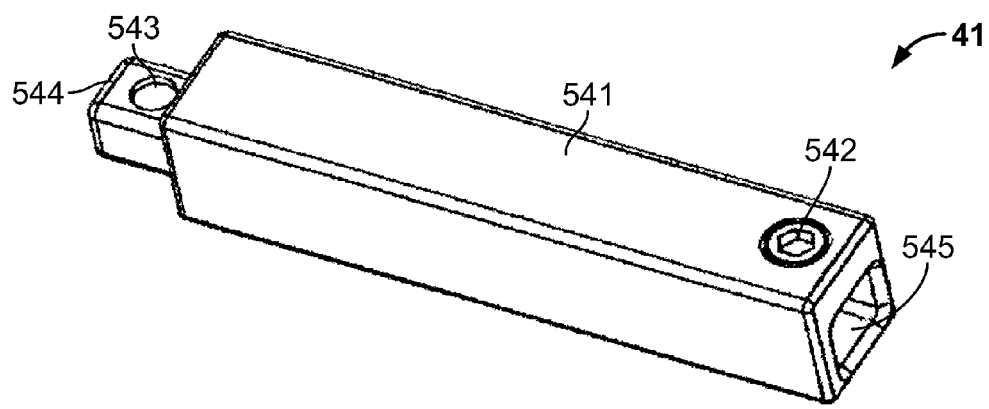
Figure 137:
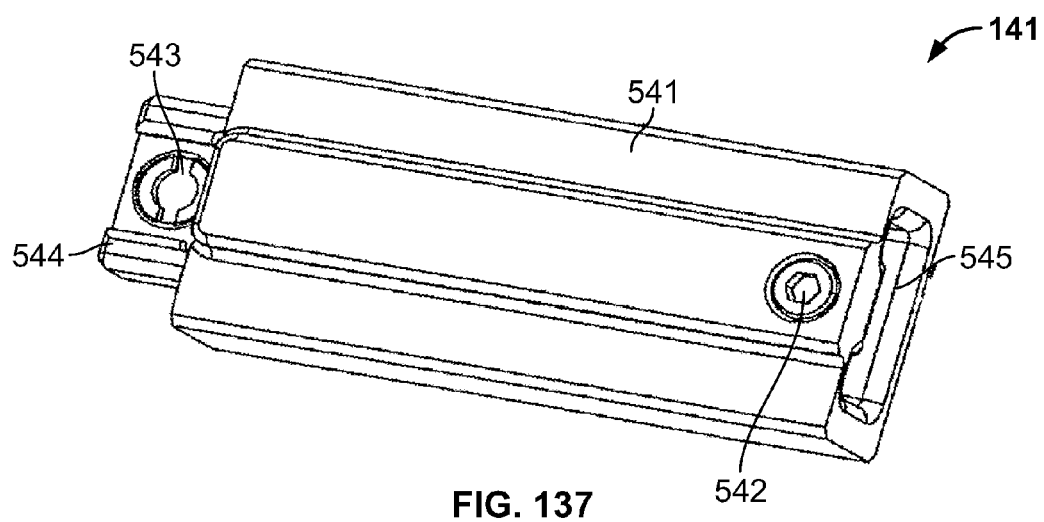

With reference to FIG. 131, once access to the targeted spinal site has been achieved by one of the methods described above, the surgeon may perform the remainder of the corpectomy procedure, including preparing the disc spaces, removing the vertebral body, implant placement, and fixation. By way of example, the target site may be prepared by first creating an annulotomy on the superior disc space. If inside thoracic cavity, the parietal pleura covers the surface of the spine and is incised in order to gain access to the disc space. The cobb elevator may be passed along both endplates to release disc and cartilage from the subchondral bone. Cobbs may correspond to the various sized end-caps for the expandable vertebral body replacement. pituitaries, curettes, disc cutters, endplate scrapers, and other disc preparation instruments can be used to thoroughly evacuate the disc. The process is followed for the inferior disc space. The segmental vessels are clipped or coagulated using bipolar forceps.

Endoscopic kittners may be used to release the psoas, diaphragm, or pleura off the vertebra. A corpectomy is performed to a portion or to the entire vertebra with traditional instrumentation. A chisel may be used to make lateral and superior/inferior gutters in the vertebra. Fluoroscopic depth markings on the chisels correspond to expandable vertebral body replacement core widths (e.g. 18 and 22 mm). Rotating kerrisons may be used to incise the vertebra, while maintaining a cutting motion away from the canal. Decompression may be achieved by resecting the posterior cortex of the vertebra, pathology compressing the cord, and the posterior longitudinal ligament. The bone and soft tissue is resected away from the canal by orientating the rotating kerrison. If a drill is preferred, bone removal may be accomplished with a 3-4 mm bit and a high speed drill. The corpectomy site should be extended until healthy, vascularized bone surface is exposed to facilitate the insertion of the expandable vertebral body replacement.

Figure 138:
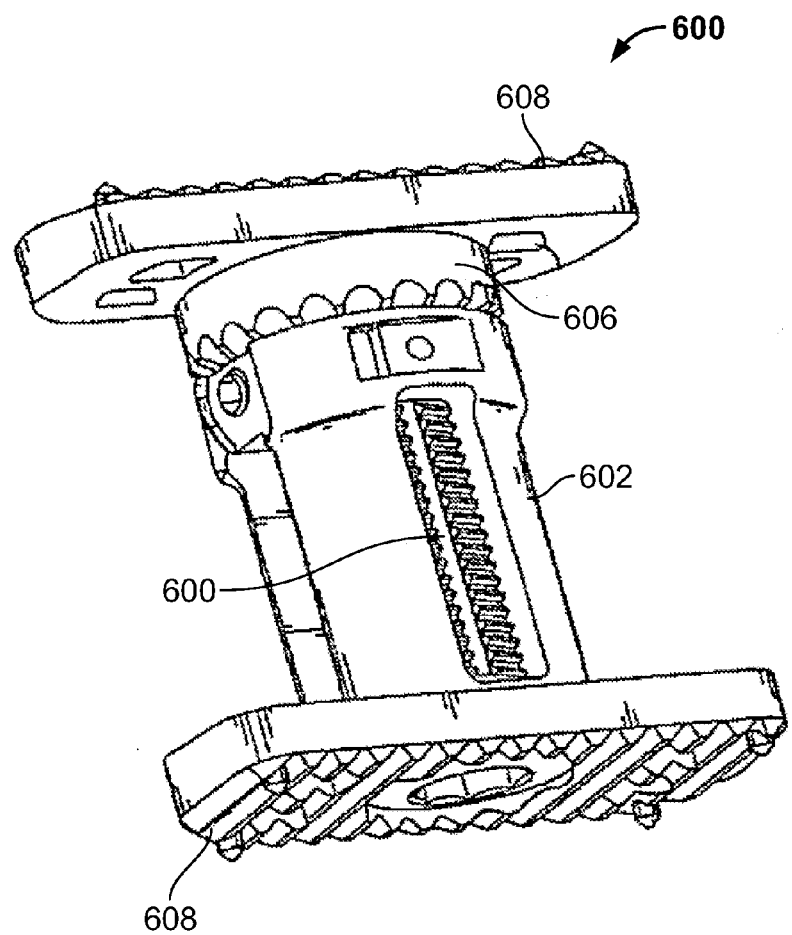
FIG. 138 is a perspective view of an example embodiment of a corpectomy implant optimized for implantation through one of the lateral methods described herein.

Once the target site is fully prepared a vertebral body replacement implant may be implanted to maintain the spacing between the remaining adjacent vertebral bodies. By way of example, the implant may be an embodiment of the implant shown and described in the commonly owned and co-pending U.S. patent application Ser. No. 12/661,206, filed Mar. 12, 2010. FIG. 138 illustrates an example embodiment of such an implant. The expandable corpectomy implant 600 includes an outer core 602, an inner core 604, an adjustment ring 606 and upper and lower endplates 608. In use the inner core 604 expands from the outer core 602 to fill the space created between the remaining vertebrae. Significantly, the upper and lower endplates 608 are optimized for implantation through one of the minimally invasive lateral approaches described above. The endplates are dimensioned to span the apophyseal ring, reducing the possibility of subsidence.

Supplemental fixation may also be performed. By way of example, the fixation systems shown and described in U.S. patent application Ser. No. 12/579,394, filed Oct. 14, 2009 respectively, may be used for supplemental fixation. Additionally, while nerve monitoring was described above for determining nerve proximity in the psoas muscle, additional nerve monitoring may be utilized throughout the procedures. By way of example, MEP and SSEP monitoring may be conducted as described in the commonly owned and co-pending Int'l. Patent App. Ser. No. PCT/US2008/124079, filed Apr. 3, 2008.

What is claimed is:

1. A minimally invasive tissue retraction system for creating a minimally invasive operating corridor to the spine comprising:
    a retractor body having first and second pivotable arms movable relative to each other, the first pivotable arm extending along a first longitudinal axis and the second arm extending along a second longitudinal axis, and a third translating arm moveable relative to the first and second pivotable arms, each of the first, second, and third arms having a distal attachment site configured to rigidly couple a retractor blade, said first pivotable arm having a first arm extender extending along the first longitudinal axis and coupled to the distal attachment site of the first arm, the first extender having a proximal end configured to couple to the distal attachment site of the first arm and a distal end configured to rigidly attach a retractor blade, said second pivotable arm having a second arm extender extending along the second longitudinal axis and coupled to the distal attachment site of the second arm, the second arm extender having a proximal end configured to couple to the distal attachment site of the second arm and a distal end configured to rigidly attach a retractor blade;
    a first retractor blade attached to said distal end of the first arm extender, and a second retractor blade attached to said distal end of the second arm extender, each of said first and second retractor blades pointed generally perpendicularly relative to said retractor body; and
    a third retractor blade shaped to retract lung tissue from said operative corridor, the third retractor blade coupled to the third translating arm, and wherein said third retractor blade is also pointed generally perpendicular relative to said retractor body.

2. The system of claim 1, wherein said third blade has a generally square distal end to match the contour of the spine.

3. The system of claim 1, wherein said third blade has a wire frame.

4. The system of claim 3, wherein said third blade has a proximal neck region that is thinner than a body region.

5. The system of claim 4, wherein a length of a proximal neck is between 15 and 25 mm.

6. The system of claim 5, wherein the third blade has a quick connect feature for engaging a manual handle.

7. The system of claim 4, wherein the proximal neck region is connected to the wire frame via angled sidewalls.

8. The system of claim 1, wherein the proximal end of the first arm extension includes a male extension that is configured to be received within a female aperture of first arm distal attachment site and a screw locks said first arm extension to said first arm.

9. The system of claim 8, wherein the distal end of the first arm extension includes a female aperture configured to receive a male extension on the first retractor blade and a screw locks said retractor blade to said first arm extension.

10. The system of claim 9, wherein the third translating arm includes a third arm extension attached to the distal attachment end and the third retractor blade is attached to a distal end of the third arm extension.

* * * * *